US012600761B2

(12) United States Patent
Liang et al.

(10) Patent No.: US 12,600,761 B2
(45) Date of Patent: Apr. 14, 2026

(54) METHODS AND COMPOSITIONS FOR PURIFICATION OF TRIMERIC FUSION PROTEINS

(71) Applicant: Sichuan Clover Biopharmaceuticals, Inc., Chengdu (CN)

(72) Inventors: Peng Liang, Chengdu Sichuan (CN); Joshua Liang, Chengdu Sichuan (CN)

(73) Assignee: Sichuan Clover Biopharmaceuticals, Inc., Chengdu (CN)

( * ) Notice: Subject to any disclaimer, the term of this patent is extended or adjusted under 35 U.S.C. 154(b) by 515 days.

(21) Appl. No.: 18/022,140

(22) PCT Filed: Aug. 30, 2021

(86) PCT No.: PCT/CN2021/115245
§ 371 (c)(1),
(2) Date: Feb. 18, 2023

(87) PCT Pub. No.: WO2022/042716
PCT Pub. Date: Mar. 3, 2022

(65) Prior Publication Data
US 2024/0301029 A1 Sep. 12, 2024

(30) Foreign Application Priority Data

Aug. 31, 2020 (WO) ................ PCT/CN2020/112439
Apr. 13, 2021 (WO) ................ PCT/CN2021/087055

(51) Int. Cl.
| | |
|---|---|
| *C07K 14/705* | (2006.01) |
| *C07K 1/22* | (2006.01) |
| *C07K 14/005* | (2006.01) |
| *C07K 14/78* | (2006.01) |

(52) U.S. Cl.
CPC ............ *C07K 14/7056* (2013.01); *C07K 1/22* (2013.01); *C07K 14/005* (2013.01); *C07K 14/78* (2013.01); *C07K 2319/30* (2013.01); *C12N 2770/20051* (2013.01)

(58) Field of Classification Search
CPC .... C07K 14/7056; C07K 1/22; C07K 14/005; C07K 14/78; C07K 2319/30; C07K 2319/02; C07K 2319/20; C07K 2319/50; C07K 2319/70; C07K 2319/735; C12N 2770/20051
See application file for complete search history.

(56) References Cited

U.S. PATENT DOCUMENTS

| | | | |
|---|---|---|---|
| 5,605,690 | A | 2/1997 | Jacobs et al. |
| 6,060,273 | A | 5/2000 | Dirks et al. |
| 6,171,827 | B1 | 1/2001 | Bulleid et al. |
| 6,190,886 | B1 | 2/2001 | Hoppe et al. |
| 6,277,600 | B1 | 8/2001 | Tomita et al. |
| 6,617,431 | B1 | 9/2003 | Gruber et al. |
| 7,268,116 | B2 | 9/2007 | Liang |
| 7,666,837 | B2 | 2/2010 | Liang |
| 7,691,815 | B2 | 4/2010 | Liang |
| 10,618,949 | B2 | 4/2020 | Liang |
| 10,906,944 | B2 | 2/2021 | He et al. |
| 10,960,070 | B2 | 3/2021 | Graham et al. |
| 11,111,284 | B2 | 9/2021 | Faustman et al. |
| 2003/0143564 | A1 | 7/2003 | Burgeson et al. |
| 2003/0148466 | A1 | 8/2003 | Fox et al. |
| 2004/0197876 | A1 | 10/2004 | Tschopp et al. |
| 2005/0202537 | A1 | 9/2005 | Liang |
| 2007/0087413 | A1 | 4/2007 | Liang |
| 2007/0117755 | A1 | 5/2007 | Liang |
| 2020/0009244 | A1 | 1/2020 | He et al. |
| 2020/0190181 | A1 | 6/2020 | Liang |
| 2020/0199187 | A1 | 6/2020 | Liang |
| 2021/0246170 | A1 | 8/2021 | Langedijk et al. |
| 2021/0268102 | A1 | 9/2021 | Yan et al. |
| 2021/0275665 | A1 | 9/2021 | Cho et al. |
| 2021/0308257 | A1 | 10/2021 | Kuo et al. |
| 2021/0355170 | A1 | 11/2021 | Whitehead et al. |

FOREIGN PATENT DOCUMENTS

| | | |
|---|---|---|
| CN | 106928326 A | 7/2017 |
| CN | 111592602 A | 8/2020 |
| CN | 112220920 | 1/2021 |
| CN | 112266411 | 1/2021 |
| CN | 112480217 | 3/2021 |

(Continued)

OTHER PUBLICATIONS

K Singh, Raushan, et al. "Protein engineering approaches in the post-genomic era." Current Protein and Peptide Science 19.1 (2018): 5-15 (Year: 2018).*

(Continued)

*Primary Examiner* — Paul J Holland
*Assistant Examiner* — Erica Nicole Jones-Foster
(74) *Attorney, Agent, or Firm* — Knobbe, Martens, Olson & Bear, LLP

(57) ABSTRACT

The present disclosure provides methods and compositions for affinity purification of proteins containing a C-terminal polypeptide sequence of a procollagen, such as trimeric fusion proteins. Also provided are polypeptides, fusion proteins, and recombinant polypeptides containing an Endo 180 ecto-domain or portion thereof capable of reversibly binding a C-terminal polypeptide sequence of a procollagen. Also provided are articles of manufacture, kits, and apparatus related to the Endo 180 ecto-domain polypeptides.

17 Claims, 6 Drawing Sheets

Specification includes a Sequence Listing.

(56) References Cited

FOREIGN PATENT DOCUMENTS

| CN | | 113185613 | 4/2021 |
|---|---|---|---|
| CN | | 113234170 | 4/2021 |
| CN | | 113480618 | 10/2021 |
| WO | WO | 1997/017988 | 5/1997 |
| WO | WO | 2016/029043 | 2/2016 |
| WO | WO | 2021/154812 | 8/2021 |
| WO | WO | 2021/160346 | 8/2021 |
| WO | WO | 2021/163365 | 8/2021 |
| WO | WO | 2021/170131 | 9/2021 |
| WO | WO | 2021/174128 | 9/2021 |
| WO | WO | 2021/178318 | 9/2021 |
| WO | WO | 2021/178321 | 9/2021 |
| WO | WO | 2021/178971 | 9/2021 |
| WO | WO | 2021/189056 | 9/2021 |
| WO | WO | 2021/198706 | 10/2021 |
| WO | WO | 2021/204179 | 10/2021 |
| WO | WO | 2021/205455 | 10/2021 |
| WO | WO | 2021/214703 | 10/2021 |
| WO | WO | 2021/216743 | 10/2021 |
| WO | WO | 2021/226436 | 11/2021 |
| WO | WO | 2021/228842 | 11/2021 |
| WO | WO | 2021/243122 | 12/2021 |
| WO | WO | 2021/245611 | 12/2021 |
| WO | WO | 2021/249012 | 12/2021 |
| WO | WO | 2021/249116 | 12/2021 |
| WO | WO | 2021/249451 | 12/2021 |

OTHER PUBLICATIONS

Zhang, Meiling, David A. Case, and Jeffrey W. Peng. "Propagated perturbations from a peripheral mutation show interactions supporting WW domain thermostability." Structure 26.11 (2018): 1474-1485. (Year: 2018).*

Addetia et al., "Neutralizing Antibodies Correlate with Protection from SARS-CoV-2 in Humans during a Fishery Vessel Outbreak with a High Attack Rate," J Clin Microbiol. (2020) 58(11):e02107-20.

Baker et al., "Structures of bovine and human papillomaviruses. Analysis by cryoelectron microscopy and three-dimensional image reconstruction," Biophys J. (1991) 60(6):1445-56.

Barouch et al., "A human T-cell leukemia virus type 1 regulatory element enhances the immunogenicity of human immunodeficiency virus type 1 DNA vaccines in mice and nonhuman primates," J Virol. (2005) 79(14):8828-34.

Behrendt et al., "A urokinase receptor-associated protein with specific collagen binding properties"(2000) J Biol Chem 275(3), 1993-2002).

Bode et al., "CpG DNA as a vaccine adjuvant," Expert Rev Vaccines. (2011) 10(4):499-511.

Bradley et al., "Hepatitis A virus: growth characteristics of in vivo and in vitro propagated wild and attenuated virus strains," J Med Virol. (1984) 14(4): 373-86. (Abstract only).

Braun et al., "Immunogenic duplex nucleic acids are nuclease resistant," J Immunol. (1988) 141(6): 2084-9. (Abstract only).

Brito et al., "Self-amplifying mRNA vaccines," Adv Genet. (2015); 89:179-233. (Abstract only).

Cai et al., "Distinct conformational states of SARS-CoV-2 spike protein," Science. (2020) 369(6511): 1586-1592.

Clover Biopharmaceuticals & GSK, "Clover and GSK announce research collaboration to evaluate coronavirus (COVID-19) vaccine candidate with pandemic adjuvant system,", Feb. 24, 2020 (Feb. 24, 2020).

Clover Biopharmaceuticals & GSK, "GlaxoSmithKline and Clover collaborate to evaluate the combination of novel coronavirus vaccine candidate and pandemic vaccine adjuvant system,"Feb. 24, 2020 (Feb. 24, 2020).

Coffman et al., "Vaccine adjuvants: putting innate immunity to work," Immunity. (2010) 33(4):492-503.

De Felipe, "Skipping the co-expression problem: the new 2A "Chysel" technology," Genet Vaccines Ther Sep. 13, 2004;2(1):13.

De Felipe, "Targeting of proteins derived from self-processing polyproteins containing multiple signal sequences," Traffic (2004) 5(8):616-626.

East, L., and Isacke, C. M."The mannose receptor family," (2002) Biochim Biophys Acta 1572(2-3), 364-386.

Emily K Thomas, et al. Endo180 binds to the C-terminal region of type I collagen. J Biol Chem. vol. 280, No. 24, Jun. 17, 2005 (Jun. 17, 2005), pp. 22596-22605.

Gao et al., "Development of an inactivated vaccine candidate for SARS-CoV-2," Science. (2020) 369(6499): 77-81.

Garcon et al., "Development and evaluation of AS03, an Adjuvant System containing a-tocopherol and squalene in an oil-in-water emulsion," Expert Rev Vaccines. (2012) 11(3):349-66.

Geall et al., "Nonviral delivery of self-amplifying RNA vaccines," Proc Natl Acad Sci U S A. (2012) 109(36): 14604-9.

Gil Carmen et al: "COVID-19: Drug Targets and Potential Treatments", Journal of Medicinal Chemistry, vol. 63, No. 21, Jun. 8, 2020 (Jun. 8, 2020), pp. 12359-12386, ISSN: 0022-2623, DOI: 10.1021/acs.jmedchem.Oc00606.

Hagansee et al., "Three-dimensional structure of vaccinia virus-produced human papillomavirus type 1 capsids," J Virol. (1994) 68(7): 4503-5.

Harbury et al., "A switch between two-, three-, and four-stranded coiled coils in GCN4 leucine zipper mutants," Science. (1993) 262(5138):1401-7.

Hutten, A. et al. "New magnetic nanoparticles for biotechnology," (J. Biotech. (2004), 112, 47-63.

Hoppe et al., "A parallel three stranded alpha-helical bundle at the nucleation site of collagen triple-helix formation," FEBS Lett. (1994) 344(2-3): 191-5.

James et al., "Safe administration of the measles vaccine to children allergic to eggs," N Engl J Med. (1995) 332(19):1262-6.

Isacke et al. . "p180, a novel recycling transmembrane glycoprotein with restricted cell type expression," (1990) Mol Cell Biol 10(6), 2606-2618.

Joshua G. Liang et al. "S-Trimer, a COVID-19 subunit vaccine candidate, induces protective immunity in nonhuman primates" Nat Commun., vol. 12, No. 1, Mar. 1, 2021 (Mar. 1, 2021).

Kirchdoerfer et al., "Pre-fusion structure of a human coronavirus spike protein," Nature. (2016) 531(7592): 118-21.

Lanying Du et al: "The spike protein of SARS-COV a target to vaccine and therapeutic development", Nature Reviews Microbiology, vol. 7, No. 3, Mar. 1, 2009 (2009), pp. 226-236, ISSN: 1740-1526, DOI: 10.1038/nrmicro2090.

Latimer et al., "Specificity of monoclonal antibodies produced against phosphorothioate and ribo modified DNAs," Mol Immunol. (1995) 32(14-15): 1057-64. (Abstract only).

Liang et al., "S-Trimer, a COVID-19 subunit vaccine candidate, induces protective immunity in nonhuman primates," Nat Commun. (2021) 12(1):1346.

Liu et al., "Improvement of Pharmacokinetic Profile of TRAIL via Trimer-Tag Enhances its Antitumor Activity in vivo," Sci Rep. (2017) 7(1): 8953.

Ma et al. "Cryo-EM structure of S-Trimer, a subunit vaccine candidate for COVID-19," bioRxiv 2020.09.21.306357. doi:10. 1101/2020.09.21.306357.

Ma et al., "Cryo-EM structure of S-Trimer, a subunit vaccine candidate for COVID-19," J Virol. (2021) 95(11): e00194-21. doi:10.1128/JVI.00194-21.

Magini et al., "Self-Amplifying mRNA Vaccines Expressing Multiple Conserved Influenza Antigens Confer Protection against Homologous and Heterosubtypic Viral Challenge," PLoS One. (2016) 11(8):e0161193.

Mcalinden et al., "Alpha-helical coiled-coil oligomerization domains are almost ubiquitous in the collagen superfamily," J Biol Chem. (2003) 278(43): 42200-42207.

Miroshnikov et al., "Engineering trimeric fibrous proteins based on bacteriophage T4 adhesins," Protein Eng. (1998) 11(4):329-32.

Mohler et al., "Soluble Tumor Necrosis Factor (TNF) Receptors Are Effective Therapeutic Agents in Lethal Endotoxemia and Function

(56) References Cited

OTHER PUBLICATIONS

Simultaneously as Both TNF Carriers and TNF Antagonists," J. of Immunology, vol. 151, No. 3, p. 1548-1561, 1993.

Morel et al., "Adjuvant System AS03 containing a-tocopherol modulates innate immune response and leads to improved adaptive immunity," Vaccine. (2011) 29(13): 2461-73.

Mowat et al., "ISCOMS—a novel strategy for mucosal immunization?," Immunol Today. (1991) 12(11): 383-5. (Abstract only).

Munster et al., "Respiratory disease and virus shedding in rhesus macaques inoculated with SARS-CoV-2," Nature. (2020) 585: 268-272.

Newman et al., "Use of nonionic block copolymers in vaccines and therapeutics," Crit Rev Ther Drug Carrier Syst. (1998);15(2): 89-142. (Abstract only).

O'HAGEN et al., "The history of MF59(®) adjuvant: a phoenix that arose from the ashes," Expert Rev Vaccines. (2013) 12(1): 13-30.

Paracuellos et al. (2015) Structure 23, 2133-2142.

Petsch et al., "Protective efficacy of in vitro synthesized, specific mRNA vaccines against influenza A virus infection," Nat Biotechnol. (2012) 30(12): 1210-6.

Pramanick et al., "Excipient Selection In Parenteral Formulation Development," Pharma Times. (2013) 45: 65-77.

Richmond et al., "Safety and immunogenicity of S-Trimer (SCB-2019), a protein subunit vaccine candidate for COVID-19 in healthy adults: a phase 1, randomised, double-blind, placebo-controlled trial," Lancet. (2021) ;397(10275): 682-694.

Shah et al., "Overview of Vaccine Adjuvants: Introduction, History, and Current Status," Methods Mol Biol. (2017) 1494:1-13. (Abstract only).

Shaw et al., "Heterologous prime-boost COVID-19 vaccination: initial reactogenicity data," Lancet. (2021) 397(10289): 2043-2046.

Stover et al., "New use of BCG for recombinant vaccines," Nature. (1991) 351(6326): 456-60.

Takahashi et al., "Induction of CD8+ cytotoxic T cells by immunization with purified HIV-1 envelope protein in ISCOMs," Nature. (1990) 344(6269): 873-875. (Abstract only).

Thomas et al., "Endo180 Binds to the C-terminal Region of Type I Collagen," J Biol Chem. (2005) 280(24), 22596-22605.

Vatti et al., "Original antigenic sin: A comprehensive review," J Autoimmun. (2017) 83:12-21.

Walls et al., "Structure, Function, and Antigenicity of the SARS-CoV-2 Spike Glycoprotein," Cell. (2020) 181(2): 281-292.e6.

Wu et al., "Characterization of a Novel Member of the Macrophage Mannose Receptor Type C Lectin Family," (1996) J Biol Chem 271(35), 21323-21330.

Wu et al., "Variant SARS-CoV-2 mRNA vaccines confer broad neutralization as primary or booster series in mice," bioRxiv. Oct. 7, 2021;2021.04.13.439482.

Wu et al., "Serum Neutralizing Activity Elicited by mRNA-1273 Vaccine," N Engl J Med. (2021) 384(15): 1468-1470.

Wu et al., "A new coronavirus associated with human respiratory disease in China," Nature. (2020) 579(7798): 265-269.

Zhao Pei, et al. "In vitro Interaction of the Cysteine-rich Domain of Endo180 with the C-terminal Region of Type I Collagen.". Chinese Journal of Biochemistry and Molecular Biology., vol. 31, No. 5, May 31, 2015 (May 31, 2015).

* cited by examiner

MW  Cell medium  Protein A
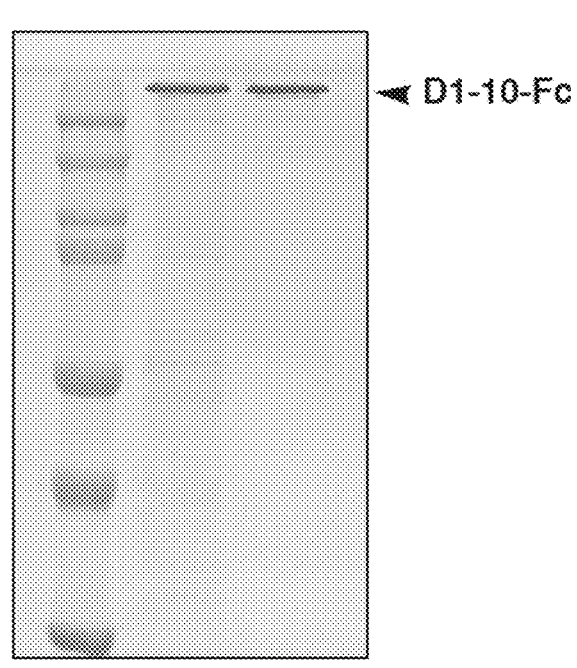
◄ D1-10-Fc
MW  Cell medium  Protein A
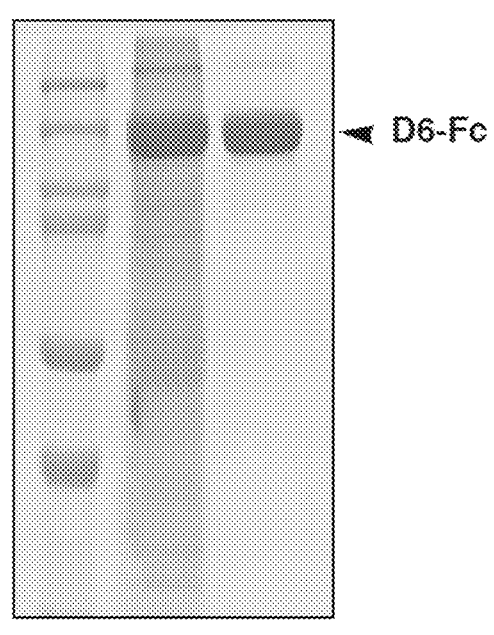
◄ D6-Fc
FIG. 3A                    FIG. 3B

METHODS AND COMPOSITIONS FOR PURIFICATION OF TRIMERIC FUSION PROTEINS

CROSS-REFERENCE TO RELATED APPLICATIONS

This application claims priority to and the benefit of International Patent Application No. PCT/CN2021/087055, filed Apr. 13, 2021, and International Patent Application No. PCT/CN2020/112439, filed Aug. 31, 2020, the disclosures of which applications are incorporated herein by reference in their entireties for all purposes.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: P10892-PCT.210826.Sequence Listing_ST25.txt, date recorded: Aug. 25, 2021, size: 160 KB).

FIELD

The present disclosure relates in some aspects to methods and compositions for affinity purification of proteins containing a C-terminal polypeptide sequence of a procollagen, such as trimeric fusion proteins. Also provided herein are polypeptides, fusion proteins, and recombinant polypeptides containing an ecto-domain of Endo180 or portion thereof capable of reversibly binding a C-terminal polypeptide sequence of a procollagen, e.g., forming a complex with a trimeric fusion protein comprising a C-terminal polypeptide sequence of a procollagen.

BACKGROUND

Many major disease targets exist as membrane-associated trimers and/or require trimerization to become active. Fusion proteins containing a C-terminal polypeptide sequence of a procollagen are capable of spontaneous self-trimerization, allowing for trimerization of protein domains of interest without affecting the native amino acid sequence of the domains or the natural three dimensional trimeric structure. Trimeric fusion proteins containing C-terminal polypeptide sequences of a procollagen may be produced and secreted by cells, resulting in the need to purify the secreted trimeric fusion proteins. Methods of purification that allow for reversible selection of the trimeric fusion protein are therefore needed to isolate the trimeric fusion proteins from other proteins and debris in a sample, e.g., cell culture media. Provided herein are methods, compositions, articles of manufacture, kits, and apparatus that meet such and other needs.

SUMMARY

In some aspects, disclosed herein is a method for purifying a trimeric fusion protein from a sample, comprising contacting a sample comprising a trimeric fusion protein with a soluble Endo180 polypeptide linked to a support. In some embodiments, the trimeric fusion protein comprises a heterologous polypeptide sequence fused to a C-terminal polypeptide sequence of a procollagen. In some embodiments, a first fusion polypeptide comprising the C-terminal polypeptide sequence is capable of forming inter-polypeptide bond(s) (e.g., disulfide bond(s)) with the C-terminal polypeptide sequence of a second fusion polypeptide. In some embodiments, a first, a second, and a third fusion polypeptides each comprising a C-terminal polypeptide sequence of a procollagen are capable of forming inter-polypeptide bond(s) (e.g., disulfide bond(s)) with one another at the C-terminal polypeptide sequence, thereby forming a trimeric fusion protein disclosed herein. In some embodiments, the C-terminal polypeptide sequence derived from a prodomain sequence of a procollagen (e.g., human procollagen) mediates the trimerization of molecules of a fusion polypeptide comprising the C-terminal polypeptide sequence. In some embodiments, the first, second, and third fusion polypeptides are identical in amino acid sequence. In some embodiments, any two or more of the first, second, and third fusion polypeptides can comprise different amino acid sequences. In some embodiments, a fusion polypeptide comprising a C-terminal polypeptide sequence of a procollagen is capable of trimerization via the C-terminal polypeptide sequence. In any of the embodiments herein, the trimeric fusion protein can comprise a heterologous polypeptide sequence fused to a C-terminal polypeptide sequence of a procollagen, and the C-terminal polypeptide sequence is capable of self trimerization and specifically binding to an Endo180 ecto-domain polypeptide. In any of the embodiments herein, the Endo180 ecto-domain polypeptide can be adsorbed, bound, attached, or otherwise immobilized to a support (e.g., a stationary phase in chromatography), whereby the trimeric fusion protein and the Endo180 ecto-domain polypeptide form a complex on the support. In some embodiments, the C-terminal polypeptide sequence is capable of self trimerization and specifically binding to the soluble Endo180 polypeptide, whereby the trimeric fusion protein and the soluble Endo180 polypeptide form a complex on the support. In any of the embodiments herein, the Endo180 ecto-domain polypeptide may lack the Endo180 D1 (CysR) sequence. In any of the embodiments herein, the support can comprise a porous solid (e.g., glass, silica, or alumina) that is packed into a glass or metal tube or that constitutes the walls of an open-tube capillary.

In some embodiments, the Endo180 ecto-domain polypeptide is a soluble Endo180 polypeptide specifically binds to the C-terminal polypeptide sequence in a fusion polypeptide disclosed herein. In some embodiments, the Endo180 ecto-domain polypeptide specifically binds to a trimeric structure formed by the C-terminal polypeptide sequence of a fusion polypeptide or protein. In some embodiments, the trimeric fusion protein and the Endo180 ecto-domain polypeptide form a complex on the support. In some embodiments, the method comprises removing unbound and/or nonspecifically bound molecules from the complex. In some embodiments, the method comprises dissociating the complex to release the trimeric fusion protein, thereby purifying the trimeric fusion protein from the sample. In some embodiments, disclosed herein are compositions and methods for purifying a stabilized trimeric form of a fusion protein comprising a trimerization domain derived from a prodomain sequence of a procollagen (e.g., human procollagen), or a population of trimeric fusion proteins each comprising a different fusion partner fused to the trimerization domain derived from the procollagen prodomain sequence.

In some embodiments, provided herein is a method for purifying a trimeric fusion protein from a sample, comprising: (a) contacting a sample comprising a trimeric fusion protein with a soluble Endo180 polypeptide linked to a support, wherein the trimeric fusion protein comprises a heterologous polypeptide sequence fused to a C-terminal polypeptide sequence of a procollagen, wherein the C-terminal polypeptide sequences form inter-polypeptide bonds (e.g., disulfide bonds), and, wherein the soluble Endo180 polypeptide specifically binds to the C-terminal polypeptide sequence and/or trimer thereof, whereby the trimeric fusion protein and the soluble Endo180 polypeptide form a complex on the support; (b) removing unbound and/or nonspecifically bound molecules from the complex; and (c) dissociating the complex to release the trimeric fusion protein, thereby purifying the trimeric fusion protein from the sample.

In some aspects, disclosed herein is a recombinant polypeptide comprising an Endo180 ecto-domain sequence comprising or consisting of a sequence of Endo180 Domain 6 (D6), a sequence of Endo180 Domain 7 (D7), a sequence of Endo180 Domain 8 (D8), a sequence of Endo180 Domain 9 (D9), and/or a sequence of Endo180 Domain 10 (D10) (e.g., one or more copies of D6, D7, D8, D9, D10, D1-6, D2-6, D3-6, D4-6, D5-6, D1-7, D2-7, D3-7, D4-7, D5-7, D6-7, D1-8, D2-8, D3-8, D4-8, D5-8, D6-8, D7-8, D1-9, D2-9, D3-9, D4-9, D5-9, D6-9, D7-9, D8-9, D1-10, D2-10, D3-10, D4-10, D5-10, D6-10, D7-10, D8-10, and/or D9-10). In some embodiments, the polypeptide lacks an Endo180 D1 sequence, an Endo180 D2 sequence, an Endo180 D3 sequence, an Endo180 D4 sequence, an Endo180 D5 sequence, an Endo180 D7 sequence, an Endo180 D8 sequence, an Endo180 D9 sequence, or an Endo180 D10 sequence, or any combination thereof.

In some aspects, disclosed herein is a recombinant polypeptide comprising an Endo180 ecto-domain sequence comprising or consisting of a sequence of Endo180 Domain 6 (D6), a sequence of Endo180 Domain 7 (D7), a sequence of Endo180 Domain 8 (D8), a sequence of Endo180 Domain 9 (D9), and/or a sequence of Endo180 Domain 10 (D10) (e.g., one or more copies of D6, D7, D8, D9, D10, D1-6, D2-6, D3-6, D4-6, D5-6, D1-7, D2-7, D3-7, D4-7, D5-7, D6-7, D1-8, D2-8, D3-8, D4-8, D5-8, D6-8, D7-8, D1-9, D2-9, D3-9, D4-9, D5-9, D6-9, D7-9, D8-9, D1-10, D2-10, D3-10, D4-10, D5-10, D6-10, D7-10, D8-10, and/or D9-10), wherein the Endo180 ecto-domain sequence is fused to a heterologous polypeptide sequence.

In some aspects, disclosed herein is a recombinant polypeptide comprising a sequence at least 70%, at least 75%, at least 80%, at least 85%, at least 90%, at least 95%, at least 99%, or 100% identical to SEQ ID NO: 1, 2, 3, 4, 43, 44, 45, or 46, or a fragment or variant thereof.

In some aspects, disclosed herein is a complex, comprising: a molecule comprising a heterologous polypeptide sequence linked to a C-terminal polypeptide sequence of a procollagen, and a binding partner comprising an Endo180 ecto-domain sequence comprising or consisting of a sequence of Endo180 Domain 6 (D6), a sequence of Endo180 Domain 7 (D7), a sequence of Endo180 Domain 8 (D8), a sequence of Endo180 Domain 9 (D9), and/or a sequence of Endo180 Domain 10 (D10) (e.g., one or more copies of D6, D7, D8, D9, D10, D1-6, D2-6, D3-6, D4-6, D5-6, D1-7, D2-7, D3-7, D4-7, D5-7, D6-7, D1-8, D2-8, D3-8, D4-8, D5-8, D6-8, D7-8, D1-9, D2-9, D3-9, D4-9, D5-9, D6-9, D7-9, D8-9, D1-10, D2-10, D3-10, D4-10, D5-10, D6-10, D7-10, D8-10, and/or D9-10), wherein all or a portion of the C-terminal polypeptide sequence binds to all or a portion of the Endo180 ecto-domain sequence.

BRIEF DESCRIPTION OF THE DRAWINGS

FIG. 1A shows: a schematic illustration of the 10 structural domains (D1-10) of the extracellular region of Endo180 (left panel); exemplary Endo180 domains fused to an Fc region (fusion proteins: D1-Fc, D1-3-Fc, D1-4-Fc, D1-5-Fc, D1-6-Fc, D1-7-Fc, and D1-10-Fc) separated by non-reducing SDS-PAGE (right upper panel); binding of human placental alkaline phosphatase collagen fusion construct (AP-Coll) to the exemplary Endo180 fusion proteins determined by non-reducing SDS-PAGE (right middle panel) and AP as a negative control (right lower panel). FIG. 1B shows AP binding activity to the exemplary Endo180 fusion proteins quantified by optical density (OD405).

FIG. 2A shows binding activity of a human placental alkaline phosphatase collagen fusion construct (AP-Coll) to exemplary Endo180 fusion proteins (D6-Fc and D1-10-Fc) determined by non-reducing SDS-PAGE. AP alone served as a negative control. FIG. 2B shows the binding activity of AP alone and AP-Coll to the exemplary Endo180 fusion proteins quantified by optical density (OD405).

FIGS. 3A-3B show high levels SDS-PAGE analysis of expression and Protein A affinity purification of exemplary Endo180 D1-10-Fc fusion proteins (FIG. 3A) and exemplary Endo180 D6-Fc fusion proteins (FIG. 3B) using MAb-Select SuRe Protein A resins (GE BioSciences). The Endo180-Fc fusion proteins were expressed as secreted proteins in serum-free culture. After binding to the Protein A resin, the Endo180-Fc fusion proteins were eluted with acetic acid buffer (pH 3.5).

FIG. 5A shows purification of the exemplary trimeric fusion protein via exemplary D1-10-Fc (SEQ ID NO: 2) fusion proteins non-covalently bound to Protein A Sepharose resins. FIG. 5B shows purification of the exemplary trimeric fusion protein via exemplary D6-Fc fusion proteins non-covalently bound to Protein A Sepharose resins. FIGS. 5C and 5D show the purity of the partially cleaved S-Trimer™ fusion protein at the S1/S2 boundary by furin protease purified from either the exemplary D1-10-Fc or D6-Fc affinity tag, respectively, analyzed by Size-exclusion SEC-HPLC. For both exemplary purifications, the S-Trimer™ was expressed in GH-CHO cells as a secreted protein, and the serum-free cell culture medium containing the S-Trimer™ was loaded onto Protein A Sepharose resins pre-captured either with D6-Fc or D1-10-Fc to the column via the high-affinity interaction between Protein A and Fc. After washing off any unbound contaminating proteins, the bound S-Trimer™ was purified to near homogeneity in a single step using 0.5 M-1.0 M NaCl in phosphate buffered saline as elution buffer, and analyzed by SDS-PAGE as indicated.

Figure 6:
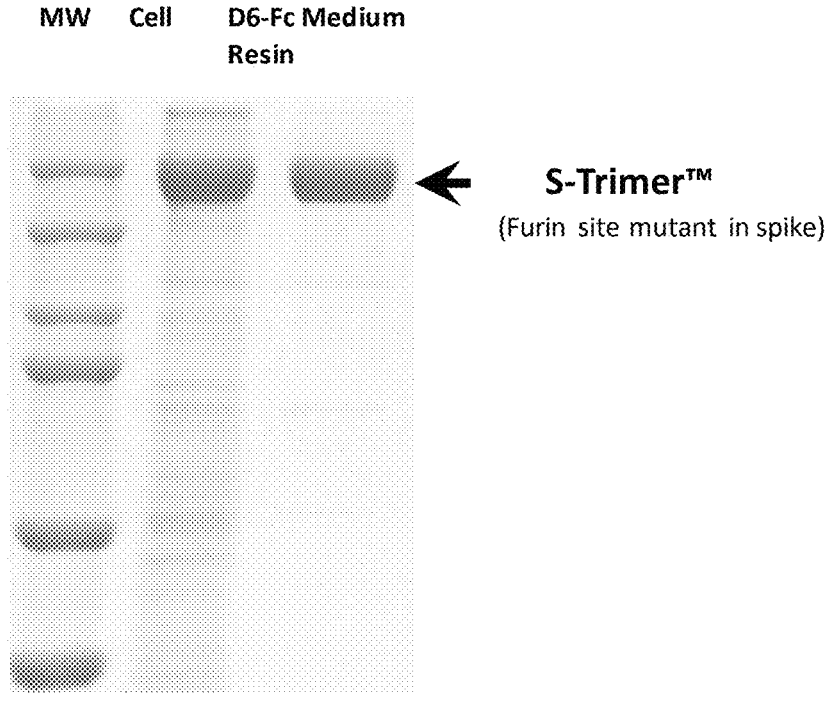

FIG. 6 shows SDS-PAGE analysis of purification of another exemplary trimeric fusion protein (a SARS-Cov-2 Spike protein antigen with furin cleavage site mutation) via exemplary D6-Fc fusion protein non-covalently bound to Protein A Sepharose resins. This another exemplary S-Trimer™ fusion protein was expressed in GH-CHO cells as a secreted protein, and the serum-free cell culture medium containing S-Trimer™ was loaded onto Protein A Sepharose resins with D6-Fc pre-captured to the column via the high-affinity interaction between Protein A and Fc. After washing off any unbound contaminating proteins, the bound furin site mutant S-Trimer™ was purified to near homogeneity in a single step using 0.5 M-1.0 M NaCl in phosphate buffered saline, and analyzed by SDS-PAGE as indicated. Note, in comparison with that of native S-Trimer™, the purified furin site mutant from of S-Trimer™ did not show any S1 subunit cleaved.

DETAILED DESCRIPTION

Provided herein are methods for purifying proteins containing procollagen, such as a C-terminal polypeptide sequence of a procollagen. In some aspects, the purification methods described herein are affinity purification techniques, where compositions capable of reversibly binding to a C-terminal polypeptide sequence of a procollagen are utilized. In some embodiments, the reversible binding or complexing of the composition with the C-terminal polypeptide sequence of a procollagen allows for the selection and purification of proteins containing a C-terminal polypeptide sequence of a procollagen from samples. In some embodiments, the composition is or includes an Endo180 polypeptide capable of reversibly binding to a C-terminal polypeptide sequence of a procollagen.

Endo180 is a collagen binding protein that was discovered independently by three different groups. The Endo180 protein was originally identified as an antigen that could bind to four different monoclonal antibodies that had been raised to identify novel human fibroblast cell surface receptors, and was shown to be a constitutively recycling cell surface protein (Isacke et al. (1990) Mol Cell Biol 10(6), 2606-2618). Endo180 also was found to form a trimolecular cell surface complex with urokinase plasminogen activator (uPA) and its receptor (uPAR) through chemical cross-linking studies and thus also is named urokinase plasminogen activator receptor associated protein (uPARAP) (Behrendt et al., (2000) J Biol Chem 275(3), 1993-2002).

A third group discovered that Endo180 encoded a novel macrophage mannose receptor type C lectin that was present in an EST database (Wu et al., (1996) J Biol Chem 271(35), 21323-21330). This cell surface protein has been identified as the fourth member of the mannose receptor family, which is also composed of the macrophage mannose receptor, the M-type phospholipase $A_2$ receptor, and DEC-205. The four receptors are all type I transmembrane proteins with a highly conserved structure composed of an N-terminal cysteine-rich or ricin-type domain, a fibronectin type II domain (FNII), 8 or 10 C-type lectin-like domains (CTLDs), a single transmembrane domain, and a short cytoplasmic domain (East, L., and Isacke, C. M. (2002) Biochim Biophys Acta 1572(2-3), 364-386).

Endo180 has been shown to act as a collagen receptor by binding to gelatin, type I, type II, type IV, and type V collagens, and also mediates endocytosis and turnover of these extracellular matrix proteins. The FNII domain of Endo180 (which shares a highly conserved sequence with other collagen binding FNII domains, such as fibronectin, MMP-2, and MMP-9) appears to be required for binding to these collagens. It has been shown that mature native type I collagen binds to the first 4 domains of Endo180 (Paracuellos et al. (2015) Structure 23, 2133-2142). The region of collagen to which Endo180 binds has not been previously defined, due to the use of mature native collagens which lack any prodomains from tissue sources.

It has also been shown that Endo180 binds to a defined sequence of α1(I) collagen C-terminal region of collagen that includes C-prodomain (amino acids 1000-1453) (Thomas et al., J Biol Chem. (2005) 280(24), 22596-22605). To determine whether the α1(I) collagen C-terminal glycine repeat region or the C-prodomain alone were capable of initiating this binding, human placental secreted alkaline phosphatase (AP)-Tag technology was used to develop AP-Gly (amino acids 1000-1189) and AP-Pro (amino acids 1206-1453) fusion proteins, respectively (Thomas et al., J Biol Chem. (2005) 280(24), 22596-22605). However, these fusion proteins exhibited little binding to the surface of Rat-1 and Rat-1(Ras) cells compared to a human placental alkaline phosphatase collagen fusion construct (AP-Coll) containing the C-terminal glycine repeat region and prodomain of rat col1a1 (accession number Z78279). Although AP-Pro could form a trimeric structure, little binding was detected, suggesting that binding of Endo180 to soluble α1(I) collagen may require both a glycine repeat region and the C-prodomain or portions thereof.

The interaction between various collagen types and Endo180 appears to play a role in the cell-matrix adhesion, as Endo180-deficient cells have a 50% reduction in adhesion to type V collagen and also a reduced ability to bind to purified types I and IV collagen. To investigate whether the C-terminal glycine repeat region and C-prodomain of α1(I) collagen mediate this adhesion to Endo180, competition binding experiments were performed, and the results demonstrated that AP-Coll was able to significantly inhibit the adhesion of Rat-1 and Rat-1(Ras) cells specifically to type I collagen, suggesting that this region of collagen facilitates adhesion of cells to the extracellular matrix (Thomas et al., J Biol Chem. (2005) 280(24), 22596-22605).

Endo180 is a large type I transmembrane protein composed of 10 distinct structural domains that consist of an extracellular N-terminal cysteine-rich domain, a fibronectin type II domain (FNII), 8 consecutive C-type lectin-like domains (CTLDs), a single transmembrane domain, and a short cytoplasmic domain. To identify which structural domain(s) of Endo180 is involved in binding to C-terminal region of α1(I) collagen, structure-functional studies of its collagen binding site via serial deletions of Endo180 domains (D1-D10) were conducted as described in Examples 1-4 below. Domain 6 (D6) of the Endo180 ecto-domain, which is the 4th CTLD, was capable of procollagen binding (see, e.g., Example 2).

Examples 1 and 2 demonstrate the ability of the complete ecto-domain of Endo180 containing domains D1-10 or the D6 domain alone when fused to human IgG Fc could bind to a human placental alkaline phosphatase collagen fusion construct (AP-Coll) containing a C-terminal glycine repeat region and prodomain of rat col1α1 (accession number Z78279), and other recombinant proteins fused to the C-terminal glycine repeat region and prodomain of collagen, all with high affinity. Furthermore, as demonstrated in Examples 3 and 4, such binding affinity can be completely disrupted under moderate to high salt conditions.

Thus, in some aspects, the methods provided herein harness the discovery that the ecto-domain of Endo180, and specific domains thereof, bind to or complex with a C-prodomain of procollagen and a glycine repeat sequence of procollagen, e.g., as contained in a C-terminal polypeptide sequence of a procollagen, to create an affinity purification method capable of efficiently purifying proteins containing a C-terminal polypeptide sequence of a procollagen, including fusion proteins and recombinant proteins containing such sequences (Liu et al., (2017) Sci Rep. 7(1):8953).

In some embodiments, the methods provided herein include the use of Endo180 polypeptides, such as described in Section I-A, as affinity molecules or tags capable of complexing with, e.g., binding to, a C-terminal polypeptide sequence of a procollagen. The methods described herein are contemplated as useful for purifying any protein that contains procollagen, such as a C-terminal polypeptide sequence of a procollagen, including trimeric protein structures formed by C-terminal polypeptide sequences of procollagen. In some embodiments, the C-terminal polypeptide sequence of a procollagen, which includes the a C-prodomain of procollagen and a glycine repeat sequence of procollagen, to which the Endo180 polypeptide complexes is contained in a protein such as a fusion protein or recombinant polypeptide. In some embodiments, the fusion protein is a trimeric fusion protein, for example as described in Section II. In some embodiments, the trimeric fusion protein is a biologic drug.

Trimeric fusion proteins are of particular interest in treating diseases because many major disease targets exist as membrane-associated trimers and/or require trimerization to become active. Non-limiting examples of trimerization-dependent targets include the tumor necrosis factor (TNF) superfamily, which is involved in extrinsic apoptosis, immune co-stimulation, and inflammation, and enveloped RNA virus antigens responsible for entry into host cells. Fusion proteins containing C-terminal polypeptide sequences of a procollagen, which can include the C-prodomain of procollagen and a glycine repeat sequence of procollagen, are capable of spontaneous self-trimerization, allowing for trimerization of protein domains of interest without affecting the native amino acid sequence of the domains or the natural three dimensional trimeric structure formed by the native protein domains. Production of fusion proteins containing C-terminal polypeptide sequences of a procollagen to generate trimeric fusion proteins may be accomplished in vitro, for example by using cells to produce and secrete the trimeric fusion proteins into the cell culture media. Thus, the methods provided herein are particularly well-suited to purifying trimeric fusion proteins produced according to such methods.

In some aspects, the methods of purification provided herein utilize Endo180 polypeptides as described herein isolate proteins containing a C-terminal polypeptide sequence of a procollagen, e.g., trimeric fusion proteins, from samples containing mixtures of proteins and/or other molecules. In some embodiments, the sample is a biological sample. In some embodiments, the sample is a culture medium.

In some embodiments, proteins containing a C-terminal polypeptide sequence of a procollagen, e.g., trimeric fusion proteins, are purified from a sample by contacting the sample with an Endo180 polypeptide. In this way, the C-terminal polypeptide sequence of a procollagen can form a complex with the Endo180 polypeptide. In some embodiments, the Endo180 polypeptide is coupled to a support. Thus, in some cases, proteins containing a C-terminal polypeptide sequence of a procollagen, e.g., trimeric fusion proteins, are immobilized to a support via the Endo180 polypeptide. In some embodiments, immobilization of the proteins on the support allows unbound and/or nonspecifically bound molecules, e.g., from a mixed sample, to be separated from the protein of interest.

In some embodiments, the Endo180 polypeptide is covalently linked to a support, e.g., a solid support. In some embodiments, the Endo180 polypeptide is non-covalently linked to a support, e.g., a solid support. In some cases, the Endo180 polypeptide is a fusion protein including an affinity tag capable of non-covalently binding to a support, e.g., a solid support, having a cognate binding partner, e.g., receptor, of the affinity tag immobilized thereon. Thus, an Endo180 fusion protein containing an affinity tag can be loaded onto a support functionalized with the appropriate binding partner.

In some embodiments, the methods provided herein allow for efficient purification of proteins containing a C-terminal polypeptide sequence of a procollagen, e.g., trimeric fusion proteins, because the complex formed (e.g., bond) between the C-terminal polypeptide sequence of a procollagen of the protein and the Endo180 polypeptide is reversible. For example, in some embodiments, the complex can be dissociated in a single step by applying a buffer having a salt concentration to the support. Thus, in some embodiments, after removal of unbound proteins, molecules, and debris, the complex, e.g., binding, between the Endo180 polypeptide and the C-terminal polypeptide sequence of a procollagen, is dissociated, thereby releasing the isolated proteins from the support and resulting in a protein purified from the sample.

In some embodiments, dissociation of the complex takes place in a single step. In some embodiments, the dissociation is accomplished by addition of a buffer to the support. In some embodiments, the dissociation is accomplished by addition of a buffer containing a mild salt concentration to the solid support. In some embodiments, the dissociation is accomplished by addition of a buffer containing a moderate salt concentration to the solid support. In some embodiments, the dissociation is accomplished by addition of a buffer containing a high salt concentration to the solid support. In some embodiments, the salt concentration is between or between about 0.5 M-1.0 M. In some embodiments, the salt is NaCl.

The methods described herein provide an efficient and effective means of purifying proteins of interest containing a C-terminal polypeptide sequence of a procollagen. In some embodiments, the single step reversibility of complex formation between the C-terminal polypeptide sequence of a procollagen and the Endo180 polypeptide provides an ideal method for quickly purifying proteins, such as biologic drugs (e.g., trimeric fusion proteins), produced in vitro.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference. The section headings used herein are for organizational purposes only and are not to be construed as limiting the subject matter described.

I. Methods for Affinity Purification

The methods provided herein allow for affinity purification of proteins containing a C-terminal polypeptide sequence of a procollagen. In some embodiments, the affinity purification methods are accomplished using an Endo180 polypeptide, for example as described in Section I-A below, capable of binding to a C-terminal polypeptide sequence of a procollagen.

In some embodiments, the Endo180 polypeptide forms a reversible complex with, e.g., binds to, a C-terminal polypeptide sequence of procollagen which includes a C-prodomain of a procollagen and a glycine repeat sequence of a procollagen or portions thereof. Thus, in some embodiments, the methods allow for selection and isolation of proteins of interest containing a C-terminal polypeptide sequence of procollagen from a sample, e.g., a mixed sample, and elution and collection of the protein of interest of by dissociating the complex.

In some embodiments, the Endo180 polypeptide is linked to a support, for example a support described in Section I-B. In some embodiments, the Endo180 polypeptide is linked to a solid support. In some embodiments, the support is a resin, a particle, a bead, a solid substrate, a membrane, or a combination thereof. Thus, in some cases, the protein of interest containing the C-terminal polypeptide sequence of a procollagen is immobilized on the support via the Endo180 polypeptide. In some embodiments, immobilization of the protein of interest on the support allows for the protein of interest to be separated from other proteins and/or debris. In some embodiments, unbound and/or nonspecifically bound molecules are removed from the complex using a wash step. In some embodiments, one or more wash steps may be used to remove unbound or nonspecifically bound molecules from the support. In some embodiments, the wash step(s) involves introducing a buffer to the support.

In some embodiments, the complex formed between the immobilized protein and the Endo180 polypeptide is dissociated by addition of a buffer. In some embodiments, the buffer contains a salt concentration capable of dissociating the complex, e.g., bond, formed between the C-terminal polypeptide sequence of a procollagen contained in the protein of interest and the Endo180 polypeptide. In some embodiments, the buffer contains a salt concentration between or between about 0.1 M to about 1.5 M, about 0.1 M to about 1.4 M, about 0.1 M to about 1.3 M, about 0.1 M to about 1.2 M, about 0.1 M to about 1.1 M, about 0.1 M to about 1.0 M, about 0.1 M to about 0.9 M, about 0.1 M to about 0.8 M, about 0.1 M to about 0.7 M, about 0.1 M to about 0.6 M, about 0.1 M to about 0.5 M, about 0.1 M to about 0.4 M, about 0.1 M to about 0.3 M, about 0.1 M to about 0.2 M, about 0.2 M to about 1.5 M, about 0.3 M to about 1.5 M, about 0.4 M to about 1.5 M, about 0.4 M to about 1.5 M, about 0.5 M to about 1.5 M, about 0.6 M to about 1.5 M, about 0.7 M to about 1.5 M, about 0.8 M to about 1.5 M, about 0.9 M to about 1.5 M, about 1.0 M to about 1.5 M, about 1.1 M to about 1.5 M, about 1.2 M to about 1.5 M, about 1.3 M to about 1.5 M, or about 1.4 M to about 1.5 M, inclusive. In some embodiments, the salt concentration is between or between about 0.5 M to about 1.0 M, inclusive. In some embodiments, the salt is NaCl.

In some embodiments, the complex between the immobilized protein and the Endo180 polypeptide is dissociated in a single step, e.g., by addition of buffer once to the support. In some embodiments, the complex between the immobilized protein and the Endo180 polypeptide is dissociated in two or more steps, e.g., including multiple additions of buffer to the support. In some embodiments, for example when two or more steps are used for dissociating the complex, one or more buffers with differing salt concentrations are used to dissociate the complex. In some embodiments, a plurality of buffers having increasing salt concentrations are used in a plurality of steps to dissociate the complex.

In some embodiments, dissociating the complex formed between the immobilized protein and the Endo180 polypeptide frees the protein of interest from the support, allowing elution of the purified protein of interest. In some embodiments, the protein of interest is collected, e.g., in a container (see, e.g., Section III). In some embodiments, the eluted protein of interest is further processed. For example, in some embodiments, if the purified protein of interest is a therapeutic, e.g., biologic, the protein can be formulated for administration, e.g., formulated as a pharmaceutical composition.

In some embodiments, the protein of interest is a trimeric fusion protein containing a C-terminal polypeptide sequence of a procollagen. In some embodiments, the trimeric fusion protein includes a heterologous polypeptide sequence fused to a C-terminal polypeptide sequence of a procollagen. In some embodiments, the C-terminal polypeptide sequence is capable of self trimerization, thereby generating the trimeric fusion protein.

Many major disease targets exist as membrane-associated trimers and/or require trimerization to become active. Fusion proteins containing a C-terminal polypeptide sequence of a procollagen are capable of spontaneous self-trimerization through the C-terminal polypeptide sequence of a procollagen, which allows for trimerization of protein of interest without affecting the native amino acid sequence of the domains. Production of such trimeric fusion proteins may be accomplished in vitro, for example by infecting cells with polynucleotides encoding fusion proteins, which once expressed trimerize to form trimeric fusion proteins that can be secreted from the cell. Such production necessitates purification of the secreted trimeric fusion proteins from the cell culture media. The methods of purification provided herein are suitable for purification of trimeric fusion proteins, such as described in Section II.

A. Endo180 Polypeptides

The methods described herein include the use of Endo180 polypeptides, e.g., one or more Endo180 ecto-domain polypeptide, such as polypeptide comprising or consisting of all or a portion of the Endo180 Domain 6 (D6) sequence. In some embodiments, the Endo180 ecto-domain polypeptide comprises an Endo180 ecto-domain sequence comprising or consisting of a sequence of Endo180 Domain 6 (D6), a sequence of Endo180 Domain 7 (D7), a sequence of Endo180 Domain 8 (D8), a sequence of Endo180 Domain 9 (D9), and/or a sequence of Endo180 Domain 10 (D10). In some embodiments, the Endo180 ecto-domain polypeptide comprises an Endo180 ecto-domain sequence comprising or consisting of one or more copies of D6, D7, D8, D9, D10, D1-6, D2-6, D3-6, D4-6, D5-6, D1-7, D2-7, D3-7, D4-7, D5-7, D6-7, D1-8, D2-8, D3-8, D4-8, D5-8, D6-8, D7-8, D1-9, D2-9, D3-9, D4-9, D5-9, D6-9, D7-9, D8-9, D1-10, D2-10, D3-10, D4-10, D5-10, D6-10, D7-10, D8-10, and/or D9-10, or a fragment or variant thereof.

In some aspects, the Endo180 polypeptides described herein are capable of complexing, e.g., binding, to a C-terminal polypeptide sequence of a procollagen. In some embodiments, the Endo180 polypeptide provided herein is mammalian, optionally human. The term Endo180 polypeptide as used herein refers to any Endo180 polypeptide, Endo180 fusion protein, Endo180 recombinant polypeptide, Endo180 containing binding partner, or Endo180 containing binding reagent described herein, unless otherwise stated.

In some embodiments, the Endo180 polypeptide is soluble. For example, in some cases, the Endo180 polypeptide does not include a transmembrane domain and/or a cytoplasmic domain. In some embodiments, the soluble Endo180 polypeptide is or includes an ecto-domain of an Endo180 protein. In some embodiments, the Endo180 ecto-domain is or includes the sequence set forth in SEQ ID NO: 7. In some embodiments, the Endo180 ecto-domain is or includes a sequence with at least 75%, 80%, 85%, 90%, 91%, 92%, 93%, 94%, 95%, 96%, 97%, 98%, or 99% sequence identity with the sequence set forth in SEQ ID NO: 7. In some embodiments, the soluble Endo180 polypeptide is or includes one or more domains contained in the Endo180 ecto-domain.

The ecto-domain of Endo180 is composed of 10 distinct structural domains that consist of an extracellular N-terminal cysteine-rich domain, referred to herein as D1; a fibronectin type II domain (FNII), referred to herein as D2; and 8 consecutive C-type lectin-like domains (CTLDs), referred to herein as D1-D8, respectively. In some embodiments, the sequences of D1-D10 are or include the sequence set forth in SEQ ID NOS: 8-17, respectively. In some embodiments, the sequences of D1-D10 are or include a sequence with at least 75%, 80%, 85%, 90%, 91%, 92%, 93%, 94%, 95%, 96%, 97%, 98%, or 99% sequence identity with the sequences set forth in SEQ ID NOS: 8-17, respectively.

In some embodiments, the soluble Endo180 polypeptide includes domains 1-10 (D1-10) of Endo180. In some embodiments, the soluble Endo180 polypeptide includes domains 6-10 (D6-10) of Endo180. In some embodiments, the soluble Endo180 polypeptide includes domains 6-9 (D6-9) of Endo180. In some embodiments, the soluble Endo180 polypeptide includes domains 6-8 (D6-8) of Endo180. In some embodiments, the soluble Endo180 polypeptide includes domains 6-7 (D6-7) of Endo180. In some embodiments, the soluble Endo180 polypeptide includes domains 6-10 (D6-10) of Endo180. In some embodiments, the soluble Endo180 polypeptide incudes domain 6 (D6) of Endo180.

In some embodiments, the soluble Endo180 polypeptide incudes two or more domain 6 (D6) of Endo180. In some embodiments, the soluble Endo180 polypeptide incudes two or more consecutive domain 6 (D6) of Endo180. In some embodiments, the soluble Endo180 polypeptide incudes three domain 6 (D6) of Endo180.

In some embodiments, the soluble Endo180 polypeptide does not include any one or more of domains 1-5 (D1-5) of Endo180. In some embodiments, the soluble Endo180 polypeptide does not include any one or more of domains 1-4 (D1-4) of Endo180.

In some embodiments, the soluble Endo180 polypeptide includes domains 1-6 (D1-6) of Endo180. In some embodiments, the soluble Endo180 polypeptide includes domains 2-6 (D2-6) of Endo180. In some embodiments, the soluble Endo180 polypeptide includes domains 3-6 (D3-6) of Endo180. In some embodiments, the soluble Endo180 polypeptide includes domains 4-6 (D4-6) of Endo180. In some embodiments, the soluble Endo180 polypeptide includes domains 5-6 (D5-6) of Endo180.

In some embodiments, the soluble Endo180 polypeptide is a fusion protein. In some embodiments, the Endo180 fusion protein includes a heterologous polypeptide which may include any polypeptide that is not Endo180 or a fragment or variant thereof.

In some embodiments, the heterologous polypeptide sequence includes a tag, such as a tag for affinity purification. For example, in some cases, the Endo180 polypeptide is linked to a support, such as a solid support, such that the complexing between the C-terminal polypeptide sequence of a procollagen contained in the protein of interest the Endo180 polypeptide results in the immobilization of the protein of interest on the support. In some cases, the Endo180 polypeptide is linked directly to the support, e.g., via a covalent linkage. Alternatively, for example when the Endo180 polypeptide is a fusion protein, the Endo180 polypeptide is linked to the support non-covalently, optionally through binding of an affinity tag contained in the Endo180 fusion protein to a cognate binding partner immobilized on the support. In some embodiments, when the Endo180 polypeptide is linked to a support, the Endo180 polypeptide is no longer considered soluble.

It is contemplated that any suitable affinity tag may be included in the Endo180 fusion protein. In some embodiments, the affinity tag included in the Endo180 fusion protein is biotin. In some embodiments, the biotin binds to streptavidin immobilized on the support. In some embodiments, the biotin binds to avidin immobilized on the support.

In some embodiments, the affinity tag included in the Endo180 fusion protein is an Fc region. In some embodiments, the soluble Endo180 is an Endo180-Fc fusion protein. In some embodiments, the Fc region is a human Fc region. In some embodiments, the Fc region is an IgG Fc region. In some embodiments, the Fc region is or includes the sequence set forth by SEQ ID NO: 6 or SEQ ID NO: 42. In some embodiments, the Fc region is or includes a sequence at least 70%, at least 75%, at least 80%, at least 85%, at least 90%, at least 95%, at least 99%, or 100% identical to SEQ ID NO: 6 or SEQ ID NO: 42. In some embodiments, the Fc region binds non-covalently to Protein A immobilized on a support. In some embodiments, the support is a Protein A resin. In some embodiments, the Protein A resin is Sepharose.

In some embodiment, the soluble Endo180 polypeptide is a D1-10-Fc fusion protein. In some embodiments, the soluble Endo180 polypeptide includes a sequence at least 70%, at least 75%, at least 80%, at least 85%, at least 90%, at least 95%, at least 99%, or 100% identical to SEQ ID NO: 1 or SEQ ID NO: 2, or a fragment or variant thereof. In some embodiments, the soluble Endo180 polypeptide includes a sequence at least 70%, at least 75%, at least 80%, at least 85%, at least 90%, at least 95%, at least 99%, or 100% identical to SEQ ID NO: 43 or SEQ ID NO: 44, or a fragment or variant thereof.

In some embodiments, the soluble Endo180 polypeptide is a D6-10-Fc fusion protein. In some embodiments, the soluble Endo180 polypeptide is a D6-9-Fc fusion protein. In some embodiments, the soluble Endo180 polypeptide is a D6-8-Fc fusion protein. In some embodiments, the soluble Endo180 polypeptide is a D6-7-Fc fusion protein.

In some embodiments, the soluble Endo180 polypeptide is a D6-Fc fusion protein. In some embodiments, the soluble Endo180 polypeptide comprises a sequence at least 70%, at least 75%, at least 80%, at least 85%, at least 90%, at least 95%, at least 99%, or 100% identical to SEQ ID NO: 3 or SEQ ID NO: 4, or a fragment or variant thereof. In some embodiments, the soluble Endo180 polypeptide comprises a sequence at least 70%, at least 75%, at least 80%, at least 85%, at least 90%, at least 95%, at least 99%, or 100% identical to SEQ ID NO: 45 or SEQ ID NO: 46, or a fragment or variant thereof.

In some embodiments, the soluble Endo180 polypeptide is a (D6)$_2$-Fc fusion protein. In some embodiments, the soluble Endo180 polypeptide is a (D6)$_3$-Fc fusion protein. In some embodiments, the soluble Endo180 polypeptide is a (D6)$_n$-Fc fusion protein, wherein n is an integer of 4, 5, 6, 7, 8, 9, 10, or more. In some embodiments, the soluble Endo180 polypeptide is a D1-6-Fc fusion protein. In some embodiments, the soluble Endo180 polypeptide is a D2-6-Fc fusion protein. In some embodiments, the soluble Endo180 polypeptide is a D3-6-Fc fusion protein. In some embodiments, the soluble Endo180 polypeptide is a D4-6-Fc fusion protein. In some embodiments, the soluble Endo180 polypeptide is a D5-6-Fc fusion protein.

In some embodiments, the Endo180 polypeptide is contained in a binding reagent. In some embodiments, the binding reagent includes an Endo180 ecto-domain sequence including an Endo180 Domain 6 (D6) sequence that is capable of complexing with a target molecule including a C-terminal polypeptide sequence of a procollagen, wherein the complex is formed between all or a portion of the C-terminal polypeptide sequence and all or a portion of the Endo180 Domain 6 (D6) sequence. In some embodiments, the binding reagent lacks any one or more of Endo180 D1, D2, D3, D4, D5, D7, D8, D9, and D10. In some embodiments, the binding reagent lacks an Endo180 Domain 1 (D1) sequence. In some embodiments, the binding reagent lacks an Endo180 Domain 2 (D2) sequence. In some embodiments, the binding reagent lacks an Endo180 Domain 3 (D3) sequence. In some embodiments, the binding reagent lacks an Endo180 Domain 4 (D4) sequence. In some embodiments, the binding reagent lacks an Endo180 Domain 5 (D5) sequence. In some embodiments, the binding reagent lacks an Endo180 Domain 7 (D7) sequence. In some embodiments, the binding reagent lacks an Endo180 Domain 8 (D8) sequence. In some embodiments, the binding reagent lacks an Endo180 Domain 9 (D9) sequence. In some embodiments, the binding reagent lacks an Endo180 Domain 10 (D10) sequence.

In some embodiments, the binding reagent includes a fusion polypeptide containing Endo180 Domains 1-6 (D1-6), D2-6, D3-6, D4-6, D5-6, one or more D6, D6-7, D6-8, D6-9, or D6-10, or a combination thereof. In some embodiments, the binding reagent includes two or more D6. In some embodiments, the binding reagent includes two or more consecutive D6.

In any of the embodiments herein, the binding reagent can comprise an Endo180 ecto-domain sequence comprising or consisting of a sequence of Endo180 Domain 6 (D6), a sequence of Endo180 Domain 7 (D7), a sequence of Endo180 Domain 8 (D8), a sequence of Endo180 Domain 9 (D9), and/or a sequence of Endo180 Domain 10 (D10). In any of the embodiments herein, the binding reagent can comprise an Endo180 ecto-domain sequence comprising or consisting of one or more copies of D6, D7, D8, D9, D10, D1-6, D2-6, D3-6, D4-6, D5-6, D1-7, D2-7, D3-7, D4-7, D5-7, D6-7, D1-8, D2-8, D3-8, D4-8, D5-8, D6-8, D7-8, D1-9, D2-9, D3-9, D4-9, D5-9, D6-9, D7-9, D8-9, D1-10, D2-10, D3-10, D4-10, D5-10, D6-10, D7-10, D8-10, and/or D9-10, in any suitable combination.

In some embodiments, the binding reagent is soluble. In some embodiments, the binding reagent is linked to a support, for examples as described in Section I-B. In some embodiments, the binding reagent is covalently linked to the support. In some embodiments, the bind reagent is non-covalently linked to the support. For example, when the binding reagent includes a fusion protein, the fusion protein may contain an affinity tag, such as described herein, which facilitates non-covalent binding between the binding reagent and a cognate binding partner immobilized on the support.

In some embodiments, the Endo180 polypeptide is a recombinant polypeptide. In some embodiments, the recombinant polypeptide includes an Endo180 Domain 6 (D6) sequence, and the recombinant polypeptide lacks an Endo180 D1 sequence, an Endo180 D2 sequence, an Endo180 D3 sequence, an Endo180 D4 sequence, an Endo180 D5 sequence, an Endo180 D7 sequence, an Endo180 D8 sequence, an Endo180 D9 sequence, or an Endo180 D10 sequence, or any combination thereof. In some embodiments, the recombinant polypeptide lacks one or more of Endo180 D1, D2, D3, D4, D5, D7, D8, D9, and D10. In some embodiments, the recombinant polypeptide consists of Endo180 Domains 1-6 (D1-6), D2-6, D3-6, D4-6, D5-6, one or more D6, D6-7, D6-8, D6-9, or D6-10, or a combination thereof. In some embodiments, the recombinant polypeptide consists of Endo180 Domains 1-7 (D1-7), D2-7, D3-7, D4-7, D5-7, one or more D6, D6-7, D6-8, D6-9, or D6-10, or a combination thereof. In some embodiments, the recombinant polypeptide consists of Endo180 Domains 1-8 (D1-8), D2-8, D3-8, D4-8, D5-8, one or more D6, D6-7, D6-8, D6-9, or D6-10, or a combination thereof. In some embodiments, the recombinant polypeptide consists of Endo180 Domains 1-9 (D1-9), D2-9, D3-9, D4-9, D5-9, one or more D6, D6-7, D6-8, D6-9, or D6-10, or a combination thereof. In some embodiments, the recombinant polypeptide consists of Endo180 Domains 1-10 (D1-10), D2-10, D3-10, D4-10, D5-10, one or more D6, D6-7, D6-8, D6-9, or D6-10, or a combination thereof. In some embodiments, the recombinant polypeptide includes two or more D6. In some embodiments, the recombinant polypeptide includes two or more consecutive D6.

In some embodiments, provided herein is a polypeptide or complex thereof comprising an Endo180 Domain 6 (D6) moiety and a moiety of interest, and the polypeptide or complex lacks an Endo180 D1 sequence, an Endo180 D2 sequence, an Endo180 D3 sequence, an Endo180 D4 sequence, an Endo180 D5 sequence, an Endo180 D7 sequence, an Endo180 D8 sequence, an Endo180 D9 sequence, or an Endo180 D10 sequence, or any combination thereof. In some embodiments, the polypeptide or complex lacks one or more of Endo180 D1, D2, D3, D4, D5, D7, D8, D9, and D10. In some embodiments, the polypeptide or complex comprises Endo180 Domains 1-6 (D1-6), D2-6, D3-6, D4-6, D5-6, one or more D6, D6-7, D6-8, D6-9, or D6-10, or a combination thereof, and a moiety of interest. In some embodiments, the polypeptide or complex comprises Endo180 Domains 1-7 (D1-7), D2-7, D3-7, D4-7, D5-7, one or more D6, D6-7, D6-8, D6-9, or D6-10, or a combination thereof, and a moiety of interest. In some embodiments, the polypeptide or complex comprises Endo180 Domains 1-8 (D1-8), D2-8, D3-8, D4-8, D5-8, one or more D6, D6-7, D6-8, D6-9, or D6-10, or a combination thereof, and a moiety of interest. In some embodiments, the polypeptide or complex comprises Endo180 Domains 1-9 (D1-9), D2-9, D3-9, D4-9, D5-9, one or more D6, D6-7, D6-8, D6-9, or D6-10, or a combination thereof, and a moiety of interest. In some embodiments, the polypeptide or complex comprises Endo180 Domains 1-10 (D1-10), D2-10, D3-10, D4-10, D5-10, one or more D6, D6-7, D6-8, D6-9, or D6-10, or a combination thereof, and a moiety of interest. In some embodiments, the polypeptide or complex comprises two or more D6 and a moiety of interest. In some embodiments, the polypeptide or complex comprises two or more consecutive D6 and a moiety of interest.

In some embodiments, the recombinant polypeptide includes an Endo180 ecto-domain sequence including an Endo180 Domain 6 (D6) sequence, wherein the Endo180 ecto-domain sequence is fused to a heterologous polypeptide sequence which may include any polypeptide that is not Endo180 or a fragment or variant thereof.

In some embodiments, the heterologous polypeptide sequence includes a tag, e.g., a tag for affinity purification, such as described above. In some embodiments, the affinity tag is biotin or an Fc region. In some embodiments, the recombinant polypeptide includes biotin and is capable of binding to streptavidin or avidin immobilized on a support as described herein. In some embodiments, the recombinant polypeptide includes an Fc region and is capable of binding to Protein A immobilized in a support as described herein. In some embodiments, the Fc region is or includes the sequence set forth by SEQ ID NO: 6. In some embodiments, the Fc region is or includes a sequence at least 70%, at least 75%, at least 80%, at least 85%, at least 90%, at least 95%, at least 99%, or 100% identical to SEQ ID NO: 6. In some embodiments, the recombinant polypeptide includes Endo180 Domains 1-6 (D1-6), D2-6, D3-6, D4-6, D5-6, one or more D6, D6-7, D6-8, D6-9, or D6-10, or a combination thereof. In some embodiments, the recombinant polypeptide includes Endo180 Domains 1-6 fused to an Fc region (D1-6-Fc), D2-6-Fc, D3-6-Fc, D4-6-Fc, D5-6-Fc, (D6)$_n$-Fc, D6-7-Fc, D6-8-Fc, D6-9-Fc, D6-10-Fc, D1-10-Fc, or a combination thereof, wherein n is an integer of 1 or greater.

In some embodiments, the recombinant polypeptide includes a sequence at least 70%, at least 75%, at least 80%, at least 85%, at least 90%, at least 95%, at least 99%, or 100% identical to SEQ ID NO: 1, 2, 3, or 4 or a fragment or variant thereof. In some embodiments, the recombinant polypeptide comprises the sequence of SEQ ID NO: 1. In some embodiments, the recombinant polypeptide includes a sequence at least 70%, at least 75%, at least 80%, at least 85%, at least 90%, at least 95%, at least 99%, or 100% identical to SEQ ID NO: 1. In some embodiments, the recombinant polypeptide comprises the sequence of SEQ ID NO: 2. In some embodiments, the recombinant polypeptide includes a sequence at least 70%, at least 75%, at least 80%, at least 85%, at least 90%, at least 95%, at least 99%, or 100% identical to SEQ ID NO: 2. In some embodiments, the recombinant polypeptide comprises the sequence of SEQ ID NO: 3. In some embodiments, the recombinant polypeptide includes a sequence at least 70%, at least 75%, at least 80%, at least 85%, at least 90%, at least 95%, at least 99%, or 100% identical to SEQ ID NO: 3. In some embodiments, the recombinant polypeptide comprises the sequence of SEQ ID NO: 4. In some embodiments, the recombinant polypeptide includes a sequence at least 70%, at least 75%, at least 80%, at least 85%, at least 90%, at least 95%, at least 99%, or 100% identical to SEQ ID NO: 4.

In some embodiments, the recombinant polypeptide includes a sequence at least 70%, at least 75%, at least 80%, at least 85%, at least 90%, at least 95%, at least 99%, or 100% identical to SEQ ID NO: 43, 44, 45, or 46 or a fragment or variant thereof. In some embodiments, the recombinant polypeptide comprises the sequence of SEQ ID NO: 43. In some embodiments, the recombinant polypeptide includes a sequence at least 70%, at least 75%, at least 80%, at least 85%, at least 90%, at least 95%, at least 99%, or 100% identical to SEQ ID NO: 43. In some embodiments, the recombinant polypeptide comprises the sequence of SEQ ID NO: 44. In some embodiments, the recombinant polypeptide includes a sequence at least 70%, at least 75%, at least 80%, at least 85%, at least 90%, at least 95%, at least 99%, or 100% identical to SEQ ID NO: 44. In some embodiments, the recombinant polypeptide comprises the sequence of SEQ ID NO: 45. In some embodiments, the recombinant polypeptide includes a sequence at least 70%, at least 75%, at least 80%, at least 85%, at least 90%, at least 95%, at least 99%, or 100% identical to SEQ ID NO: 45. In some embodiments, the recombinant polypeptide comprises the sequence of SEQ ID NO: 46. In some embodiments, the recombinant polypeptide includes a sequence at least 70%, at least 75%, at least 80%, at least 85%, at least 90%, at least 95%, at least 99%, or 100% identical to SEQ ID NO: 46.

In some embodiments, the Endo180 polypeptide is contained in a binding partner. In some embodiments, the binding partner includes an Endo180 ecto-domain sequence comprising an Endo180 Domain 6 (D6) sequence capable of binding to a molecules including a heterologous polypeptide sequence linked to a C-terminal polypeptide sequence of a procollagen, wherein all or a portion of the C-terminal polypeptide sequence binds to all or a portion of the Endo180 Domain 6 (D6) sequence. In some embodiments, the binding partner includes Endo180 Domains 1-6 fused to an Fc region (D1-6-Fc), D2-6-Fc, D3-6-Fc, D4-6-Fc, D5-6-Fc, (D6)$_n$-Fc, D6-7-Fc, D6-8-Fc, D6-9-Fc, D6-10-Fc, D1-10-Fc, or a combination thereof, wherein n is an integer of 1 or greater. In some embodiments, the Fc region is or includes the sequence set forth by SEQ ID NO: 6. In some embodiments, the Fc region is or includes a sequence at least 70%, at least 75%, at least 80%, at least 85%, at least 90%, at least 95%, at least 99%, or 100% identical to SEQ ID NO: 6 or 42. In some embodiments, the binding partner includes a sequence at least 70%, at least 75%, at least 80%, at least 85%, at least 90%, at least 95%, at least 99%, or 100% identical to SEQ ID NO: 1, 2, 3, 4, 43, 44, 45, or 46, or a fragment or variant thereof. In some embodiments, the binding partner comprises the sequence of SEQ ID NO: 1 or 43. In some embodiments, the binding partner includes a sequence at least 70%, at least 75%, at least 80%, at least 85%, at least 90%, at least 95%, at least 99%, or 100% identical to SEQ ID NO: 1 or 43. In some embodiments, the binding partner comprises the sequence of SEQ ID NO: 2 or 44. In some embodiments, the binding partner includes a sequence at least 70%, at least 75%, at least 80%, at least 85%, at least 90%, at least 95%, at least 99%, or 100% identical to SEQ ID NO: 2 or 44. In some embodiments, the binding partner comprises the sequence of SEQ ID NO: 3 or 45. In some embodiments, the binding partner includes a sequence at least 70%, at least 75%, at least 80%, at least 85%, at least 90%, at least 95%, at least 99%, or 100% identical to SEQ ID NO: 3 or 45. In some embodiments, the binding partner comprises the sequence of SEQ ID NO: 4 to 46. In some embodiments, the binding partner includes a sequence at least 70%, at least 75%, at least 80%, at least 85%, at least 90%, at least 95%, at least 99%, or 100% identical to SEQ ID NO: 4 or 46.

In some embodiments, the Endo180 polypeptides provided herein are capable of forming a complex with or binding to a C-terminal sequence of a procollagen. In some embodiments the procollagen is a human procollagen. In some embodiments, the C-terminal sequence of a procollagen comprises a C-terminal polypeptide of proα1(I), proα1 (II), proα1(III), proα1(V), proα1(XI), proα2(I), proα2(V), proα2(XI), or proα3(XI), or a fragment thereof. In some embodiments, the C-terminal sequence of a procollagen is or comprises a C-terminal polypeptide of proα1(I). In some embodiments, the Endo180 polypeptides provided herein are capable of forming a complex with or binding to a C-terminal sequence of a procollagen as described in Section II. In some embodiments, the Endo180 polypeptides provided herein are capable of forming a complex with or binding to a C-terminal sequence of a procollagen, wherein the sequence includes a C-prodomain of procollagen and a glycine repeat sequence of procollagen. In some embodiments, the Endo180 polypeptide complexes with or binds a C-prodomain of procollagen and a glycine repeat sequence of procollagen or portions thereof.

1. Polynucleotides and Vectors

Also provided are polynucleotides (nucleic acid molecules) encoding Endo180 polypeptides described herein, and vectors for genetically engineering cells to express such polypeptides.

In some embodiments, provided are polynucleotides that encode Endo180 polypeptide. In some aspects, the polynucleotide contains a single nucleic acid sequence, such as a nucleic acid sequence encoding a Endo180 polypeptide.

In some embodiments, the polynucleotide encoding the Endo180 polypeptide contains at least one promoter that is operatively linked to control expression of the Endo180 polypeptide or Endo180 fusion proteins. In some embodiments, the polynucleotide contains two, three, or more promoters operatively linked to control expression of the Endo180 polypeptide.

In some embodiments, expression of the Endo180 polypeptides is inducible or conditional. Thus, in some aspects, the polynucleotide encoding the fusion protein(s) contains a conditional promoter, enhancer, or transactivator. In some such aspects, the conditional promoter, enhancer, or transactivator is an inducible promoter, enhancer, or transactivator or a repressible promoter, enhancer, or transactivator.

In some embodiments, the polynucleotide encodes an Endo180 polypeptide sequence set forth by SEQ ID NO: 2 or 44. In some embodiments, the polynucleotide encodes an Endo180 polypeptide sequence at least 70%, at least 75%, at least 80%, at least 85%, at least 90%, at least 95%, at least 99%, or 100% identical to SEQ ID NO: 2 or 44. In some embodiments, the polynucleotide encodes an Endo180 polypeptide sequence set forth by SEQ ID NO: 4 or 46. In some embodiments, the polynucleotide encodes an Endo180 polypeptide sequence at least 70%, at least 75%, at least 80%, at least 85%, at least 90%, at least 95%, at least 99%, or 100% identical to SEQ ID NO: 4 or 46. In some embodiments, the polynucleotide encoding the Endo180 polypeptide includes a signal peptide. In some embodiments, the signal peptide inform the cellular trafficking of the Endo180 polypeptide. In some embodiments, the polynucleotide encodes a signal peptide sequence set forth by SEQ ID NO: 5. In some embodiments, the polynucleotide encodes a signal peptide sequence at least 70%, at least 75%, at least 80%, at least 85%, at least 90%, at least 95%, at least 99%, or 100% identical to SEQ ID NO: 5. In some embodiments, the polynucleotide encodes an Endo180 polypeptide sequence set forth by SEQ ID NO: 1 or 43. In some embodiments, the polynucleotide encodes an Endo180 polypeptide sequence at least 70%, at least 75%, at least 80%, at least 85%, at least 90%, at least 95%, at least 99%, or 100% identical to SEQ ID NO: 1 or 43. In some embodiments, the polynucleotide encodes an Endo180 polypeptide sequence set forth by SEQ ID NO: 3 or 45. In some embodiments, the polynucleotide encodes an Endo180 polypeptide sequence at least 70%, at least 75%, at least 80%, at least 85%, at least 90%, at least 95%, at least 99%, or 100% identical to SEQ ID NO: 3 or 45.

In some embodiments, the polynucleotide encoding the Endo180 polypeptide is introduced into a composition containing cultured cells (e.g., host cells), such as by retroviral transduction, transfection, or transformation. In some embodiments, this can allow for expression (e.g., production) of the Endo180 polypeptide. In some embodiments, the expressed Endo180 polypeptides are purified.

Also provided are vectors or constructs containing nucleic acid molecules as described herein. In some embodiments, the vectors or constructs contain one or more promoters operatively linked to the nucleic acid molecule encoding the Endo180 polypeptide to drive expression thereof.

In some embodiments, the vector is a viral vector. In some embodiments the viral vector is a retroviral vector. In some embodiments, the retroviral vector is a lentiviral vector. In some embodiments, the retroviral vector is a gammaretroviral vector.

In some embodiments, the vector or construct includes a single promoter that drives the expression of one or more nucleic acid molecules of the polynucleotide.

In some embodiments, the vector is comprised in a virus. In some embodiments, the virus is a pseudovirus. In some embodiments, the virus is a viral-like particle. In some embodiments, the vector is comprised in a cell. In some embodiments, the virus or cell in which the vector is comprised contains a recombinant genome.

B. Support

As described above, in some aspects, the Endo180 polypeptide described herein is present (e.g., coupled, linked, attached, absorbed) on a support. In some embodiments, the support is a solid support or a surface. In some embodiments, the support is or includes a resin, a particle, a bead, a solid substrate, a membrane, or a combination thereof. For example, the support may be bead or a solid resin. In some embodiments, the bead or resin is a stationary phase, for example a chromatography matrix. In some such embodiments, the Endo180 polypeptide is immobilized on the support. In some cases, the Endo180 polypeptide is immobilized to the support via covalent bonds. In some embodiments, the Endo180 polypeptide is immobilized to the support non-covalently.

In some embodiments, the support is a solid support. Any solid support (surface) can be used for the attachment of the Endo180 polypeptide. Non-limiting examples of solid supports on which the Endo180 polypeptide can be attached or absorbed include a magnetic bead, a polymeric bead, a cell culture plate, a microtiter plate, a membrane, plastic substrates, or a hollow fiber. In some embodiments, the Endo180 polypeptide is covalently attached to the solid support. In some embodiments, the Endo180 polypeptide is covalently linked to a CNBr activated resin. In some embodiments, the Endo180 polypeptide is non-covalently attached to the solid support. For example, when an Endo180 fusion protein containing a heterologous polypeptide sequence, such as an Fc sequence, is used, the solid support may have attached or absorbed thereon a molecule, protein, or other agent capable of binding to the heterologous polypeptide sequence. For example, in some embodiments, when using an Endo180 fusion protein containing an Fc sequence, the support may have attached or absorbed thereon protein A capable of binding to the Fc. Similar strategies and arrangements can be used for the affinity tag biotin and avidin or streptavidin.

Non-limiting examples of solid supports include Dyna-beads, agarose (e.g., Sepharose®), acrylamide resin, CNBr activated resin, polystyrene-divinylbenzene (PS-DVB), AminoLink resins, crosslinked resins, and chemically functionalized resins.

In some embodiments, the support contains a stationary phase. Thus, in some embodiments, the Endo180 polypeptide is comprised on a stationary phase (also called chromatography matrix). In some such embodiments, the Endo180 polypeptide is attached to the stationary phase. In some cases, the Endo180 polypeptide is attached to the stationary phase via covalent bonds. In some aspects, the Endo180 polypeptide is attached to the stationary phase non-covalently.

Any material may be employed as a chromatography matrix. In general, a suitable chromatography material is essentially innocuous, such as when used in a packed chromatography column under desired conditions. In some embodiments, the stationary phase remains in a predefined location, such as a predefined position, whereas the location of the sample is being altered. Thus, in some embodiments, the stationary phase is the part of a chromatographic system through which a mobile phase flows (either by gravity flow, flow through, or in a batch mode) and where distribution of the components contained in the liquid phase (either dissolved or dispersed) between the phases occurs.

In some embodiments, the chromatography matrix has the form of a solid or semisolid phase, whereas the sample that contains the target proteins to be isolated/separated is a fluid phase. The chromatography matrix can be a particulate material (of any suitable size and shape) or a monolithic chromatography material, including a paper substrate or membrane. Thus, in some aspects, the chromatography can be both column chromatography as well as planar chromatography. In some embodiments, in addition to standard chromatography columns, columns allowing a bidirectional flow such as PhyTip® columns available from PhyNexus, Inc. San Jose, CA, U.S.A. or pipette tips can be used for column based/flow through mode based methods. Thus, in some cases, pipette tips or columns allowing a bidirectional flow are also comprised by chromatography columns useful in the present methods. In some cases, such as where a particulate matrix material is used, the particulate matrix material may, for example, have a mean particle size of about 5 μm to about 200 μm, or from about 5 μm to about 400 μm, or from about 5 μm to about 600 μm. In some aspects, the chromatography matrix may, for example, be or include a polymeric resin or a metal oxide or a metalloid oxide. In some aspects, such as where planar chromatography is used, the matrix material may be any material suitable for planar chromatography, such as conventional cellulose-based or organic polymer based membranes (for example, a paper membrane, a nitrocellulose membrane or a polyvinylidene difluoride (PVDF) membrane) or silica coated glass plates. In some embodiments, the chromatography matrix/stationary phase is a non-magnetic material or non-magnetizable material. In some embodiments, the chromatography matrix is a magnetic material or magnetizable material.

In some embodiments, non-magnetic or non-magnetizable chromatography stationary phases that are suitable in the present methods include derivatized silica or a cross-linked gel. In some aspects, a crosslinked gel may be based on a natural polymer, such as on a polymer class that occurs in nature. For example, a natural polymer on which a chromatography stationary phase may be based is a polysaccharide. In some cases, a respective polysaccharide is generally crosslinked. An example of a polysaccharide matrix includes, but is not limited to, an agarose gel (for example, Superflow™ agarose or a Sepharose® material such as Superflow™ Sepharose® that are commercially available in different bead and pore sizes) or a gel of crosslinked dextran(s). A further illustrative example is a particulate cross-linked agarose matrix, to which dextran is covalently bonded, that is commercially available (in various bead sizes and with various pore sizes) as Sephadex® or Superdex®, both available from GE Healthcare. Another illustrative example of such a chromatography material is Sephacryl® which is also available in different bead and pore sizes from GE Healthcare.

In some embodiments, a crosslinked gel may also be based on a synthetic polymer, such as on a polymer class that does not occur in nature. In some aspects, such a synthetic polymer on which a chromatography stationary phase is based is a polymer that has polar monomer units, and which is therefore in itself polar. Thus, in some cases, such a polar polymer is hydrophilic. Hydrophilic molecules, also termed lipophobic, in some aspects contain moieties that can form dipole-dipole interactions with water molecules. In general, hydrophobic molecules, also termed lipophilic, have a tendency to separate from water.

Illustrative examples of suitable synthetic polymers are polyacrylamide(s), a styrene-divinylbenzene gel and a copolymer of an acrylate and a diol or of an acrylamide and a diol. An illustrative example is a polymethacrylate gel, commercially available as a Fractogel®. A further example is a copolymer of ethylene glycol and methacrylate, commercially available as a Toyopearl®. In some embodiments, a chromatography stationary phase may also include natural and synthetic polymer components, such as a composite matrix or a composite or a copolymer of a polysaccharide and agarose, e.g. a polyacrylamide/agarose composite, or of a polysaccharide and N,N'-methylenebisacrylamide. An illustrative example of a copolymer of a dextran and N,N'-methylenebisacrylamide is the above-mentioned Sephacryl® series of material. In some embodiments, a derivatized silica may include silica particles that are coupled to a synthetic or to a natural polymer. Examples of such embodiments include, but are not limited to, polysaccharide grafted silica, polyvinylpyrrolidone grafted silica, polyethylene oxide grafted silica, poly(2-hydroxyethylaspartamide) silica and poly(N-isopropylacrylamide) grafted silica.

In some embodiments, the chromatography matrix is a gel filtration matrix. Generally, a gel filtration can be characterized by the property that it is designed to undergo. A gel filtration matrix in some aspects allows the separation of biological entities largely on the basis of their size. In some such aspects, the respective chromatography matrix is typically a particulate porous material as mentioned above. The chromatography matrix may have a certain exclusion limit, which is typically defined in terms of a molecular weight above which molecules are entirely excluded from entering the pores. In some embodiments, the respective molecular weight defining the size exclusion limit may be selected to be below the weight corresponding to the weight of a target cell. In such an embodiment, the target cell is prevented from entering the pores of the size exclusion chromatography matrix. Likewise, a stationary phase may have pores that are of a size that is smaller than the size of a target protein, e.g., trimeric fusion protein.

In some embodiments, a chromatography matrix employed in the present methods may also include magnetically attractable matter such as one or more magnetically attractable particles or a ferrofluid. A respective magnetically attractable particle may comprise a Endo180 polypeptide. In some cases, magnetically attractable particles may contain diamagnetic, ferromagnetic, paramagnetic or superparamagnetic material. In general, superparamagnetic material responds to a magnetic field with an induced magnetic field without a resulting permanent magnetization. Magnetic particles based on iron oxide are for example commercially available as Dynabeads® from Dynal Biotech, as magnetic MicroBeads from Miltenyi Biotec, as magnetic porous glass beads from CPG Inc., as well as from various other sources, such as Roche Applied Science, BIOCLON, BioSource International Inc., micromod, AMBION, Merck, Bangs Laboratories, Polysciences, or Novagen Inc., to name only a few. Magnetic nanoparticles based on superparamagnetic Co and FeCo, as well as ferromagnetic Co nanocrystals have been described, for example by Hutten, A. et al. (J. Biotech. (2004), 112, 47-63).

In some embodiments, provided is an apparatus that contains at least one arrangement of a stationary phase, such as chromatography column. The apparatus may comprise a sample inlet being fluidly connected to the stationary phase of the arrangement and a sample outlet. See, e.g., Section III.

II. Trimeric Fusion Proteins

It is contemplated that the methods of purification provided herein may be used to purify therapeutic biologics, such as trimeric fusion proteins containing procollagen and domains thereof, e.g., a C-terminal polypeptide sequence of a procollagen.

As described above, many disease targets exist in trimeric forms and/or require trimerization to become active. For example, TNF-related apoptosis-inducing ligand (TRAIL/Apo2L), which is considered a promising cancer therapeutic, mediates activation of the extrinsic apoptosis pathway in a tumor-specific manner by binding to and trimerizing its functional receptors DR4 or DR5. As another example, some enveloped RNA virus antigens responsible for entry into host cells exist in a trimeric form. Methods of generating, preserving, and/or maintaining conformation of trimeric structures may improve the efficacy of therapeutic compositions, such as biologics, in treating disease. For example, trimerization of TRAIL proteins may facilitate the trimerzation of its functional receptors to promote apoptosis. Likewise, a subunit vaccine in which the trimeric form of RNA viral envelop proteins is maintained may allow access to antigenic sites capable of generating an immune response.

In some embodiments, trimerization of proteins, polypeptides, peptides of interest is accomplished by linking the molecule of interest at its C-terminus (C-terminal linkage) to a trimerization domain to promote trimerization of the monomers. In some embodiments, the trimerization stabilizes the membrane proximal aspect of the protein, polypeptide, peptide of interest in a trimeric configuration. In some embodiments, the proteins, polypeptides, peptides of interest are heterologous polypeptide sequences. A heterologous polypeptide sequence may be any heterologous sequence described herein or any polypeptide sequence suitable for trimerization, for example as a therapeutic and/or prophylactic agent such as a vaccine. In some embodiments, the heterologous polypeptide include any polypeptide that is not a trimerization domain or sequence.

In some embodiments, the heterologous polypeptide sequence is derived from a secreted protein or an ectodomain of a membrane protein. In some embodiments, the heterologous polypeptide sequence is mammalian.

Non-limiting examples of exogenous multimerization domains that promote stable trimers of soluble recombinant proteins include: the GCN4 leucine zipper (Harbury et al.

1993 Science 262:1401-1407), the trimerization motif from the lung surfactant protein (Hoppe et al. 1994 FEBS Lett 344:191-195), collagen (McAlinden et al. 2003 J Biol Chem 278:42200-42207), and the phage T4 fibritin Foldon (Miroshnikov et al. 1998 Protein Eng 11:329-414), any of which can be linked to a heterologous polypeptide sequence described herein (e.g., by linkage to the C-terminus of a heterologous polypeptide sequence) to promote trimerization of the heterologous polypeptide sequence.

In some embodiments, one or more peptide linkers (such as a gly-ser linker, for example, a 10 amino acid glycine-serine peptide linker) can be used to link the heterologous polypeptide sequence to the multimerization domain. The trimer can include any of the stabilizing mutations provided herein (or combinations thereof) as long as the heterologous polypeptide sequence trimer retains the desired properties.

To be therapeutically feasible, a desired trimerizing protein moiety for biologic drug designs should satisfy the following criteria. Ideally it should be part of a naturally secreted protein, like immunoglobulin Fc, that is also abundant (non-toxic) in the circulation, human in origin (lack of immunogenicity), relatively stable (long half-life) and capable of efficient self-trimerization which is strengthened by inter-chain covalent disulfide bonds so the trimerized heterologous polypeptide sequences are structurally stable.

Collagen is a family of fibrous proteins that are the major components of the extracellular matrix. It is the most abundant protein in mammals, constituting nearly 25% of the total protein in the body. Collagen plays a major structural role in the formation of bone, tendon, skin, cornea, cartilage, blood vessels, and teeth. The fibrillar types of collagen I, II, III, IV, V, and XI are all synthesized as larger trimeric precursors, called procollagens, in which the central uninterrupted triple-helical domain consisting of hundreds of "G-X-Y" repeats (or glycine repeats) is flanked by non-collagenous domains (NC), the N-propeptide and the C-propeptide. Both the C- and N-terminal extensions are processed proteolytically upon secretion of the procollagen, an event that triggers the assembly of the mature protein into collagen fibrils which forms an insoluble cell matrix. BMP-1 is a protease that recognizes a specific peptide sequence of procollagen near the junction between the glycine repeats and the C-prodomain of collagens and is responsible for the removal of the propeptide. The shed trimeric C-propeptide of type I collagen is found in human sera of normal adults at a concentration in the range of 50-300 ng/mL, with children having a much higher level which is indicative of active bone formation. In people with familial high serum concentration of C-propeptide of type I collagen, the level could reach as high as 1-6 µg/mL with no apparent abnormality, suggesting the C-propeptide is not toxic. Structural study of the trimeric C-propeptide of collagen suggested that it is a tri-lobed structure with all three subunits coming together in a junction region near their N-termini to connect to the rest of the procollagen molecule. Such geometry in projecting proteins to be fused in one direction is similar to that of Fc dimer.

Type I, IV, V and XI collagens are mainly assembled into heterotrimeric forms consisting of either two α-1 chains and one α-2 chain (for Type I, IV, V), or three different a chains (for Type XI), which are highly homologous in sequence. The type II and III collagens are both homotrimers of α-1 chain. For type I collagen, the most abundant form of collagen, stable α(I) homotrimer is also formed and is present at variable levels in different tissues. Most of these collagen C-propeptide chains can self-assemble into homotrimers, when over-expressed alone in a cell. Although the N-propeptide domains are synthesized first, molecular assembly into trimeric collagen begins with the in-register association of the C-propeptides. In some embodiments, the C-propeptide complex is stabilized by the formation of interchain disulfide bonds. In some embodiments, the inter-chain disulfide bond formation facilitates proper chain registration. In some embodiments, the interchain disulfide bonds form as the in-register association of the C-propeptides occurs. The triple helix of the glycine repeats and is then propagated from the associated C-termini to the N-termini in a zipper-like manner. This knowledge has led to the creation of non-natural types of collagen matrix by swapping the C-propeptides of different collagen chains using recombinant DNA technology. Non-collagenous proteins, such as cytokines and growth factors, also have been fused to the N-termini of either pro-collagens or mature collagens to allow new collagen matrix formation, which is intended to allow slow release of the noncollagenous proteins from the cell matrix. However, under both circumstances, the C-propeptides are required to be cleaved before recombinant collagen fibril assembly into an insoluble cell matrix.

Although, other protein trimerization domains, such as those from GCN4 from yeast fibritin from bacteria phage T4 and aspartate transcarbamoylase of *Escherichia coli*, have been described previously to allow trimerization of heterologous proteins, none of these trimerizing proteins are human in nature, nor are they naturally secreted proteins. As such, any trimeric fusion proteins would have to be made intracellularly, which not only may fold incorrectly for naturally secreted proteins such as soluble receptors, but also make purification of such fusion proteins from thousands of other intracellular proteins difficult. Moreover, the fatal drawback of using such non-human protein trimerization domains (e.g. from yeast, bacteria phage and bacteria) for trimeric biologic drug design is their presumed immunogenicity in the human body, rendering such fusion proteins ineffective shortly after injecting them into the human body.

The use of collagen in a recombinant polypeptide or fusion protein as described herein thus has many advantages, including: (1) collagen is the most abundant protein secreted in the body of a mammal, constituting nearly 25% of the total proteins in the body; (2) the major forms of collagen naturally occur as trimeric helixes, with their globular C-propeptides being responsible for the initiating of trimerization; (3) the trimeric C-propeptide of collagen proteolytically released from the mature collagen is found naturally at sub microgram/mL level in the blood of mammals and is not known to be toxic to the body; (4) the linear triple helical region of collagen can be included as a linker with predicted 2.9 Å spacing per residue, or excluded as part of the fusion protein so the distance between a protein to be trimerized and the C-propeptide of collagen can be precisely adjusted to achieve an optimal biological activity; (5) the recognition site of BMP1 which cleaves the C-propeptide off the pro-collagen can be mutated or deleted to prevent the disruption of a trimeric fusion protein; (6) the C-propeptide domain self-trimerizes via disulfide bonds between the C-propeptide domains in polypeptide chains, and the C-propeptide domain and/or the trimerized C-propeptide domains in a trimeric fusion protein can provide a tag such as a universal affinity tag (for different fusion partners fused to the same C-propeptide domain), which can be used for purification of any secreted fusion proteins created. Thus, different fusion partner polypeptide sequences can be fused to a C-propeptide domain sequences, the different fusion polypeptides can be expressed together (e.g., using the same host cell comprising expression vectors for the different fusion polypeptides), and each fusion polypeptide upon expression can trimerize to form a trimeric fusion protein, thereby generating a mixture comprising different fusion proteins comprising the same C-propeptide domain as a tag. The different fusion proteins can be efficiently purified together using an Endo180 polypeptide or protein disclosed herein. The last advantage described here makes trimeric fusion protein generated as described herein ideal for purification according to the methods provided herein.

In some embodiments, the heterologous polypeptide sequence is linked to a C-terminal propeptide of procollagen to form a fusion protein. In some embodiments, the C-terminal propeptides of the fusion proteins form inter-polypeptide bonds (e.g., disulfide bonds). In some embodiments, the fusion proteins form trimers. In some embodiments, the fusion protein trimers are referred to a trimeric fusion proteins. In some embodiments, the trimeric fusion protein is recombinantly produced.

In some embodiments, the C-terminal propeptide is of human collagen. In some embodiments, the C-terminal propeptide comprises a C-terminal polypeptide of proα1(I), proα1(II), proα1(III), proα1(V), proα1(XI), proα2(I), proα2(V), proα2(XI), or proα3(XI), or a fragment thereof. In some embodiments, the C-terminal propeptide is or comprises a C-terminal polypeptide of proα1(I).

In some embodiments, the C-terminal propeptide is or comprises the amino acid sequence set forth by SEQ ID NO: 18. In some embodiments, the C-terminal propeptide is an amino acid sequence having at least or about 85%, 90%, 92%, 95%, or 97% sequence identity to sequence of SEQ ID NO: 18. In some embodiments, the C-terminal propeptide is or comprises the amino acid sequence set forth by SEQ ID NO: 19. In some embodiments, the C-terminal propeptide is an amino acid sequence having at least or about 85%, 90%, 92%, 95%, or 97% sequence identity to sequence of SEQ ID NO: 19. In some embodiments, the C-terminal propeptide is or is the amino acid sequence set forth by SEQ ID NO: 30. In some embodiments, the C-terminal propeptide exhibits an amino acid sequence having at least or about 85%, 90%, 92%, 95%, or 97% sequence identity to sequence of SEQ ID NO: 20. In some embodiments, the C-terminal propeptide is or comprises the amino acid sequence set forth by SEQ ID NO: 21. In some embodiments, the C-terminal propeptide is an amino acid sequence having at least or about 85%, 90%, 92%, 95%, or 97% sequence identity to sequence of SEQ ID NO: 21.

In some embodiments, the C-terminal propeptide is or comprises the amino acid sequence set forth by SEQ ID NO: 22. In some embodiments, the C-terminal propeptide is an amino acid sequence having at least or about 85%, 90%, 92%, 95%, or 97% sequence identity to sequence of SEQ ID NO: 22. In some embodiments, the C-terminal propeptide is or comprises the amino acid sequence set forth by SEQ ID NO: 23. In some embodiments, the C-terminal propeptide is an amino acid sequence having at least or about 85%, 90%, 92%, 95%, or 97% sequence identity to sequence of SEQ ID NO: 23. In some embodiments, the C-terminal propeptide is or comprises the amino acid sequence set forth by SEQ ID NO: 24. In some embodiments, the C-terminal propeptide is an amino acid sequence having at least or about 85%, 90%, 92%, 95%, or 97% sequence identity to sequence of SEQ ID NO: 24. In some embodiments, the C-terminal propeptide is or comprises the amino acid sequence set forth by SEQ ID NO: 25. In some embodiments, the C-terminal propeptide is an amino acid sequence having at least or about 85%, 90%, 92%, 95%, or 97% sequence identity to sequence of SEQ ID NO: 25.

In some embodiments, the C-terminal propeptide is or comprises the amino acid sequence set forth by SEQ ID NO: 26. In some embodiments, the C-terminal propeptide is an amino acid sequence having at least or about 85%, 90%, 92%, 95%, or 97% sequence identity to sequence of SEQ ID NO: 26. In some embodiments, the C-terminal propeptide is or comprises the amino acid sequence set forth by SEQ ID NO: 27. In some embodiments, the C-terminal propeptide is an amino acid sequence having at least or about 85%, 90%, 92%, 95%, or 97% sequence identity to sequence of SEQ ID NO: 27. In some embodiments, the C-terminal propeptide is or comprises the amino acid sequence set forth by SEQ ID NO: 28. In some embodiments, the C-terminal propeptide is an amino acid sequence having at least or about 85%, 90%, 92%, 95%, or 97% sequence identity to sequence of SEQ ID NO: 28. In some embodiments, the C-terminal propeptide is or comprises the amino acid sequence set forth by SEQ ID NO: 29. In some embodiments, the C-terminal propeptide is an amino acid sequence having at least or about 85%, 90%, 92%, 95%, or 97% sequence identity to sequence of SEQ ID NO: 29.

In some embodiments, the C-terminal propeptide is or comprises the amino acid sequence set forth by SEQ ID NO: 30. In some embodiments, the C-terminal propeptide is an amino acid sequence having at least or about 85%, 90%, 92%, 95%, or 97% sequence identity to sequence of SEQ ID NO: 30. In some embodiments, the C-terminal propeptide is or comprises the amino acid sequence set forth by SEQ ID NO: 31. In some embodiments, the C-terminal propeptide is an amino acid sequence having at least or about 85%, 90%, 92%, 95%, or 97% sequence identity to sequence of SEQ ID NO: 31. In some embodiments, the C-terminal propeptide is or comprises the amino acid sequence set forth by SEQ ID NO: 32. In some embodiments, the C-terminal propeptide is an amino acid sequence having at least or about 85%, 90%, 92%, 95%, or 97% sequence identity to sequence of SEQ ID NO: 32. In some embodiments, the C-terminal propeptide is or comprises the amino acid sequence set forth by SEQ ID NO: 33. In some embodiments, the C-terminal propeptide is an amino acid sequence having at least or about 85%, 90%, 92%, 95%, or 97% sequence identity to sequence of SEQ ID NO: 33.

In some embodiments, the C-terminal propeptide is or comprises the amino acid sequence set forth by SEQ ID NO: 34. In some embodiments, the C-terminal propeptide is an amino acid sequence having at least or about 85%, 90%, 92%, 95%, or 97% sequence identity to sequence of SEQ ID NO: 34. In some embodiments, the C-terminal propeptide is or comprises the amino acid sequence set forth by SEQ ID NO: 35. In some embodiments, the C-terminal propeptide is an amino acid sequence having at least or about 85%, 90%, 92%, 95%, or 97% sequence identity to sequence of SEQ ID NO: 35. In some embodiments, the C-terminal propeptide is or comprises the amino acid sequence set forth by SEQ ID NO: 36. In some embodiments, the C-terminal propeptide is an amino acid sequence having at least or about 85%, 90%, 92%, 95%, or 97% sequence identity to sequence of SEQ ID NO: 36. In some embodiments, the C-terminal propeptide is or comprises the amino acid sequence set forth by SEQ ID NO: 37. In some embodiments, the C-terminal propeptide is an amino acid sequence having at least or about 85%, 90%, 92%, 95%, or 97% sequence identity to sequence of SEQ ID NO: 37.

In any of the preceding embodiments, the C-terminal propeptide can comprise a sequence comprising glycine-X-Y repeats linked to the N-terminus of any of SEQ ID NOs: 18-41, wherein X and Y are independently any amino acid, or an amino acid sequence at least 85%, 90%, 92%, 95%, or 97% identical thereto capable of forming inter-polypeptide disulfide bonds and trimerizing the recombinant polypeptides. In some embodiments, X and Y are independently proline or hydroxyproline.

In some cases where a heterologous polypeptide sequence is linked to the C-terminal propeptide to form the recombinant polypeptide, the fusion proteins form a trimer resulting in a trimeric fusion protein, e.g., a homotrimeric fusion protein.

In some embodiments, trimeric fusion proteins include individual recombinant polypeptides comprising the same heterologous polypeptide sequence. In some embodiments, trimeric fusion proteins include individual fusion proteins each comprising a different heterologous polypeptide sequence from the other fusion proteins. In some embodiments, trimeric fusion proteins include individual fusion proteins wherein one of the individual fusion proteins comprises a heterologous polypeptide sequence different from the other fusion proteins. In some embodiments, trimeric fusion proteins include individual fusion proteins wherein two of the fusion proteins comprise the same heterologous polypeptide sequence, and the heterologous polypeptide sequence is different from the heterologous polypeptide sequence comprised in the remaining fusion protein.

In some embodiments, the heterologous polypeptide sequence is mammalian. Exemplary trimeric fusion proteins are described in U.S. Pat. Nos. 7,268,116, 7,666,837, 7,691, 815, 10,618,949, Publication No. US2020/0190181, and Publication No. US2020/0199187, all of which are incorporated by reference in the entirety. In some embodiments, the heterologous polypeptide sequence contains a TNF family protein or fragment thereof. In some embodiments, the heterologous polypeptide sequence contains a TRAIL protein or fragment or variant thereof. In some embodiments, the heterologous polypeptide sequence contains a 4-1-BBL protein or fragment or variant thereof. In some embodiments, the heterologous polypeptide sequence contains an OX40L protein or fragment or variant thereof.

In some embodiments, the heterologous polypeptide sequence is viral. In some embodiments, the heterologous polypeptide sequence is from an RNA virus. In some embodiments, the RNA virus is selected from the group consisting of an HIV, an RSV, a coronavirus, an influenza virus, and a rabies virus. In some embodiments, the heterologous polypeptide contains a coronavirus Spike (S) protein or fragment or variant thereof. In some embodiments, the coronavirus is a SARS-CoV-2. In some embodiments, the coronavirus is a SARS-CoV-1. In some embodiments, the coronavirus is a MERS virus.

In some embodiments, the heterologous polypeptide contains s an HIV gp120 protein or fragment or variant thereof. In some embodiments, the heterologous polypeptide contains an RSV F protein or fragment or variant thereof. In some embodiments, the heterologous polypeptide contains an influenza virus HA protein or fragment or variant thereof. In some embodiments, the heterologous polypeptide comprises a rabies virus G protein or fragment or variant thereof.

In some embodiments, the trimeric fusion proteins described herein are therapeutic, diagnostic, and/or prophylactic agents.

A. Polynucleotides and Vectors

Also provided are polynucleotides (nucleic acid molecules) encoding the fusion proteins that generate trimeric fusion proteins provided herein, and vectors for genetically engineering cells to express such fusion proteins.

In some embodiments, provided are polynucleotides that encode fusion proteins provided herein. In some embodiments, the fusion proteins are encoded by a recombinant polynucleotide sequence comprising a polynucleotide sequence encoding a heterologous polypeptide sequence fused in-frame to a polynucleotide sequence encoding the C-terminal polypeptide sequence of the procollagen. In some aspects, the polynucleotide contains a single nucleic acid sequence, such as a nucleic acid sequence encoding a fusion protein. In other instances, the polynucleotide contains a first nucleic acid sequence encoding a fusion protein is a particular the heterologous polypeptide sequence and a second nucleic acid sequence encoding a fusion protein comprising a different heterologous polypeptide sequence.

In some embodiments, the polynucleotide encoding the recombinant polypeptide contains at least one promoter that is operatively linked to control expression of the recombinant polypeptide. In some embodiments, the polynucleotide contains two, three, or more promoters operatively linked to control expression of the recombinant polypeptide.

In some embodiments, for example when the polynucleotide contains two or more nucleic acid coding sequences, such as a sequences encoding fusion proteins containing different heterologous polypeptide sequences, and at least one promoter is operatively linked to control expression of the two or more nucleic acid sequences. In some embodiments, the polynucleotide contains two, three, or more promoters operatively linked to control expression of the fusion proteins.

In some embodiments, expression of the fusion protein(s) is inducible or conditional. Thus, in some aspects, the polynucleotide encoding the fusion protein(s) contains a conditional promoter, enhancer, or transactivator. In some such aspects, the conditional promoter, enhancer, or transactivator is an inducible promoter, enhancer, or transactivator or a repressible promoter, enhancer, or transactivator. For example, in some embodiments, an inducible or conditional promoter can be used to restrict expression of the fusion proteins to a specific microenvironment. In some embodiments, expression driven by the inducible or conditional promoter is regulated by exposure to an exogenous agent, such as heat, radiation, or drug.

In cases where the polynucleotide contains more than one nucleic acid sequence encoding a fusion protein, the polynucleotide may further include a nucleic acid sequence encoding a peptide between the one or more nucleic acid sequences. In some cases, the nucleic acid positioned between the nucleic acid sequences encodes a peptide that separates the translation products of the nucleic acid sequences during or after translation. In some embodiments, the peptide contains an internal ribosome entry site (IRES), a self-cleaving peptide, or a peptide that causes ribosome skipping, such as a T2A peptide.

In some embodiments, the polynucleotide encoding the fusion protein(s) is introduced into a composition containing cultured cells (e.g., host cells), such as by retroviral transduction, transfection, or transformation. In some embodiments, the fusion protein, e.g., trimeric fusion protein, is expressed from a mammalian cell. In some embodiments, this can allow for expression (e.g., production) of the fusion protein. In some embodiments, the expressed fusion proteins are purified according to the methods of purification provided herein.

Also provided are vectors or constructs containing nucleic acid molecules as described herein. In some embodiments, the vectors or constructs contain one or more promoters operatively linked to the nucleic acid molecule encoding the fusion protein to drive expression thereof. In some embodiments, the promoter is operatively linked to one or more than one nucleic acid molecule, e.g., nucleic acid molecule encoding fusion proteins containing different heterologous polypeptide sequence.

In some embodiments, the vector is a viral vector. In some embodiments the viral vector is a retroviral vector. In some embodiments, the retroviral vector is a lentiviral vector. In some embodiments, the retroviral vector is a gammaretroviral vector.

In some embodiments, the vector or construct includes a single promoter that drives the expression of one or more nucleic acid molecules of the polynucleotide. In some embodiments, such promoters can be multicistronic (bicistronic or tricistronic, see e.g., U.S. Pat. No. 6,060,273). For example, in some embodiments, transcription units can be engineered as a bicistronic unit containing an IRES (internal ribosome entry site), which allows coexpression of gene products (e.g., encoding different recombinant polypeptides) by a message from a single promoter. In some embodiments, the vectors provided herein are bicistronic, allowing the vector to contain and express two nucleic acid sequences. In some embodiments, the vectors provided herein are tricistronic, allowing the vector to contain and express three nucleic acid sequences.

In some embodiments, a single promoter directs expression of an RNA that contains, in a single open reading frame (ORF), two or three genes (e.g. encoding the chimeric signaling receptor and encoding a recombinant receptor) separated from one another by sequences encoding a self-cleavage peptide (e.g., 2A sequences) or a protease recognition site (e.g., furin). The ORF thus encodes a single polypeptide, which, either during (in the case of 2A) or after translation, is processed into the individual proteins. In some cases, the peptide, such as T2A, can cause the ribosome to skip (ribosome skipping) synthesis of a peptide bond at the C-terminus of a 2A element, leading to separation between the end of the 2A sequence and the next peptide downstream (see, for example, de Felipe. *Genetic Vaccines and Ther.* 2:13 (2004) and deFelipe et al. *Traffic* 5:616-626 (2004)). Many 2A elements are known in the art. Examples of 2A sequences that can be used in the methods and nucleic acids disclosed herein include, without limitation, 2A sequences from the foot-and-mouth disease virus (F2A), equine rhinitis A virus (E2A), Thosea asigna virus (T2A), and porcine teschovirus-1 (P2A) as described in U.S. Patent Publication No. 20070116690.

In some embodiments, the vector is comprised in a virus. In some embodiments, the virus is a pseudovirus. In some embodiments, the virus is a viral-like particle. In some embodiments, the vector is comprised in a cell. In some embodiments, the virus or cell in which the vector is comprised contains a recombinant genome.

III. Articles of Manufacture, Kits, or Apparatus

Also provided are articles of manufacture, kits, or apparatus containing the Endo180 polypeptides and supports as described herein. The articles of manufacture, kits, or apparatus may include a container and a label or package insert on or associated with the container. Suitable containers include, for example, bottles, vials, syringes, test tubes, IV solution bags, etc. The containers may be formed from a variety of materials such as glass or plastic. In some embodiments, the container has a sterile access port. Exemplary containers include solution bags, vials, including those with stoppers pierceable by a needle for injection. In some embodiments, the articles of manufacture, kits, or apparatus contains resins and columns suitable for purification methods described herein.

The article of manufacture or apparatus may further include a package insert indicating that the compositions can be used for purifying therapeutic proteins or biologics containing a C-terminal polypeptide sequence of a procollagen, such as trimeric fusion proteins described herein. The article of manufacture, kit, or apparatus may further include another or the same container comprising a pharmaceutically-acceptable buffer. It may further include other materials such as other buffers, diluents, filters, needles, and/or syringes.

In some embodiments is an apparatus for purification according to the methods described herein. The apparatus may include a solid support and/or containers being fluidly connected, for example in series.

The apparatus may include a sample inlet being fluidly connected to the solid support contained in a container. The apparatus may also comprise a sample outlet, the sample outlet being fluidly connected to the container containing the solid support.

In some embodiments, the apparatus is functionally closed system. In some embodiments, system is sterile.

Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

The terms "polypeptide" and "protein" are used interchangeably to refer to a polymer of amino acid residues, and are not limited to a minimum length. Polypeptides, including the provided receptors and other polypeptides, e.g., linkers or peptides, may include amino acid residues including natural and/or non-natural amino acid residues. The terms also include post-expression modifications of the polypeptide, for example, glycosylation, sialylation, acetylation, and phosphorylation. In some aspects, the polypeptides may contain modifications with respect to a native or natural sequence, as long as the protein maintains the desired activity. These modifications may be deliberate, as through site-directed mutagenesis, or may be accidental, such as through mutations of hosts which produce the proteins or errors due to PCR amplification.

As used herein, a "subject" is a mammal, such as a human or other animal, and typically is human. In some embodiments, the subject, e.g., patient, to whom the agent or agents, cells, cell populations, or compositions are administered, is a mammal, typically a primate, such as a human. In some embodiments, the primate is a monkey or an ape. The subject can be male or female and can be any suitable age, including infant, juvenile, adolescent, adult, and geriatric subjects. In some embodiments, the subject is a non-primate mammal, such as a rodent.

As used herein, "treatment" (and grammatical variations thereof such as "treat" or "treating") refers to complete or partial amelioration or reduction of a disease or condition or disorder, or a symptom, adverse effect or outcome, or phenotype associated therewith. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. The terms do not imply complete curing of a disease or complete elimination of any symptom or effect(s) on all symptoms or outcomes.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. In some embodiments, sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. In some embodiments, the provided cells and compositions are used to delay development of a disease or to slow the progression of a disease.

As used herein, to "suppress" a function or activity is to reduce the function or activity when compared to otherwise same conditions except for a condition or parameter of interest, or alternatively, as compared to another condition. For example, cells that suppress tumor growth reduce the rate of growth of the tumor compared to the rate of growth of the tumor in the absence of the cells.

An "effective amount" of an agent, e.g., a pharmaceutical formulation, cells, or composition, in the context of administration, refers to an amount effective, at dosages/amounts and for periods of time necessary, to achieve a desired result, such as a therapeutic or prophylactic result.

A "therapeutically effective amount" of an agent, e.g., a pharmaceutical formulation or cells, refers to an amount effective, at dosages and for periods of time necessary, to achieve a desired therapeutic result, such as for treatment of a disease, condition, or disorder, and/or pharmacokinetic or pharmacodynamic effect of the treatment. The therapeutically effective amount may vary according to factors such as the disease state, age, sex, and weight of the subject, and the populations of cells administered. In some embodiments, the provided methods involve administering the cells and/or compositions at effective amounts, e.g., therapeutically effective amounts.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount. In the context of lower tumor burden, the prophylactically effective amount in some aspects will be higher than the therapeutically effective amount.

The term "about" as used herein refers to the usual error range for the respective value readily known to the skilled person in this technical field. Reference to "about" a value or parameter herein includes (and describes) embodiments that are directed to that value or parameter per se.

As used herein, the singular forms "a," "an," and "the" include plural referents unless the context clearly dictates otherwise. For example, "a" or "an" means "at least one" or "one or more."

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

As used herein, a composition refers to any mixture of two or more products, substances, or compounds, including cells. It may be a solution, a suspension, liquid, powder, a paste, aqueous, non-aqueous or any combination thereof.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

EXAMPLES

The following examples are included for illustrative purposes only and are not intended to limit the scope of the present disclosure.

Figure 1A:
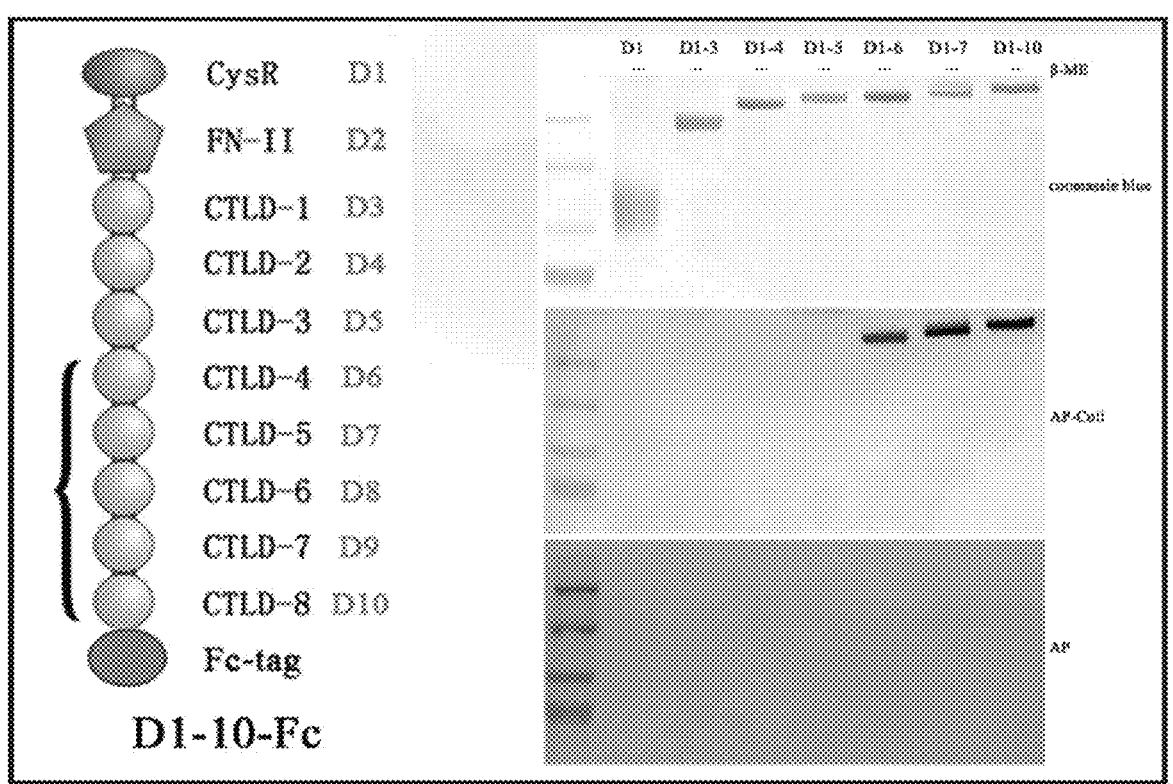
FIGS. 1A-1B show the identification of functional domains of Endo180 that are responsible for binding to the C-terminal region of α1(I) collagen.

Example 1 Generation of Soluble Endo180 Polypeptides cDNAs encoding serial deletions of human Endo180 domains as indicated in FIG. 1A (domains D1, D1-3, D1-4, D1-5, D1-6, D1-7, or D1-10 retained) were generated by PCR from a full length cDNA template of Endo180 and subcloned into pGH-hFc expression vector (GenHunter Corporation) to allow in-frame fusion to human IgG Fc. The resulting expression vectors each encoding exemplary Endo-180-Fc fusion protein were transfected into GH-CHO cells. Stable clones expressing high levels of each fusion protein were selected via step-wise gene amplifications under increasing MTX concentration. The exemplary recombinant Endo-180-Fc fusion proteins were produced in a Fed-batch serum-free cell culture as secreted proteins and purified to homogeneity by MAbSelectSure Protein A Sepharose resin (GE Biosciences). The resulting exemplary fusion proteins, with Fc alone as a negative control, were separated by a non-reducing SDS-PAGE (FIG. 1A; right upper panel showing Coomassie blue staining).

To determine which Endo180 domain was involved in collagen binding, a human placental alkaline phosphatase and collagen fusion construct (AP-Coll) containing the C-terminal glycine repeat region and prodomain of rat col1a1 (accession number Z78279) was used as an affinity probe after the exemplary Endo180-Fc fusion proteins were transferred to a PVDF membrane. Upon visualization of any bound AP (Alkaline phosphatase) activity, the results showed that collagen binding activity resides in D6 or thereafter of Endo180 (right middle panel, AP-Coll). The AP alone was used a negative control (FIG. 1A; right lower panel).

Figure 1B:
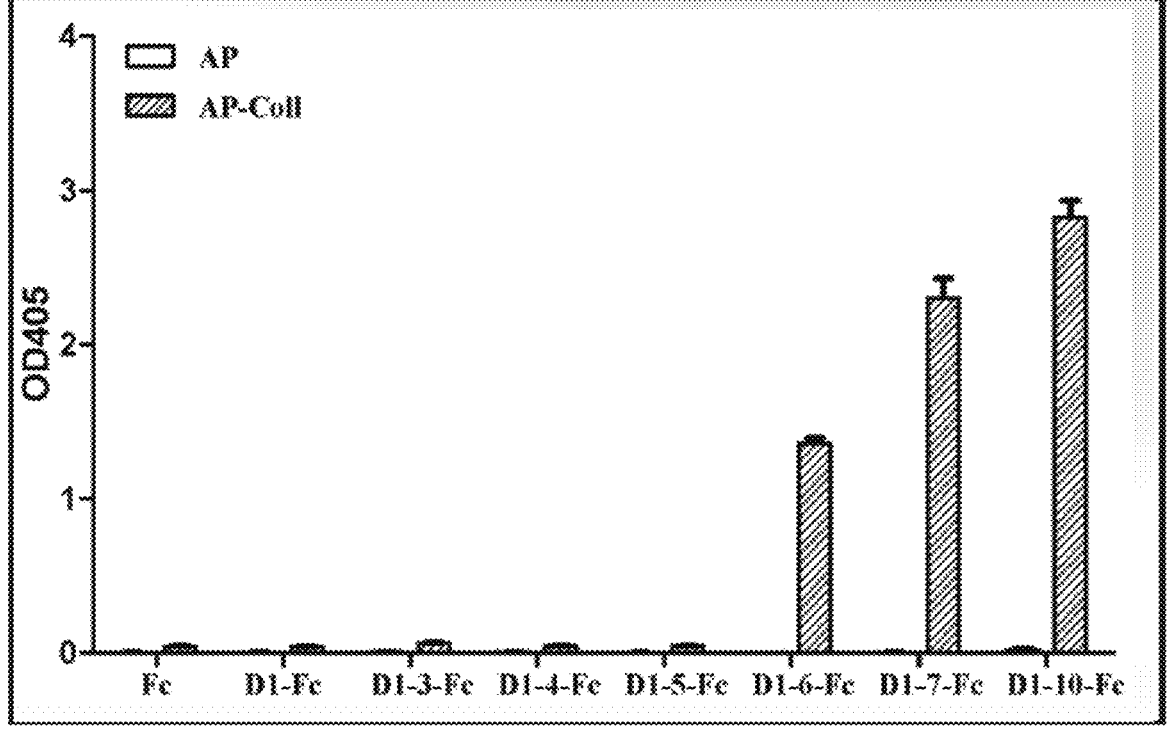

To further confirm and quantify the Endo180 and collagen binding, each Endo180-Fc fusion protein was captured on a 96-well microtiter plate that was pre-coated with protein A (Prospect). The exemplary Endo180-Fc fusion proteins that were able to bind to AP-Coll were determined by bound AP (Alkaline phosphatase) activity (FIG. 1B), which confirmed the results obtained in FIG. 1A.

Example 2 Identification of Endo180 Domains for Procollagen Binding

Figure 2A:
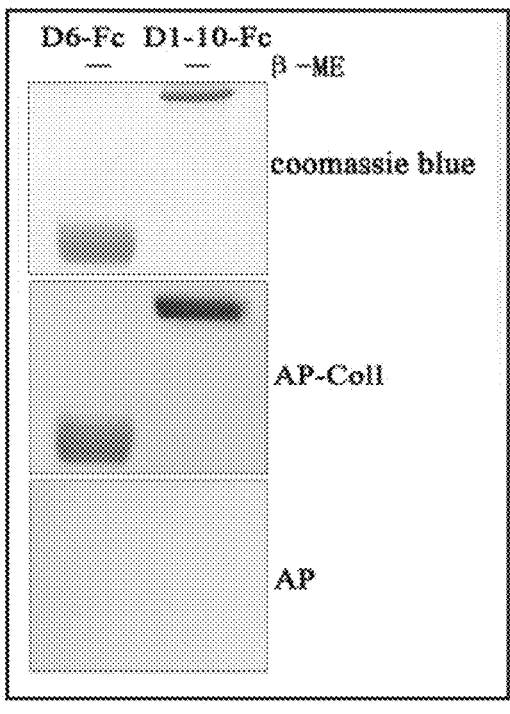
FIGS. 2A-2B show the identification of Endo180 domains for procollagen binding.

To further dissect which Endo180 domain from D6 on was responsible for procollagen binding, additional Fc fusion proteins were constructed following the same strategy as described in Example 1. As shown in FIG. 2A, domain 6 (D6) alone, which encodes the 4th CTLD, when fused to Fc (D6-Fc), was capable of procollagen binding, when D1-10-Fc served as a positive control.

Figure 2B:
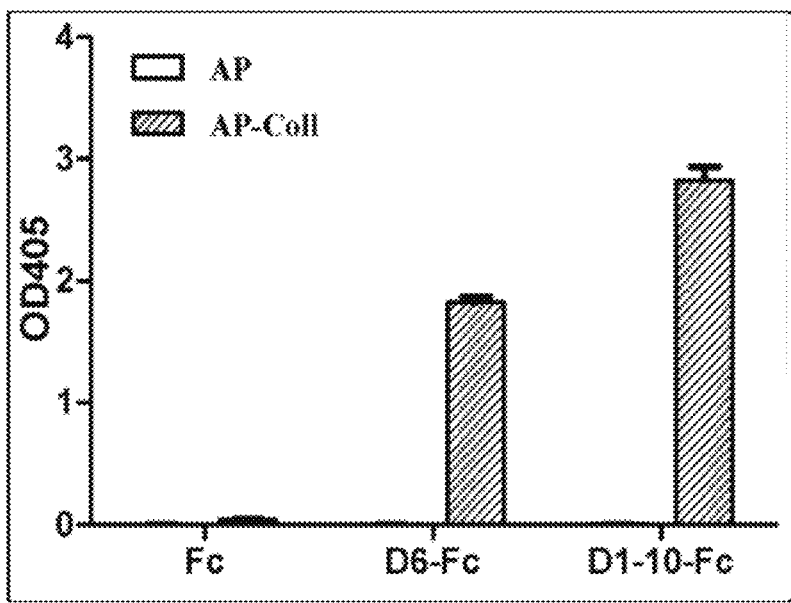

To further confirm this finding, exemplary D6-Fc and D1-10-Fc fusion proteins were captured on a 96-well microtiter plate that was pre-coated with protein A (Prospect), and bound AP-Coll was determined by AP (Alkaline phosphatase) activity as above (FIG. 2B). The observed AP-Coll binding was supportive of the results observed in FIG. 2A, suggesting that D6 alone was capable of procollagen binding.

Figures 4, 5A, 5B:
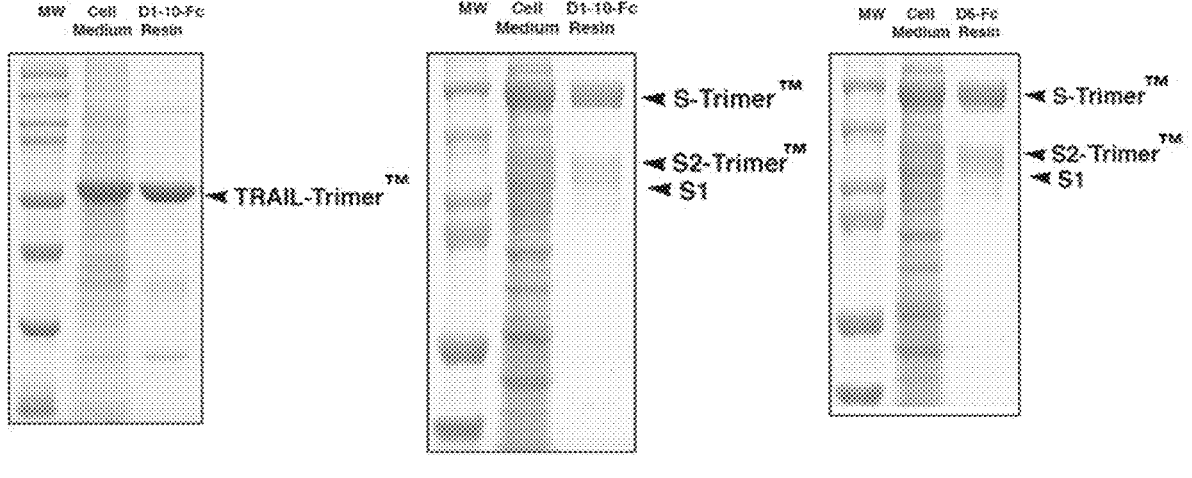
FIG. 4 shows SDS-PAGE analysis of affinity purification of an exemplary trimeric fusion protein comprising TRAIL fused to a C-terminal polypeptide sequence of a procollagen (this trimeric form of TRAIL is referred to as TRAIL-Trimer™) from a serum-free cell culture media using an exemplary Endo180 D1-10-Fc fusion protein as an affinity tag covalently linked to CNBr activated resins. The exemplary TRAIL-Trimer™ fusion protein was expressed in GH-CHO cells as a secreted protein, and the serum-free cell culture medium containing TRAIL-Trimer™ was loaded onto Protein A Sepharose resins with D1-10-Fc pre-captured to the column via the high-affinity interaction between Protein A and Fc. After washing off any unbound contaminating proteins, the bound TRAIL-Trimer™ was purified to near homogeneity in a single step using 0.5 M-1.0 M NaCl in phosphate buffered saline, and analyzed by SDS-PAGE as indicated.
FIGS. 5A-5D show SDS-PAGE analysis of affinity purification of an exemplary trimeric fusion protein comprising a SARS-CoV-2 spike (S) protein sequence fused to a C-terminal polypeptide sequence of a procollagen (this stabilized trimeric form of S protein is referred to as S-Trimer™, a SARS-CoV-2 subunit vaccine candidate) from cell culture media using exemplary Endo180-Fc fusion proteins as affinity tags non-covalently bound to Protein A Sepharose resins.

Example 3 Affinity Purification of Trimeric Fusion Proteins Using Endo180-Fc Fusion Proteins as an Affinity Tag Covalently Linked to CNBr Activated Resins To determine the ability of exemplary Endo180-Fc fusion proteins to act as an affinity tag for purification of trimeric fusion proteins containing collagen, an exemplary Endo180 fusion protein, D1-10-Fc, was covalently immobilized to a CNBr activated resin (Nawei BioSciences). An exemplary human TRAIL-Trimer fusion protein (Liu et al., (2017) Sci Rep. 7(1):8953) was expressed in GH-CHO cells as a secreted protein, and the cell culture medium containing TRAIL-Trimer fusion protein was loaded onto the D1-10-Fc immobilized column. After washing off any unbound contaminating proteins, the bound TRAIL-Trimer™ fusion protein was purified to near homogeneity after elusion with 0.5 M NaCl in phosphate buffered saline (FIG. 4).

Example 4 Affinity Purification of Trimeric Fusion Proteins Using Endo180-Fc Fusion Proteins as Affinity Tags Non-Covalently Bound to Protein a Sepharose Resins To determine the ability of exemplary D1-10-Fc and D6-Fc Endo180 fusion proteins to act as an affinity tag for purification of trimeric fusion proteins containing collagen, D1-10-Fc or D6-Fc fusion proteins were captured by Protein A Sepharose resins (PresmA, GE BioSciences). An exemplary S-Trimer™ fusion protein (a native SARS-Cov-2 Spike protein antigen fused to collagen Trimer-Tag™) was expressed in GH-CHO cells as a secreted protein, and the cell culture medium containing S-Trimer™ was loaded onto Protein A Sepharose resins with either D1-10-Fc or D6-Fc pre-captured to the column via the high-affinity interaction between Protein A and Fc. After washing off any unbound contaminating proteins, the bound S-Trimer™ was purified to near homogeneity in a single step using 0.5 M-1.0 M NaCl in phosphate buffered saline, respectively as analyzed by SDS-PAGE as indicated in FIG. 5A (D1-10-Fc) and FIG. 5B (D6-Fc).

Figure 5C:
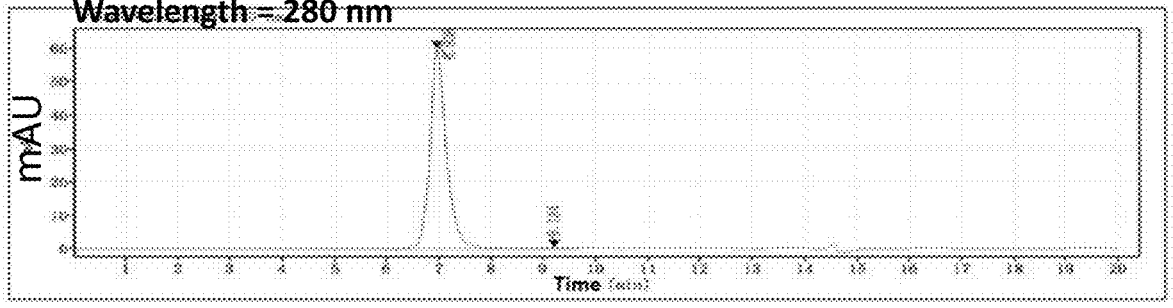
Figure 5D:
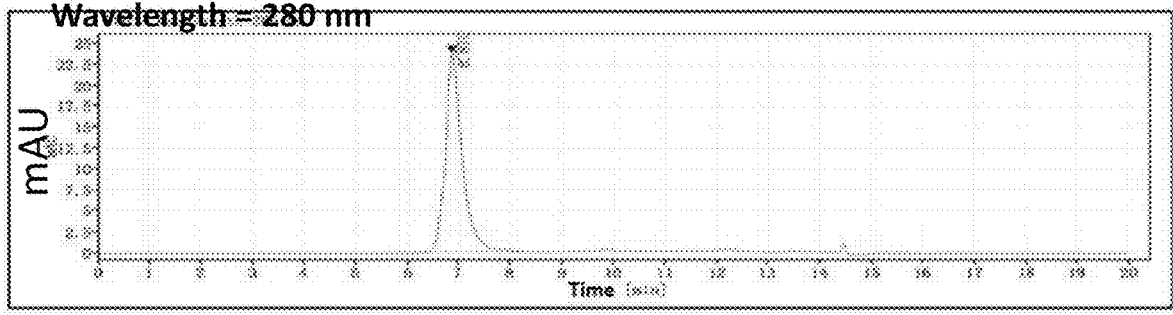

The purity of the partially cleaved S-Trimer™ at S1/S2 boundary by furin protease purified from either D1-10-Fc or D6-Fc affinity tag was analyzed by Size-exclusion SEC-HPLC (FIGS. 5C and 5D, respectively). The results showed that the partially cleaved S-Trimer™ existed as a single peak, indicating the cleaved S1 eluted from the affinity columns appeared to still be bound to the S2-Trimer™.

To further determine the ability of exemplary D6-Fc fusion protein to act as an affinity tag for purification of trimeric fusion proteins containing collagen C-prodomain, D6-Fc fusion protein was captured by Protein A Sepharose resins (PresmA, GE BioSciences) and used to purify another form of S-Trimer™ fusion protein (a SARS-Cov-2 Spike protein antigen with furin cleavage site mutation). This exemplary S-Trimer™ fusion protein was expressed in GH-CHO cells as a secreted protein, and the serum-free cell culture medium containing S-Trimer™ was loaded onto Protein A Sepharose resins with D6-Fc (FIG. 6) pre-captured to the column via the high-affinity interaction between Protein A and Fc. After washing off any unbound contaminating proteins, the bound furin site mutant S-Trimer™ was purified to near homogeneity in a single step using 0.5 M-1.0 M NaCl in phosphate buffered saline, as analyzed by SDS-PAGE as indicated. Note, in comparison with that of native S-Trimer™, the purified furin site mutant from of S-Trimer™ did not show any S1 subunit due to furin cleavage (FIG. 6).

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

SEQUENCE LISTING

| SEQ ID | SEQUENCE | ANNOTATION |
|---|---|---|
| 1 | MGPGRPAPAPWPRHLLRCVLLLGCLHLGRPGAPGDAALPEPNVFLIFSHGLQGC LEAQGGQVRVTPACNTSLPAQRWKWVSRNRLFNLGTMQCLGTGWPGTNTTASLG MYECDREALNLRWHCRTLGDQLSLLLGARTSNISKPGTLERGDQTRSGQWRIYG SEEDLCALPYHEVYTIQGNSHGKPCTIPFKYDNQWFHGCTSTGREDGHLWCATT QDYGKDERWGFCPIKSNDCETFWDKDQLTDSCYQFNFQSTLSWREAWASCEQQG ADLLSITEIHEQTYINGLLTGYSSTLWIGLNDLDTSGGWQWSDNSPLKYLNWES DQPDNPSEENCGVIRTESSGGWQNRDCSIALPYVCKKKPNATAEPTPPDRWANV KVECEPSWQPFQGHCYRLQAEKRSWQESKKACLRGGGDLVSIHSMAELEFITKQ IKQEVEELWIGLNDLKLQMNFEWSDGSLVSFTHWHPFEPNNERDSLEDCVTIWG PEGRWNDSPCNQSLPSICKKAGQLSQGAAEEDHGCRKGWTWHSPSCYWLGEDQV TYSEARRLCTDHGSQLVTITNRFEQAFVSSLIYNWEGEYFWTALQDLNSTGSFF WLSGDEVMYTHWNRDQPGYSRGGCVALATGSAMGLWEVKNCTSFRARYICRQSL GTPVTPELPGPDPTPSLTGSCPQGWASDTKLRYCYKVFSSERLQDKKSWVQAQG ACQELGAQLLSLASYEEEHFVANMLNKIFGESEPEIHEQHWFWIGLNRRDPRGG QSWRWSDGVGFSYHNFDRSRHDDDDIRGCAVLDLASLQWVAMQCDTQLDWICKI PRGTDVREPDDSPQGRREWLRFQEAEYKFFEHHSTWAQAQRICTWFQAELTSVH SQAELDFLSHNLQKFSRAQEQHWWIGLHTSESDGRFRWTDGSIINFISWAPGKP RPVGKDKKCVYMTASREDWGDQRCLTALPYICKRSNVTKETQPPDLPTTALGGC PSDWIQFLNKCFQVQGQEPQSRVKWSEAQFSCEQQEAQLVTITNPLEQAFITAS LPNVTFDLWIGLHASQRDFQWVEQEPLMYANWAPGEPSGPSPAPSGNKPTSCAV VLHSPSAHFTGRWDDRSCTEETHGFICQKGTDPSLSPSPAALPPAPGTELSYLN GTFRLLQKPLRWHDALLLCESRNASLAYVPDPYTQAFLTQAARGLRTPLWIGLA GEEGSRRYSWVSEEPLNYVGWQDGEPQQPGGCTYVDVDGAWRTTSCDTKLQGAV CGVSSGPPPPRRISYHGSCPQGLADSAWIPFREHCYSFHMELLLGHKEARQRCQ RAGGAVLSILDEMENVFVWEHLQSYEGQSRGAWLGMNFNPKGGTLVWQDNTAVN YSNWGPPGLGPSMLSHNSCYWIQSNSGLWRPGACTNITMGVVCKQAYVRSEPKS CDKTHTCPPCPAPELLGGPSVFLFPPKPKDTLMISRTPEVTCVVVDVSHEDPEV KFNWYVDGVEVHNAKTKPREEQYNSTYRVVSVLTVLHQDWLNGKEYKCKVSNKA LPAPIEKTISKAKGQPREPQVYTLPPSRDELTKNQVSLTCLVKGFYPSDIAVEW ESNGQPENNYKTTPPVLDSDGSFFLYSKLTVDKSRWQQGNVFSCSVMHEALHNH YTQKSLSLSPGK | Full length Endo180-Fc (D1-10-Fc) |
| 2 | GAPGDAALPEPNVFLIFSHGLQGCLEAQGGQVRVTPACNTSLPAQRWKWVSRNR LFNLGTMQCLGTGWPGTNTTASLGMYECDREALNLRWHCRTLGDQLSLLLGART SNISKPGTLERGDQTRSGQWRIYGSEEDLCALPYHEVYTIQGNSHGKPCTIPFK YDNQWFHGCTSTGREDGHLWCATTQDYGKDERWGFCPIKSNDCETFWDKDQLTD SCYQFNFQSTLSWREAWASCEQQGADLLSITEIHEQTYINGLLTGYSSTLWIGL NDLDTSGGWQWSDNSPLKYLNWESDQPDNPSEENCGVIRTESSGGWQNRDCSIA LPYVCKKKPNATAEPTPPDRWANVKVECEPSWQPFQGHCYRLQAEKRSWQESKK ACLRGGGDLVSIHSMAELEFITKQIKQEVEELWIGLNDLKLQMNFEWSDGSLVS FTHWHPFEPNNFRDSLEDCVTIWGPEGRWNDSPCNQSLPSICKKAGQLSQGAAE EDHGCRKGWTWHSPSCYWLGEDQVTYSEARRLCTDHGSQLVTITNRFEQAFVSS LIYNWEGEYFWTALQDLNSTGSFFWLSGDEVMYTHWNRDQPGYSRGGCVALATG SAMGLWEVKNCTSFRARYICRQSLGTPVTPELPGPDPTPSLTGSCPQGWASDTK LRYCYKVFSSERLQDKKSWVQAQGACQELGAQLLSLASYEEEHFVANMLNKIFG | Mature Endo-180-Fc (D1-10-Fc) |

-continued

| SEQUENCE LISTING | | |
|---|---|---|
| SEQ ID | SEQUENCE | ANNOTATION |

|  | ESEPEIHEQHWFWIGLNRRDPRGGQSWRWSDGVGFSYHNFDRSRHDDDDIRGCA VLDLASLQWVAMQCDTQLDWICKIPRGTDVREPDDSPQGRREWLRFQEAEYKFF EHHSTWAQAQRICTWFQAELTSVHSQAELDFLSHNLQKFSRAQEQHWWIGLHTS ESDGRFRWTDGSIINFISWAPGKPRPVGKDKKCVYMTASREDWGDQRCLTALPY ICKRSNVTKETQPPDLPTTALGGCPSDWIQFLNKCFQVQGQEPQSRVKWSEAQF SCEQQEAQLVTITNPLEQAFITASLPNVTFDLWIGLHASQRDFQWVEQEPLMYA NWAPGEPSGPSPAPSGNKPTSCAVVLHSPSAHFTGRWDDRSCTEETHGFICQKG TDPSLSPSPAALPPAPGTELSYLNGTFRLLQKPLRWHDALLLCESRNASLAYVP DPYTQAFLTQAARGLRTPLWIGLAGEEGSRRYSWVSEEPLNYVGWQDGEPQQPG GCTYVDVDGAWRTTSCDTKLQGAVCGVSSGPPPPRRISYHGSCPQGLADSAWIP FREHCYSFHMELLLGHKEARQRCQRAGGAVLSILDEMENVFVWEHLQSYEGQSR GAWLGMNFNPKGGTLVWQDNTAVNYSNWGPPGLGPSMLSHNSCYWIQSNSGLWR PGACTNITMGVVCKQAYVRSEPKSCDKTHTCPPCPAPELLGGPSVFLFPPKPKD TLMISRTPEVTCVVVDVSHEDPEVKFNWYVDGVEVHNAKTKPREEQYNSTYRVV SVLTVLHQDWLNGKEYKCKVSNKALPAPIEKTISKAKGQPREPQVYTLPPSRDE LTKNQVSLTCLVKGFYPSDIAVEWESNGQPENNYKTTPPVLDSDGSFFLYSKLT VDKSRWQQGNVFSCSVMHEALHNHYTQKSLSLSPGK |  |
| 3 | MGPGRPAPAPWPRHLLRCVLLLGCLHLGRPRSPVTPELPGPDPTPSLTGSCPQG WASDTKLRYCYKVFSSERLQDKKSWVQAQGACQELGAQLLSLASYEEEHFVANM LNKIFGESEPEIHEQHWFWIGLNRRDPRGGQSWRWSDGVGFSYHNFDRSRHDDD DIRGCAVLDLASLQWVAMQCDTQLDWICKIPRSEPKSCDKTHTCPPCPAPELLG GPSVFLFPPKPKDTLMISRTPEVTCVVVDVSHEDPEVKENWYVDGVEVHNAKTK PREEQYNSTYRVVSVLTVLHQDWLNGKEYKCKVSNKALPAPIEKTISKAKGQPR EPQVYTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPGK | Full Length D6-Fc |
| 4 | RSPVTPELPGPDPTPSLTGSCPQGWASDTKLRYCYKVFSSERLQDKKSWVQAQG ACQELGAQLLSLASYEEEHFVANMLNKIFGESEPEIHEQHWFWIGLNRRDPRGG QSWRWSDGVGFSYHNFDRSRHDDDDIRGCAVLDLASLQWVAMQCDTQLDWICKI PRSEPKSCDKTHTCPPCPAPELLGGPSVFLFPPKPKDTLMISRTPEVTCVVVDV SHEDPEVKFNWYVDGVEVHNAKTKPREEQYNSTYRVVSVLTVLHQDWLNGKEYK CKVSNKALPAPIEKTISKAKGQPREPQVYTLPPSRDELTKNQVSLTCLVKGFYP SDIAVEWESNGQPENNYKTTPPVLDSDGSFFLYSKLTVDKSRWQQGNVFSCSVM HEALHNHYTQKSLSLSPGK | Mature D6-Fc |
| 5 | MGPGRPAPAPWPRHLLRCVLLLGCLHLGRP | Signal Peptide |
| 6 | EPKSCDKTHTCPPCPAPELLGGPSVFLFPPKPKDTLMISRTPEVTCVVVDVSHE DPEVKFNWYVDGVEVHNAKTKPREEQYNSTYRVVSVLTVLHQDWLNGKEYKCKV SNKALPAPIEKTISKAKGQPREPQVYTLPPSRDELTKNQVSLTCLVKGFYPSDI AVEWESNGQPENNYKTTPPVLDSDGSFFLYSKLTVDKSRWQQGNVFSCSVMHEA LHNHYTQKSLSLSPGK | Fc |
| 7 | GAPGDAALPEPNVFLIFSHGLQGCLEAQGGQVRVTPACNTSLPAQRWKWVSRNR LFNLGTMQCLGTGWPGTNTTASLGMYECDREALNLRWHCRTLGDQLSLLLGART SNISKPGTLERGDQTRSGQWRIYGSEEDLCALPYHEVYTIQGNSHGKPCTIPPK YDNQWFHGCTSTGREDGHLWCATTQDYGKDERWGFCPIKSNDCETFWDKDQLTD SCYQFNFQSTLSWREAWASCEQQGADLLSITEIHEQTYINGLLTGYSSTLWIGL NDLDTSGGWQWSDNSPLKYLNWESDQPDNPSEENCGVIRTESSGGWQNRDCSIA LPYVCKKKPNATAEPTPPDRWANVKVECEPSWQPFQGHCYRLQAEKRSWQESKK ACLRGGGDLVSIHSMAELEFITKQIKQEVEELWIGLNDLKLQMNFEWSDGSLVS FTHWHPFEPNNERDSLEDCVTIWGPEGRWNDSPCNQSLPSICKKAGQLSQGAAE EDHGCRKGWTWHSPSCYWLGEDQVTYSEARRLCTDHGSQLVTITNRFEQAFVSS LIYNWEGEYFWTALQDLNSTGSFFWLSGDEVMYTHWNRDQPGYSRGGCVALATG SAMGLWEVKNCTSFRARYICRQSLGTPVTPELPGPDPTPSLTGSCPQGWASDTK LRYCYKVFSSERLQDKKSWVQAQGACQELGAQLLSLASYEEEHFVANMLNKIFG ESEPEIHEQHWFWIGLNRRDPRGGQSWRWSDGVGFSYHNFDRSRHDDDDIRGCA VLDLASLQWVAMQCDTQLDWICKIPRGTDVREPDDSPQGRREWLRFQEAEYKFF EHHSTWAQAQRICTWFQAELTSVHSQAELDFLSHNLQKFSRAQEQHWWIGHTS ESDGRFRWTDGSIINFISWAPGKPRPVGKDKKCVYMTASREDWGDQRCLTALPY ICKRSNVTKETQPPDLPTTALGGCPSDWIQFLNKCFQVQGQEPQSRVKWSEAQF SCEQQEAQLVTITNPLEQAFITASLPNVTFDLWIGLHASQRDFQWVEQEPLMYA NWAPGEPSGPSPAPSGNKPTSCAVVLHSPSAHFTGRWDDRSCTEETHGFICQKG TDPSLSPSPAALPPAPGTELSYLNGTFRLLQKPLRWHDALLLCESRNASLAYVP DPYTQAFLTQAARGLRTPLWIGLAGEEGSRRYSWVSEEPLNYVGWQDGEPQQPG GCTYVDVDGAWRTTSCDTKLQGAVCGVSSGPPPPRRISYHGSCPQGLADSAWIP FREHCYSFHMELLLGHKEARQRCQRAGGAVLSILDEMENVFVWEHLQSYEGQSR GAWLGMNFNPKGGTLVWQDNTAVNYSNWGPPGLGPSMLSHNSCYWIQSNSGLWR PGACTNITMGVVCKLPRAEQSSFSPSALPENPAA | Mature Endo180 Ecto-domain (Uniprot Q9UBG0) |
| 8 | PNVFLIFSHGLQGCLEAQGGQVRVTPACNTSLPAQRWKWVSRNRLENLGTMQCL GTGWPGTNTTASLGMYECDREALNLRWHCRTLGDQLSLLLGARTSNISKPGTLE RGDQTRSGQWRIYGSEEDL | D1 (Ricin B-type lectin domain) |

-continued

| SEQUENCE LISTING | | |
| --- | --- | --- |
| SEQ ID | SEQUENCE | ANNOTATION |
| 9 | SHGKPCTIPFKYDNQWFHGCTSTGREDGHLWCATTQDYGKDERWGFCPI | D2 (Fibronectin type-II domain) |
| 10 | LTDSCYQFNFQSTLSWREAWASCEQQGADLLSITEIHEQTYINGLLTGYSSTLW IGLNDLDTSGGWQWSDNSPLKYLNWESDQPDNPSEENCGVIRTESSGGWQNRDC SIALPYVCK | D3 (C-type lectin 1) |
| 11 | FQGHCYRLQAEKRSWQESKKACLRGGGDLVSIHSMAELEFITKQIKQEVEELWI GLNDLKLQMNFEWSDGSLVSFTHWHPFEPNNERDSLEDCVTIWGPEGRWNDSPC NQSLPSICK | D4 (C-type lectin 2) |
| 12 | HSPSCYWLGEDQVTYSEARRLCTDHGSQLVTITNRFEQAFVSSLIYNWEGEYFW TALQDLNSTGSFFWLSGDEVMYTHWNRDQPGYSRGGCVALATGSAMGLWEVKNC TSFRARYIC | D5 (C-type lectin 3) |
| 13 | KLRYCYKVFSSERLQDKKSWVQAQGACQELGAQLLSLASYEEEHFVANMLNKIF GESEPEIHEQHWFWIGLNRRDPRGGQSWRWSDGVGFSYHNFDRSRHDDDDIRGC AVLDLASLQWVAMQCDTQLDWICK | D6 (C-type lectin 4) |
| 14 | FQEAEYKFFEHHSTWAQAQRICTWFQAELTSVHSQAELDFLSHNLQKESRAQEQ HWWIGLHTSESDGRFRWTDGSIINFISWAPGKPRPVGKDKKCVYMTASREDWGD QRCLTALPYICK | D7 (C-type lectin 5) |
| 15 | FLNKCFQVQGQEPQSRVKWSEAQFSCEQQEAQLVTITNPLEQAFITASLPNVTF DLWIGLHASQRDFQWVEQEPLMYANWAPGEPSGPSPAPSGNKPTSCAVVLHSPS AHFTGRWDDRSCTEETHGFIC | D8 (C-type lectin 6) |
| 16 | YLNGTFRLLQKPLRWHDALLLCESRNASLAYVPDPYTQAFLTQAARGLRTPLWI GLAGEEGSRRYSWVSEEPLNYVGWQDGEPQQPGGCTYVDVDGAWRTTSCDTKLQ GAVC | D9 (C-type lectin 7) |
| 17 | FREHCYSFHMELLLGHKEARQRCQRAGGAVLSILDEMENVFVWEHLQSYEGQSR GAWLGMNFNPKGGTLVWQDNTAVNYSNWGPPGLGPSMLSHNSCYWIQSNSGLWR PGACTNITMGVVC | D10 (C-type lectin 8) |
| 18 | NGLPGPIGPPGPRGRTGDAGPVGPPGPPGPPGPPGPPSAGFDFSFLPQPPQEKA HDGGRYYRANDANVVRDRDLEVDTTLKSLSQQIENIRSPEGSRKNPARTCRDLK MCHSDWKSGEYWIDPNQGCNLDAIKVFCNMETGETCVYPTQPSVAQKNWYISKN PKDKRHVWFGESMTDGFQFEYGGQGSDPADVAIQLTFLRLMSTEASQNITYHCK NSVAYMDQQTGNLKKALLLKGSNEIEIRAEGNSRFTYSVTVDGCTSHTGAWGKT VIEYKTTKSSRLPIIDVAPLDVGAPDQEFGFDVGPVCFL | Trimerization peptide (Type I) with glycine-X-Y repeats and D→N mutation at BMP-1 site, KS version |
| 19 | NGLPGPIGPPGPRGRTGDAGPVGPPGPPGPPGPPGPPSAGFDFSFLPQPPQEKA HDGGRYYRNDDANVVRDRDLEVDTTLKSLSQQIENIRSPEGSRKNPARTCRDLK MCHSDWKSGEYWIDPNQGCNLDAIKVFCNMETGETCVYPTQPSVAQKNWYISKN PKDKRHVWFGESMTDGFQFEYGGQGSDPADVAIQLTFLRLMSTEASQNITYHCK NSVAYMDQQTGNLKKALLLKGSNEIEIRAEGNSRFTYSVTVDGCTSHTGAWGKT VIEYKTTKSSRLPIIDVAPLDVGAPDQEFGFDVGPVCFL | Trimerization peptide (Type I) with glycine-X-Y repeats and A→N mutation at BMP-1 site, KS version |
| 20 | RSNGLPGPIGPPGPRGRTGDAGPVGPPGPPGPPGPPGPPSAGFDFSFLPQPPQE KAHDGGRYYRANDANVVRDRDLEVDTTLKSLSQQIENIRSPEGSRKNPARTCRD LKMCHSDWKSGEYWIDPNQGCNLDAIKVFCNMETGETCVYPTQPSVAQKNWYIS KNPKDKRHVWFGESMTDGFQFEYGGQGSDPADVAIQLTFLRLMSTEASQNITYH CKNSVAYMDQQTGNLKKALLLKGSNEIEIRAEGNSRFTYSVTVDGCTSHTGAWG KTVIEYKTTKSSRLPIIDVAPLDVGAPDQEFGFDVGPVCFL | Trimerization peptide (Type I) with glycine-X-Y repeats and D→N mutation at BMP-1 site, KS version |
| 21 | GSNGLPGPIGPPGPRGRTGDAGPVGPPGPPGPPGPPGPPSAGFDFSFLPQPPQE KAHDGGRYYRANDANVVRDRDLEVDTTLKSLSQQIENIRSPEGSRKNPARTCRD LKMCHSDWKSGEYWIDPNQGCNLDAIKVFCNMETGETCVYPTQPSVAQKNWYIS KNPKDKRHVWFGESMTDGFQFEYGGQGSDPADVAIQLTFLRLMSTEASQNITYH CKNSVAYMDQQTGNLKKALLLKGSNEIEIRAEGNSRFTYSVTVDGCTSHTGAWG KTVIEYKTTKSSRLPIIDVAPLDVGAPDQEFGFDVGPVCFL | Trimerization peptide (Type I) with glycine-X-Y repeats and D→N mutation at BMP-1 site, KS version |
| 22 | NGLPGPIGPPGPRGRTGDAGPVGPPGPPGPPGPPGPPSAGFDFSFLPQPPQEKA HDGGRYYRADDANVVRDRDLEVDTTLKSLSQQIENIRSPEGSRKNPARTCRDLK MCHSDWKSGEYWIDPNQGCNLDAIKVFCNMETGETCVYPTQPSVAQKNWYISKN PKDKRHVWFGESMTDGFQFEYGGQGSDPADVAIQLTFLRLMSTEASQNITYHCK NSVAYMDQQTGNLKKALLLKGSNEIEIRAEGNSRFTYSVTVDGCTSHTGAWGKT VIEYKTTKSSRLPIIDVAPLDVGAPDQEFGFDVGPVCFL | Trimerization peptide (Type I) with glycine-X-Y repeats, no BMP-1 site mutation, KS version |

-continued

| SEQUENCE LISTING | | |
|---|---|---|
| SEQ ID | SEQUENCE | ANNOTATION |
| 23 | SNGLPGPIGPPGPRGRTGDAGPVGPPGPPGPPGPGPPSAGFDFSFLPQPPQEK<br>AHDGGRYYRADDANVVRDRDLEVDTTLKSLSQQIENIRSPEGSRKNPARTCRDL<br>KMCHSDWKSGEYWIDPNQGCNLDAIKVFCNMETGETCVYPTQPSVAQKNWYISK<br>NPKDKRHVWFGESMTDGFQFEYGGQGSDPADVAIQLTFLRLMSTEASQNITYHC<br>KNSVAYMDQQTGNLKKALLLKGSNEIEIRAEGNSRFTYSVTVDGCTSHTGAWGK<br>TVIEYKTTKSSRLPIIDVAPLDVGAPDQEFGFDVGPVCFL | Trimerization<br>peptide (Type I)<br>with glycine-X-Y<br>repeats, no BMP-<br>1 site mutation,<br>KS version |
| 24 | NGLPGPIGPPGPRGRTGDAGPVGPPGPPGPPGPPGPPSAGFDFSFLPQPPQEKA<br>HDGGRYYRADDANVVRDRDLEVDTTLKSLSQQIENIRSPEGSRKNPARTCRDLK<br>MCHSDWKSGEYWIDPNQGCNLDAIKVFCNMETGETCVYPTQPSVAQKNWYISKN<br>PKDKRHVWFGESMTDGFQFEYGGQGSDPADVAIQLTFLRLMSTEASQNITYHCK<br>NSVAYMDQQTGNLKKALLLQGSNEIEIRAEGNSRFTYSVTVDGCTSHTGAWGKT<br>VIEYKTTKTSRLPIIDVAPLDVGAPDQEFGFDVGPVCFL | Trimerization<br>peptide (Type I)<br>with glycine-X-Y<br>repeats, no BMP-<br>1 site mutation,<br>QT version |
| 25 | SNGLPGPIGPPGPRGRTGDAGPVGPPGPPGPPGPGPPSAGFDFSFLPQPPQEK<br>AHDGGRYYRADDANVVRDRDLEVDTTLKSLSQQIENIRSPEGSRKNPARTCRDL<br>KMCHSDWKSGEYWIDPNQGCNLDAIKVFCNMETGETCVYPTQPSVAQKNWYISK<br>NPKDKRHVWFGESMTDGFQFEYGGQGSDPADVAIQLTFLRLMSTEASQNITYHC<br>KNSVAYMDQQTGNLKKALLLQGSNEIEIRAEGNSRFTYSVTVDGCTSHTGAWGK<br>TVIEYKTTKTSRLPIIDVAPLDVGAPDQEFGFDVGPVCFL | Trimerization<br>peptide (Type I)<br>with glycine-X-Y<br>repeats, no BMP-<br>1 site mutation,<br>QT version |
| 26 | ANVVRDRDLEVDTTLKSLSQQIENIRSPEGSRKNPARTCRDLKMCHSDWKSGEY<br>WIDPNQGCNLDAIKVFCNMETGETCVYPTQPSVAQKNWYISKNPKDKRHVWFGE<br>SMTDGFQFEYGGQGSDPADVAIQLTFLRLMSTEASQNITYHCKNSVAYMDQQTG<br>NLKKALLLKGSNEIEIRAEGNSRFTYSVTVDGCTSHTGAWGKTVIEYKTTKSSR<br>LPIIDVAPLDVGAPDQEFGFDVGPVCFL | Trimerization<br>peptide (Type<br>I), KS version |
| 27 | DANVVRDRDLEVDTTLKSLSQQIENIRSPEGSRKNPARTCRDLKMCHSDWKSGE<br>YWIDPNQGCNLDAIKVFCNMETGETCVYPTQPSVAQKNWYISKNPKDKRHVWFG<br>ESMTDGFQFEYGGQGSDPADVAIQLTFLRLMSTEASQNITYHCKNSVAYMDQQT<br>GNLKKALLLKGSNEIEIRAEGNSRFTYSVTVDGCTSHTGAWGKTVIEYKTTKSS<br>RLPIIDVAPLDVGAPDQEFGFDVGPVCF | Trimerization<br>peptide (Type<br>I), KS version |
| 28 | SDANVVRDRDLEVDTTLKSLSQQIENIRSPEGSRKNPARTCRDLKMCHSDWKSG<br>EYWIDPNQGCNLDAIKVFCNMETGETCVYPTQPSVAQKNWYISKNPKDKRHVWF<br>GESMTDGFQFEYGGQGSDPADVAIQLTFLRLMSTEASQNITYHCKNSVAYMDQQ<br>TGNLKKALLLKGSNEIEIRAEGNSRFTYSVTVDGCTSHTGAWGKTVIEYKTTKS<br>SRLPIIDVAPLDVGAPDQEFGFDVGPVCFL | Trimerization<br>peptide (Type<br>I), KS version |
| 29 | RSDANVVRDRDLEVDTTLKSLSQQIENIRSPEGSRKNPARTCRDLKMCHSDWKS<br>GEYWIDPNQGCNLDAIKVFCNMETGETCVYPTQPSVAQKNWYISKNPKDKRHVW<br>FGESMTDGFQFEYGGQGSDPADVAIQLTFLRLMSTEASQNITYHCKNSVAYMDQ<br>QTGNLKKALLLKGSNEIEIRAEGNSRFTYSVTVDGCTSHTGAWGKTVIEYKTTK<br>SSRLPIIDVAPLDVGAPDQEFGFDVGPVCFL | Trimerization<br>peptide (Type<br>I), KS version |
| 30 | NGLPGPIGPPGPRGRTGDAGPVGPPGPPGPPGPPGPPSAGFDFSFLPQPPQEKA<br>HDGGRYYRANDANVVRDRDLEVDTTLKSLSQQIENIRSPEGSRKNPARTCRDLK<br>MCHSDWKSGEYWIDPNQGCNLDAIKVFCNMETGETCVYPTQPSVAQKNWYISKN<br>PKDKRHVWFGESMTDGFQFEYGGQGSDPADVAIQLTFLRLMSTEASQNITYHCK<br>NSVAYMDQQTGNLKKALLLQGSNEIEIRAEGNSRFTYSVTVDGCTSHTGAWGKT<br>VIEYKTTKTSRLPIIDVAPLDVGAPDQEFGFDVGPVCFL | Trimerization<br>peptide (Type<br>I), with<br>glycine-X-Y<br>repeats and D→N<br>mutation at BMP-<br>1 site, QT<br>version |
| 31 | NGLPGPIGPPGPRGRTGDAGPVGPPGPPGPPGPPGPPSAGFDFSFLPQPPQEKA<br>HDGGRYYRNDDANVVRDRDLEVDTTLKSLSQQIENIRSPEGSRKNPARTCRDLK<br>MCHSDWKSGEYWIDPNQGCNLDAIKVFCNMETGETCVYPTQPSVAQKNWYISKN<br>PKDKRHVWFGESMTDGFQFEYGGQGSDPADVAIQLTFLRLMSTEASQNITYHCK<br>NSVAYMDQQTGNLKKALLLQGSNEIEIRAEGNSRFTYSVTVDGCTSHTGAWGKT<br>VIEYKTTKTSRLPIIDVAPLDVGAPDQEFGFDVGPVCFL | Trimerization<br>peptide (Type<br>I), with<br>glycine-X-Y<br>repeats and A→N<br>mutation at BMP-<br>1 site, QT<br>version |
| 32 | RSNGLPGPIGPPGPRGRTGDAGPVGPPGPPGPPGPGPPSAGFDFSFLPQPPQE<br>KAHDGGRYYRANDANVVRDRDLEVDTTLKSLSQQIENIRSPEGSRKNPARTCRD<br>LKMCHSDWKSGEYWIDPNQGCNLDAIKVFCNMETGETCVYPTQPSVAQKNWYIS<br>KNPKDKRHVWFGESMTDGFQFEYGGQGSDPADVAIQLTFLRLMSTEASQNITYH<br>CKNSVAYMDQQTGNLKKALLLQGSNEIEIRAEGNSRFTYSVTVDGCTSHTGAWG<br>KTVIEYKTTKTSRLPIIDVAPLDVGAPDQEFGFDVGPVCFL | Trimerization<br>peptide (Type<br>I), with<br>glycine-X-Y<br>repeats and D→N<br>mutation at BMP-<br>1 site, QT<br>version |

| SEQUENCE LISTING | | |
|---|---|---|
| SEQ ID | SEQUENCE | ANNOTATION |
| 33 | GSNGLPGPIGPPGPRGRTGDAGPVGPPGPPGPPGPPGPPSAGFDFSFLPQPPQE KAHDGGRYYRANDANVVRDRDLEVDTTLKSLSQQIENIRSPEGSRKNPARTCRD LKMCHSDWKSGEYWIDPNQGCNLDAIKVFCNMETGETCVYPTQPSVAQKNWYIS KNPKDKRHVWFGESMTDGFQFEYGGQGSDPADVAIQLTFLRLMSTEASQNITYH CKNSVAYMDQQTGNLKKALLLQGSNEIEIRAEGNSRFTYSVTVDGCTSHTGAWG KTVIEYKTTKTSRLPIIDVAPLDVGAPDQEFGFDVGPVCFL | Trimerization peptide (Type I), with glycine-X-Y repeats and D→N mutation at BMP-1 site, QT version |
| 34 | DEIMTSLKSVNGQIESLISPDGSRKNPARNCRDLKFCHPELKSGEYWVDPNQGC KLDAIKVFCNMETGETCISANPLNVPRKHWWTDSSAEKKHVWFGESMDGGFQFS YGNPELPEDVLDVQLAFLRLLSSRASQNITYHCKNSIAYMDQASGNVKKALKLM GSNEGEFKAEGNSKFTYTVLEDGCTKHTGEWSKTVFEYRTRKAVRLPIVDIAPY DIGGPDQEFGVDVGPVCF | Trimerization peptide (Type III) |
| 35 | EPMDFKINTDEIMTSLKSVNGQIESLISPDGSRKNPARNCRDLKFCHPELKSGE YWVDPNQGCKLDAIKVFCNMETGETCISANPLNVPRKHWWTDSSAEKKHVWEGE SMDGGFQFSYGNPELPEDVLDVQLAFLRLLSSRASQNITYHCKNSIAYMDQASG NVKKALKLMGSNEGEFKAEGNSKFTYTVLEDGCTKHTGEWSKTVFEYRTRKAVR LPIVDIAPYDIGGPDQEFGVDVGPVCFL | Trimerization peptide (Type III) |
| 36 | SEPMDFKINTDEIMTSLKSVNGQIESLISPDGSRKNPARNCRDLKFCHPELKSG EYWVDPNQGCKLDAIKVFCNMETGETCISANPLNVPRKHWWTDSSAEKKHVWFG ESMDGGFQFSYGNPELPEDVLDVQLAFLRLLSSRASQNITYHCKNSIAYMDQAS GNVKKALKLMGSNEGEFKAEGNSKFTYTVLEDGCTKHTGEWSKTVFEYRTRKAV RLPIVDIAPYDIGGPDQEFGVDVGPVCFL | Trimerization peptide (Type III) |
| 37 | RSEPMDFKINTDEIMTSLKSVNGQIESLISPDGSRKNPARNCRDLKFCHPELKS GEYWVDPNQGCKLDAIKVFCNMETGETCISANPLNVPRKHWWTDSSAEKKHVWF GESMDGGFQFSYGNPELPEDVLDVQLAFLRLLSSRASQNITYHCKNSIAYMDQA SGNVKKALKLMGSNEGEFKAEGNSKFTYTVLEDGCTKHTGEWSKTVFEYRTRKA VRLPIVDIAPYDIGGPDQEFGVDVGPVCFL | Trimerization peptide (Type III) |
| 38 | ANVVRDRDLEVDTTLKSLSQQIENIRSPEGSRKNPARTCRDLKMCHSDWKSGEY WIDPNQGCNLDAIKVFCNMETGETCVYPTQPSVAQKNWYISKNPKDKRHVWFGE SMTDGFQFEYGGQGSDPADVAIQLTFLRLMSTEASQNITYHCKNSVAYMDQQTG NLKKALLLQGSNEIEIRAEGNSRFTYSVTVDGCTSHTGAWGKTVIEYKTTKTSR LPIIDVAPLDVGAPDQEFGFDVGPVCFL | Trimerization peptide (Type I), QT version |
| 39 | SDANVVRDRDLEVDTTLKSLSQQIENIRSPEGSRKNPARTCRDLKMCHSDWKSG EYWIDPNQGCNLDAIKVFCNMETGETCVYPTQPSVAQKNWYISKNPKDKRHVWF GESMTDGFQFEYGGQGSDPADVAIQLTFLRLMSTEASQNITYHCKNSVAYMDQQ TGNLKKALLLQGSNEIEIRAEGNSRFTYSVTVDGCTSHTGAWGKTVIEYKTTKT SRLPIIDVAPLDVGAPDQEFGFDVGPVCFL | Trimerization peptide (Type I), QT version |
| 40 | RSDANVVRDRDLEVDTTLKSLSQQIENIRSPEGSRKNPARTCRDLKMCHSDWKS GEYWIDPNQGCNLDAIKVFCNMETGETCVYPTQPSVAQKNWYISKNPKDKRHVV FGESMTDGFQFEYGGQGSDPADVAIQLTFLRLMSTEASQNITYHCKNSVAYMDQ QTGNLKKALLLQGSNEIEIRAEGNSRFTYSVTVDGCTSHTGAWGKTVIEYKTTK TSRLPIIDVAPLDVGAPDQEFGFDVGPVCFL | Trimerization peptide (Type I), QT version |
| 41 | GSDANVVRDRDLEVDTTLKSLSQQIENIRSPEGSRKNPARTCRDLKMCHSDWKS GEYWIDPNQGCNLDAIKVFCNMETGETCVYPTQPSVAQKNWYISKNPKDKRHVV FGESMTDGFQFEYGGQGSDPADVAIQLTFLRLMSTEASQNITYHCKNSVAYMDQ QTGNLKKALLLQGSNEIEIRAEGNSRFTYSVTVDGCTSHTGAWGKTVIEYKTTK TSRLPIIDVAPLDVGAPDQEFGFDVGPVCFL | Trimerization peptide (Type I), QT version |
| 42 | RVEPKSCDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGKEYKC KVSNKALPAPIEKTISKAKGQPREPQVYTLPPSRDELTKNQVSLTCLVKGFYPS DIAVEWESNGQPENNYKTTPPVLDSDGSFFLYSKLTVDKSRWQQGNVFSCSVMH EALHNHYTQKSLSLSPGK | Fc |
| 43 | MGPGRPAPAPWPRHLLRCVLLLGCLHLGRPGAPGDAALPEPNVFLIFSHGLQGC LEAQGGQVRVTPACNTSLPAQRWKWVSRNRLFNLGTMQCLGTGWPGTNTTASLG MYECDREALNLRWHCRTLGDQLSLLLGARTSNISKPGTLERGDQTRSGQWRIYG SEEDLCALPYHEVYTIQGNSHGKPCTIPFKYDNQWFHGCTSTGREDGHLWCATT QDYGKDERWGFCPIKSNDCETFWDKDQLTDSCYQFNFQSTLSWREAWASCEQQG ADLLSITEIHEQTYINGLLTGYSSTLWIGLNDLDTSGGWQWSDNSPLKYLNWES DQPDNPSEENCGVIRTESSGGWQNRDCSIALPYVCKKKPNATAEPTPPDRWANV KVECEPSWQPFQGHCYRLQAEKRSWQESKKACLRGGGDLVSIHSMAELEFITKQ IKQEVEELWIGLNDLKLQMNFEWSDGSLVSFTHWHPFEPNNERDSLEDCVTIWG PEGRWNDSPCNQSLPSICKKAGQLSQGAAEEDHGCRKGWTWHSPSCYWLGEDQV TYSEARRLCTDHGSQLVTITNRFEQAFVSSLIYNWEGEYFWTALQDLNSTGSFF | Full length Endo180-Fc (D1-10-Fc) |

| SEQ ID | SEQUENCE | ANNOTATION |
|---|---|---|
| | WLSGDEVMYTHWNRDQPGYSRGGCVALATGSAMGLWEVKNCTSFRARYICRQSL<br>GTPVTPELPGPDPTPSLTGSCPQGWASDTKLRYCYKVESSERLQDKSWVQAQG<br>ACQELGAQLLSLASYEEEHFVANMLNKIFGESEPEIHEQHWFWIGLNRRDPRGG<br>QSWRWSDGVGFSYHNFDRSRHDDDDIRGCAVLDLASLQWVAMCDTQLDWICKI<br>PRGTDVREPDDSPQGRREWLRFQEAEYKFFEHHSTWAQAQRICTWFQAELTSVH<br>SQAELDFLSHNLQKFSRAQEQHWWIGLHTSESDGRFRWTDGSIINFISWAPGKP<br>RPVGKDKKCVYMTASREDWGDQRCLTALPYICKRSNVTKETQPPDLPTTALGGC<br>PSDWIQFLNKCFQVQGQEPQSRVKWSEAQFSCEQQEAQLVTITNPLEQAFITAS<br>LPNVTFDLWIGLHASQRDFQWVEQEPLMYANWAPGEPSGPSPAPSGNKPTSCAV<br>VLHSPSAHFTGRWDDRSCTEETHGFICQKGTDPSLSPSPAALPPAPGTELSYLN<br>GTFRLLQKPLRWHDALLLCESRNASLAYVPDPYTQAFLTQAARGLRTPLWIGLA<br>GEEGSRRYSWVSEEPLNYVGWQDGEPQQPGGCTYVDVDGAWRTTSCDTKLQGAV<br>CGVSSGPPPPRRISYHGSCPQGLADSAWIPFREHCYSFHMELLLGHKEARQRCQ<br>RAGGAVLSILDEMENVFVWEHLQSYEGQSRGAWLGMNFNPKGGTLVWQDNTAVN<br>YSNWGPPGLGPSMLSHNSCYWIQSNSGLWRPGACTNITMGVVCKRVEPKSCDKT<br>HTCPPCPAPELLGGPSVFLFPPKPKDTLMISRTPEVTCVVVDVSHEDPEVKENW<br>YVDGVEVHNAKTKPREEQYNSTYRVVSVLTVLHQDWLNGKEYKCKVSNKALPAP<br>IEKTISKAKGQPREPQVYTLPPSRDELTKNQVSLTCLVKGFYPSDIAVEWESNG<br>QPENNYKTTPPVLDSDGSFFLYSKLTVDKSRWQQGNVFSCSVMHEALHNHYTQK<br>SLSLSPGK | |
| 44 | GAPGDAALPEPNVFLIFSHGLQGCLEAQGGQVRVTPACNTSLPAQRWKWVSRNR<br>LFNLGTMQCLGTGWPGTNTTASLGMYECDREALNLRWHCRTLGDQLSLLLGART<br>SNISKPGTLERGDQTRSGQWRIYGSEEDLCALPYHEVYTIQGNSHGKPCTIPFK<br>YDNQWFHGCTSTGREDGHLWCATTQDYGKDERWGFCPIKSNDCETFWDKDQLTD<br>SCYQFNFQSTLSWREAWASCEQQGADLLSITEIHEQTYINGLLTGYSSTLWIGL<br>NDLDTSGGWQWSDNSPLKYLNWESDQPDNPSEENCGVIRTESSGGWQNRDCSIA<br>LPYVCKKKPNATAEPTPPDRWANVKVECEPSWQPFQGHCYRLQAEKRSWQESKK<br>ACLRGGGDLVSIHSMAELEFITKQIKQEVEELWIGLNDLKLQMNFEWSDGSLVS<br>FTHWHPFEPNNERDSLEDCVTIWGPEGRWNDSPCNQSLPSICKKAGQLSQGAAE<br>EDHGCRKGWTWHSPSCYWLGEDQVTYSEARRLCTDHGSQLVTITNRFEQAFVSS<br>LIYNWEGEYFWTALQDLNSTGSFFWLSGDEVMYTHWNRDQPGYSRGGCVALATG<br>SAMGLWEVKNCTSFRARYICRQSLGTPVTPELPGPDPTPSLTGSCPQGWASDTK<br>LRYCYKVFSSERLQDKKSWVQAQGACQELGAQLLSLASYEEEHFVANMLNKIFG<br>ESEPEIHEQHWFWIGLNRRDPRGGQSWRWSDGVGFSYHNFDRSRHDDDDIRGCA<br>VLDLASLQWVAMCDTQLDWICKIPRGTDVREPDDSPQGRREWLRFQEAEYKFF<br>EHHSTWAQAQRICTWFQAELTSVHSQAELDFLSHNLQKFSRAQEQHWWIGLHTS<br>ESDGRFRWTDGSIINFISWAPGKPRPVGKDKKCVYMTASREDWGDQRCLTALPY<br>ICKRSNVTKETQPPDLPTTALGGCPSDWIQFLNKCFQVQGQEPQSRVKWSEAQF<br>SCEQQEAQLVTITNPLEQAFITASLPNVTFDLWIGLHASQRDFQWVEQEPLMYA<br>NWAPGEPSGPSPAPSGNKPTSCAVVLHSPSAHFTGRWDDRSCTEETHGFICQKG<br>TDPSLSPSPAALPPAPGTELSYLNGTFRLLQKPLRWHDALLLCESRNASLAYVP<br>DPYTQAFLTQAARGLRTPLWIGLAGEEGSRRYSWVSEEPLNYVGWQDGEPQQPG<br>GCTYVDVDGAWRTTSCDTKLQGAVCGVSSGPPPPRRISYHGSCPQGLADSAWIP<br>FREHCYSFHMELLLGHKEARQRCQRAGGAVLSILDEMENVFVWEHLQSYEGQSR<br>GAWLGMNFNPKGGTLVWQDNTAVNYSNWGPPGLGPSMLSHNSCYWIQSNSGLWR<br>PGACTNITMGVVCKRVEPKSCDKTHTCPPCPAPELLGGPSVFLFPPKPKDTLMI<br>SRTPEVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTVDKS<br>RWQQGNVFSCSVMHEALHNHYTQKSLSLSPGK | Mature Endo-180-<br>Fc (D1-10-Fc) |
| 45 | MGPGRPAPAPWPRHLLRCVLLLGCLHLGRPRSPVTPELPGPDPTPSLTGSCPQG<br>WASDTKLRYCYKVFSSERLQDKKSWVQAQGACQELGAQLLSLASYEEEHFVANM<br>LNKIFGESEPEIHEQHWFWIGLNRRDPRGGQSWRWSDGVGFSYHNFDRSRHDDD<br>DIRGCAVLDLASLQWVAMCDTQLDWICKIPRVEPKSCDKTHTCPPCPAPELLG<br>GPSVFLFPPKPKDTLMISRTPEVTCVVVDVSHEDPEVKENWYVDGVEVHNAKTK<br>PREEQYNSTYRVVSVLTVLHQDWLNGKEYKCKVSNKALPAPIEKTISKAKGQPR<br>EPQVYTLPPSRDELTKNQVSLTCLVKGFYPSDIAVEWESNGQPENNYKTTPPVL<br>DSDGSFFLYSKLTVDKSRWQQGNVFSCSVMHEALHNHYTQKSLSLSPGK | Full Length D6-<br>Fc |
| 46 | RSPVTPELPGPDPTPSLTGSCPQGWASDTKLRYCYKVFSSERLQDKKSWVQAQG<br>ACQELGAQLLSLASYEEEHFVANMLNKIFGESEPEIHEQHWFWIGLNRRDPRGG<br>QSWRWSDGVGFSYHNFDRSRHDDDDIRGCAVLDLASLQWVAMCDTQLDWICKI<br>PRVEPKSCDKTHTCPPCPAPELLGGPSVFLFPPKPKDTLMISRTPEVTCVVVDV<br>SHEDPEVKFNWYVDGVEVHNAKTKPREEQYNSTYRVVSVLTVLHQDWLNGKEYK<br>CKVSNKALPAPIEKTISKAKGQPREPQVYTLPPSRDELTKNQVSLTCLVKGFYP<br>SDIAVEWESNGQPENNYKTTPPVLDSDGSFFLYSKLTVDKSRWQQGNVFSCSVM<br>HEALHNHYTQKSLSLSPGK | Mature D6-Fc |

The invention claimed is:

1. A method for purifying a secreted trimeric fusion protein from a sample, comprising:

(a) contacting a sample comprising the secreted trimeric fusion protein with a soluble Endo180 polypeptide linked to a support, wherein the trimeric fusion protein comprises a heterologous polypeptide sequence fused to a C-terminal polypeptide sequence of a procollagen, and wherein the soluble Endo180 polypeptide specifically binds to the C-terminal polypeptide sequence of the procollagen, whereby the secreted trimeric fusion protein and the soluble Endo180 polypeptide form a complex on the support;

(b) removing unbound and/or nonspecifically bound molecules from the complex; and (c) dissociating the complex to release the trimeric fusion protein, thereby purifying the secreted trimeric fusion protein from the sample.

2. The method of claim 1, wherein the secreted trimeric fusion protein is encoded by a recombinant polynucleotide sequence comprising a polynucleotide sequence encoding the heterologous polypeptide sequence fused in-frame to C-terminal polypeptide sequence of the procollagen.

3. The method of claim 1, wherein the soluble Endo180 polypeptide is a fusion polypeptide comprising an immunoglobulin IgG Fc.

4. The method of claim 1, wherein the support comprises a resin, a particle, a bead, a solid substrate, a membrane, or a combination thereof, with or without Protein A covalently linked.

5. The method of claim 1, wherein the removing comprises washing the complex with a buffer.

6. The method of claim 1, wherein the dissociating comprises eluting the trimeric fusion protein from the complex with a buffer having increasing salt concentrations.

7. The method of claim 1, wherein the soluble Endo180 polypeptide is immobilized on the support via being either covalently linked to the support or non-covalently linked to the support via a Protein A binding.

8. The method of claim 7, wherein the soluble Endo180 polypeptide comprises an immunoglobulin IgG Fc region, wherein the soluble Endo180 polypeptide is non-covalently linked to a Protein A resin via specific binding of Protein A to the Fc region.

9. The method of claim 1, wherein the soluble Endo180 polypeptide comprises an ecto-domain of Endo180 or a fragment thereof, wherein the fragment comprises Domain D6 of Endo180.

10. The method of claim 9, wherein the ecto-domain of Endo180 or the fragment thereof comprises Domains D6, D1-6, D2-6, D3-6, D4-6, D5-6, D1-7, D2-7, D3-7, D4-7, D5-7, D6-7, D1-8, D2-8, D3-8, D4-8, D5-8, D6-8, D1-9, D2-9, D3-9, D4-9, D5-9, D6-9, D1-10, D2-10, D3-10, D4-10, D5-10 or D6-10 of Endo180.

11. The method of claim 9, wherein the soluble Endo180 polypeptide is an immunoglobulin IgG Re fusion protein.

12. The method of claim 9, wherein the ecto-domain of Endo180 or the fragment thereof comprises a sequence at least 70%, at least 75%, at least 80%, at least 85%, at least 90%, at least 95%, at least 99%, or 100% identical to SEQ ID NO: 1, SEQ ID NO: 2, SEQ ID NO: 43, es-SEQ ID NO: 44, SEQ ID NO; 3, SEQ ID NO: 4, SEQ ID NO: 45, or SEQ ID NO: 46.

13. The method of claim 1, wherein the heterologous polypeptide sequence comprises a TRAIL protein or fragment thereof, a 4-1-BBL protein or fragment thereof, an OX40L protein or fragment thereof, or a viral protein or fragment thereof.

14. The method of claim 13, wherein the viral protein is selected from the group consisting of antigens from HIV, an RSV, a coronavirus, an influenza virus, and a rabies virus.

15. The method of claim 14, wherein the coronavirus is a SARS-CoV-2.

16. The method of claim 1, wherein the C-terminal polypeptide sequence is from human procollagen.

17. The method of claim 1, wherein the procollagen is selected from the group consisting of proal(I), proal(II), proal(III), proal(V), proal(XI), proa2, proa2(V), proa2(XI), and proa3(XI).

* * * * *

SEQUENCE LISTING

<160> NUMBER OF SEQ ID NOS: 46

<210> SEQ ID NO 1
<211> LENGTH: 1632
<212> TYPE: PRT
<213> ORGANISM: Artificial Sequence
<220> FEATURE:
<223> OTHER INFORMATION: Full length Endo180-Fc (D1-10-Fc)

<400> SEQUENCE: 1

```
Met Gly Pro Gly Arg Pro Ala Pro Ala Pro Trp Pro Arg His Leu Leu
1               5                   10                  15

Arg Cys Val Leu Leu Leu Gly Cys Leu His Leu Gly Arg Pro Gly Ala
            20                  25                  30

Pro Gly Asp Ala Ala Leu Pro Glu Pro Asn Val Phe Leu Ile Phe Ser
        35                  40                  45

His Gly Leu Gln Gly Cys Leu Glu Ala Gln Gly Gly Gln Val Arg Val
    50                  55                  60

Thr Pro Ala Cys Asn Thr Ser Leu Pro Ala Gln Arg Trp Lys Trp Val
65                  70                  75                  80

Ser Arg Asn Arg Leu Phe Asn Leu Gly Thr Met Gln Cys Leu Gly Thr
                85                  90                  95

Gly Trp Pro Gly Thr Asn Thr Thr Ala Ser Leu Gly Met Tyr Glu Cys
            100                 105                 110

Asp Arg Glu Ala Leu Asn Leu Arg Trp His Cys Arg Thr Leu Gly Asp
            115                 120                 125

Gln Leu Ser Leu Leu Leu Gly Ala Arg Thr Ser Asn Ile Ser Lys Pro
    130                 135                 140

Gly Thr Leu Glu Arg Gly Asp Gln Thr Arg Ser Gly Gln Trp Arg Ile
145                 150                 155                 160

Tyr Gly Ser Glu Glu Asp Leu Cys Ala Leu Pro Tyr His Glu Val Tyr
                165                 170                 175

Thr Ile Gln Gly Asn Ser His Gly Lys Pro Cys Thr Ile Pro Phe Lys
            180                 185                 190

Tyr Asp Asn Gln Trp Phe His Gly Cys Thr Ser Thr Gly Arg Glu Asp
            195                 200                 205

Gly His Leu Trp Cys Ala Thr Thr Gln Asp Tyr Gly Lys Asp Glu Arg
    210                 215                 220

Trp Gly Phe Cys Pro Ile Lys Ser Asn Asp Cys Glu Thr Phe Trp Asp
225                 230                 235                 240

Lys Asp Gln Leu Thr Asp Ser Cys Tyr Gln Phe Asn Phe Gln Ser Thr
                245                 250                 255

Leu Ser Trp Arg Glu Ala Trp Ala Ser Cys Glu Gln Gln Gly Ala Asp
            260                 265                 270

Leu Leu Ser Ile Thr Glu Ile His Glu Gln Thr Tyr Ile Asn Gly Leu
            275                 280                 285

Leu Thr Gly Tyr Ser Ser Thr Leu Trp Ile Gly Leu Asn Asp Leu Asp
    290                 295                 300

Thr Ser Gly Gly Trp Gln Trp Ser Asp Asn Ser Pro Leu Lys Tyr Leu
305                 310                 315                 320

Asn Trp Glu Ser Asp Gln Pro Asp Asn Pro Ser Glu Glu Asn Cys Gly
                325                 330                 335

Val Ile Arg Thr Glu Ser Ser Gly Gly Trp Gln Asn Arg Asp Cys Ser
            340                 345                 350

Ile Ala Leu Pro Tyr Val Cys Lys Lys Lys Pro Asn Ala Thr Ala Glu
```

-continued

```
              355              360              365

Pro Thr Pro Pro Asp Arg Trp Ala Asn Val Lys Val Glu Cys Glu Pro
    370              375              380

Ser Trp Gln Pro Phe Gln Gly His Cys Tyr Arg Leu Gln Ala Glu Lys
385              390              395              400

Arg Ser Trp Gln Glu Ser Lys Lys Ala Cys Leu Arg Gly Gly Gly Asp
              405              410              415

Leu Val Ser Ile His Ser Met Ala Glu Leu Glu Phe Ile Thr Lys Gln
              420              425              430

Ile Lys Gln Glu Val Glu Glu Leu Trp Ile Gly Leu Asn Asp Leu Lys
              435              440              445

Leu Gln Met Asn Phe Glu Trp Ser Asp Gly Ser Leu Val Ser Phe Thr
    450              455              460

His Trp His Pro Phe Glu Pro Asn Asn Phe Arg Asp Ser Leu Glu Asp
465              470              475              480

Cys Val Thr Ile Trp Gly Pro Glu Gly Arg Trp Asn Asp Ser Pro Cys
              485              490              495

Asn Gln Ser Leu Pro Ser Ile Cys Lys Lys Ala Gly Gln Leu Ser Gln
              500              505              510

Gly Ala Ala Glu Glu Asp His Gly Cys Arg Lys Gly Trp Thr Trp His
              515              520              525

Ser Pro Ser Cys Tyr Trp Leu Gly Glu Asp Gln Val Thr Tyr Ser Glu
    530              535              540

Ala Arg Arg Leu Cys Thr Asp His Gly Ser Gln Leu Val Thr Ile Thr
545              550              555              560

Asn Arg Phe Glu Gln Ala Phe Val Ser Ser Leu Ile Tyr Asn Trp Glu
              565              570              575

Gly Glu Tyr Phe Trp Thr Ala Leu Gln Asp Leu Asn Ser Thr Gly Ser
              580              585              590

Phe Phe Trp Leu Ser Gly Asp Glu Val Met Tyr Thr His Trp Asn Arg
              595              600              605

Asp Gln Pro Gly Tyr Ser Arg Gly Gly Cys Val Ala Leu Ala Thr Gly
    610              615              620

Ser Ala Met Gly Leu Trp Glu Val Lys Asn Cys Thr Ser Phe Arg Ala
625              630              635              640

Arg Tyr Ile Cys Arg Gln Ser Leu Gly Thr Pro Val Thr Pro Glu Leu
              645              650              655

Pro Gly Pro Asp Pro Thr Pro Ser Leu Thr Gly Ser Cys Pro Gln Gly
              660              665              670

Trp Ala Ser Asp Thr Lys Leu Arg Tyr Cys Tyr Lys Val Phe Ser Ser
              675              680              685

Glu Arg Leu Gln Asp Lys Lys Ser Trp Val Gln Ala Gln Gly Ala Cys
              690              695              700

Gln Glu Leu Gly Ala Gln Leu Leu Ser Leu Ala Ser Tyr Glu Glu Glu
705              710              715              720

His Phe Val Ala Asn Met Leu Asn Lys Ile Phe Gly Glu Ser Glu Pro
              725              730              735

Glu Ile His Glu Gln His Trp Phe Trp Ile Gly Leu Asn Arg Arg Asp
              740              745              750

Pro Arg Gly Gly Gln Ser Trp Arg Trp Ser Asp Gly Val Gly Phe Ser
              755              760              765

Tyr His Asn Phe Asp Arg Ser Arg His Asp Asp Asp Ile Arg Gly
    770              775              780
```

-continued

```
Cys Ala Val Leu Asp Leu Ala Ser Leu Gln Trp Val Ala Met Gln Cys
785                 790                 795                 800

Asp Thr Gln Leu Asp Trp Ile Cys Lys Ile Pro Arg Gly Thr Asp Val
                805                 810                 815

Arg Glu Pro Asp Asp Ser Pro Gln Gly Arg Arg Glu Trp Leu Arg Phe
            820                 825                 830

Gln Glu Ala Glu Tyr Lys Phe Phe Glu His His Ser Thr Trp Ala Gln
        835                 840                 845

Ala Gln Arg Ile Cys Thr Trp Phe Gln Ala Glu Leu Thr Ser Val His
    850                 855                 860

Ser Gln Ala Glu Leu Asp Phe Leu Ser His Asn Leu Gln Lys Phe Ser
865                 870                 875                 880

Arg Ala Gln Glu Gln His Trp Trp Ile Gly Leu His Thr Ser Glu Ser
            885                 890                 895

Asp Gly Arg Phe Arg Trp Thr Asp Gly Ser Ile Ile Asn Phe Ile Ser
            900                 905                 910

Trp Ala Pro Gly Lys Pro Arg Pro Val Gly Lys Asp Lys Lys Cys Val
        915                 920                 925

Tyr Met Thr Ala Ser Arg Glu Asp Trp Gly Asp Gln Arg Cys Leu Thr
    930                 935                 940

Ala Leu Pro Tyr Ile Cys Lys Arg Ser Asn Val Thr Lys Glu Thr Gln
945                 950                 955                 960

Pro Pro Asp Leu Pro Thr Thr Ala Leu Gly Gly Cys Pro Ser Asp Trp
            965                 970                 975

Ile Gln Phe Leu Asn Lys Cys Phe Gln Val Gln Gly Gln Glu Pro Gln
            980                 985                 990

Ser Arg Val Lys Trp Ser Glu Ala  Gln Phe Ser Cys Glu  Gln Gln Glu
        995                 1000                1005

Ala Gln  Leu Val Thr Ile Thr  Asn Pro Leu Glu Gln  Ala Phe Ile
    1010                1015                1020

Thr Ala  Ser Leu Pro Asn Val  Thr Phe Asp Leu Trp  Ile Gly Leu
    1025                1030                1035

His Ala  Ser Gln Arg Asp Phe  Gln Trp Val Glu Gln  Glu Pro Leu
    1040                1045                1050

Met Tyr  Ala Asn Trp Ala Pro  Gly Glu Pro Ser Gly  Pro Ser Pro
    1055                1060                1065

Ala Pro  Ser Gly Asn Lys Pro  Thr Ser Cys Ala Val  Val Leu His
    1070                1075                1080

Ser Pro  Ser Ala His Phe Thr  Gly Arg Trp Asp Asp  Arg Ser Cys
    1085                1090                1095

Thr Glu  Glu Thr His Gly Phe  Ile Cys Gln Lys Gly  Thr Asp Pro
    1100                1105                1110

Ser Leu  Ser Pro Ser Pro Ala  Ala Leu Pro Pro Ala  Pro Gly Thr
    1115                1120                1125

Glu Leu  Ser Tyr Leu Asn Gly  Thr Phe Arg Leu Leu  Gln Lys Pro
    1130                1135                1140

Leu Arg  Trp His Asp Ala Leu  Leu Leu Cys Glu Ser  Arg Asn Ala
    1145                1150                1155

Ser Leu  Ala Tyr Val Pro Asp  Pro Tyr Thr Gln Ala  Phe Leu Thr
    1160                1165                1170

Gln Ala  Ala Arg Gly Leu Arg  Thr Pro Leu Trp Ile  Gly Leu Ala
    1175                1180                1185
```

-continued

```
Gly Glu  Glu Gly Ser Arg Arg  Tyr Ser Trp Val Ser  Glu Glu Pro
    1190             1195              1200

Leu Asn  Tyr Val Gly Trp Gln  Asp Gly Glu Pro Gln  Gln Pro Gly
    1205             1210              1215

Gly Cys  Thr Tyr Val Asp Val  Asp Gly Ala Trp Arg  Thr Thr Ser
    1220             1225              1230

Cys Asp  Thr Lys Leu Gln Gly  Ala Val Cys Gly Val  Ser Ser Gly
    1235             1240              1245

Pro Pro  Pro Pro Arg Arg Ile  Ser Tyr His Gly Ser  Cys Pro Gln
    1250             1255              1260

Gly Leu  Ala Asp Ser Ala Trp  Ile Pro Phe Arg Glu  His Cys Tyr
    1265             1270              1275

Ser Phe  His Met Glu Leu Leu  Leu Gly His Lys Glu  Ala Arg Gln
    1280             1285              1290

Arg Cys  Gln Arg Ala Gly Gly  Ala Val Leu Ser Ile  Leu Asp Glu
    1295             1300              1305

Met Glu  Asn Val Phe Val Trp  Glu His Leu Gln Ser  Tyr Glu Gly
    1310             1315              1320

Gln Ser  Arg Gly Ala Trp Leu  Gly Met Asn Phe Asn  Pro Lys Gly
    1325             1330              1335

Gly Thr  Leu Val Trp Gln Asp  Asn Thr Ala Val Asn  Tyr Ser Asn
    1340             1345              1350

Trp Gly  Pro Pro Gly Leu Gly  Pro Ser Met Leu Ser  His Asn Ser
    1355             1360              1365

Cys Tyr  Trp Ile Gln Ser Asn  Ser Gly Leu Trp Arg  Pro Gly Ala
    1370             1375              1380

Cys Thr  Asn Ile Thr Met Gly  Val Val Cys Lys Gln  Ala Tyr Val
    1385             1390              1395

Arg Ser  Glu Pro Lys Ser Cys  Asp Lys Thr His Thr  Cys Pro Pro
    1400             1405              1410

Cys Pro  Ala Pro Glu Leu Leu  Gly Gly Pro Ser Val  Phe Leu Phe
    1415             1420              1425

Pro Pro  Lys Pro Lys Asp Thr  Leu Met Ile Ser Arg  Thr Pro Glu
    1430             1435              1440

Val Thr  Cys Val Val Val Asp  Val Ser His Glu Asp  Pro Glu Val
    1445             1450              1455

Lys Phe  Asn Trp Tyr Val Asp  Gly Val Glu Val His  Asn Ala Lys
    1460             1465              1470

Thr Lys  Pro Arg Glu Glu Gln  Tyr Asn Ser Thr Tyr  Arg Val Val
    1475             1480              1485

Ser Val  Leu Thr Val Leu His  Gln Asp Trp Leu Asn  Gly Lys Glu
    1490             1495              1500

Tyr Lys  Cys Lys Val Ser Asn  Lys Ala Leu Pro Ala  Pro Ile Glu
    1505             1510              1515

Lys Thr  Ile Ser Lys Ala Lys  Gly Gln Pro Arg Glu  Pro Gln Val
    1520             1525              1530

Tyr Thr  Leu Pro Pro Ser Arg  Asp Glu Leu Thr Lys  Asn Gln Val
    1535             1540              1545

Ser Leu  Thr Cys Leu Val Lys  Gly Phe Tyr Pro Ser  Asp Ile Ala
    1550             1555              1560

Val Glu  Trp Glu Ser Asn Gly  Gln Pro Glu Asn Asn  Tyr Lys Thr
    1565             1570              1575

Thr Pro  Pro Val Leu Asp Ser  Asp Gly Ser Phe Phe  Leu Tyr Ser
```

```
            1580                1585                1590

Lys Leu  Thr Val Asp Lys Ser  Arg Trp Gln Gln Gly  Asn Val Phe
    1595                1600                1605

Ser Cys  Ser Val Met His Glu  Ala Leu His Asn His  Tyr Thr Gln
    1610                1615                1620

Lys Ser  Leu Ser Leu Ser Pro  Gly Lys
    1625                1630

<210> SEQ ID NO 2
<211> LENGTH: 1602
<212> TYPE: PRT
<213> ORGANISM: Artificial Sequence
<220> FEATURE:
<223> OTHER INFORMATION: Mature Endo-180-Fc(D1-10-Fc)

<400> SEQUENCE: 2

Gly Ala Pro Gly Asp Ala Ala Leu Pro Glu Pro Asn Val Phe Leu Ile
1               5                   10                  15

Phe Ser His Gly Leu Gln Gly Cys Leu Glu Ala Gln Gly Gly Gln Val
            20                  25                  30

Arg Val Thr Pro Ala Cys Asn Thr Ser Leu Pro Ala Gln Arg Trp Lys
        35                  40                  45

Trp Val Ser Arg Asn Arg Leu Phe Asn Leu Gly Thr Met Gln Cys Leu
    50                  55                  60

Gly Thr Gly Trp Pro Gly Thr Asn Thr Thr Ala Ser Leu Gly Met Tyr
65                  70                  75                  80

Glu Cys Asp Arg Glu Ala Leu Asn Leu Arg Trp His Cys Arg Thr Leu
                85                  90                  95

Gly Asp Gln Leu Ser Leu Leu Leu Gly Ala Arg Thr Ser Asn Ile Ser
            100                 105                 110

Lys Pro Gly Thr Leu Glu Arg Gly Asp Gln Thr Arg Ser Gly Gln Trp
        115                 120                 125

Arg Ile Tyr Gly Ser Glu Glu Asp Leu Cys Ala Leu Pro Tyr His Glu
    130                 135                 140

Val Tyr Thr Ile Gln Gly Asn Ser His Gly Lys Pro Cys Thr Ile Pro
145                 150                 155                 160

Phe Lys Tyr Asp Asn Gln Trp Phe His Gly Cys Thr Ser Thr Gly Arg
                165                 170                 175

Glu Asp Gly His Leu Trp Cys Ala Thr Thr Gln Asp Tyr Gly Lys Asp
            180                 185                 190

Glu Arg Trp Gly Phe Cys Pro Ile Lys Ser Asn Asp Cys Glu Thr Phe
        195                 200                 205

Trp Asp Lys Asp Gln Leu Thr Asp Ser Cys Tyr Gln Phe Asn Phe Gln
    210                 215                 220

Ser Thr Leu Ser Trp Arg Glu Ala Trp Ala Ser Cys Glu Gln Gln Gly
225                 230                 235                 240

Ala Asp Leu Leu Ser Ile Thr Glu Ile His Glu Gln Thr Tyr Ile Asn
                245                 250                 255

Gly Leu Leu Thr Gly Tyr Ser Ser Thr Leu Trp Ile Gly Leu Asn Asp
            260                 265                 270

Leu Asp Thr Ser Gly Gly Trp Gln Trp Ser Asp Asn Ser Pro Leu Lys
        275                 280                 285

Tyr Leu Asn Trp Glu Ser Asp Gln Pro Asp Asn Pro Ser Glu Glu Asn
    290                 295                 300

Cys Gly Val Ile Arg Thr Glu Ser Ser Gly Gly Trp Gln Asn Arg Asp
```

-continued

```
305                 310                 315                 320

Cys Ser Ile Ala Leu Pro Tyr Val Cys Lys Lys Lys Pro Asn Ala Thr
                325                 330                 335

Ala Glu Pro Thr Pro Pro Asp Arg Trp Ala Asn Val Lys Val Glu Cys
                340                 345                 350

Glu Pro Ser Trp Gln Pro Phe Gln Gly His Cys Tyr Arg Leu Gln Ala
                355                 360                 365

Glu Lys Arg Ser Trp Gln Glu Ser Lys Lys Ala Cys Leu Arg Gly Gly
        370                 375                 380

Gly Asp Leu Val Ser Ile His Ser Met Ala Glu Leu Glu Phe Ile Thr
385                 390                 395                 400

Lys Gln Ile Lys Gln Glu Val Glu Glu Leu Trp Ile Gly Leu Asn Asp
                405                 410                 415

Leu Lys Leu Gln Met Asn Phe Glu Trp Ser Asp Gly Ser Leu Val Ser
                420                 425                 430

Phe Thr His Trp His Pro Phe Glu Pro Asn Asn Phe Arg Asp Ser Leu
                435                 440                 445

Glu Asp Cys Val Thr Ile Trp Gly Pro Glu Gly Arg Trp Asn Asp Ser
        450                 455                 460

Pro Cys Asn Gln Ser Leu Pro Ser Ile Cys Lys Lys Ala Gly Gln Leu
465                 470                 475                 480

Ser Gln Gly Ala Ala Glu Glu Asp His Gly Cys Arg Lys Gly Trp Thr
                485                 490                 495

Trp His Ser Pro Ser Cys Tyr Trp Leu Gly Glu Asp Gln Val Thr Tyr
                500                 505                 510

Ser Glu Ala Arg Arg Leu Cys Thr Asp His Gly Ser Gln Leu Val Thr
        515                 520                 525

Ile Thr Asn Arg Phe Glu Gln Ala Phe Val Ser Ser Leu Ile Tyr Asn
        530                 535                 540

Trp Glu Gly Glu Tyr Phe Trp Thr Ala Leu Gln Asp Leu Asn Ser Thr
545                 550                 555                 560

Gly Ser Phe Phe Trp Leu Ser Gly Asp Glu Val Met Tyr Thr His Trp
                565                 570                 575

Asn Arg Asp Gln Pro Gly Tyr Ser Arg Gly Gly Cys Val Ala Leu Ala
                580                 585                 590

Thr Gly Ser Ala Met Gly Leu Trp Glu Val Lys Asn Cys Thr Ser Phe
                595                 600                 605

Arg Ala Arg Tyr Ile Cys Arg Gln Ser Leu Gly Thr Pro Val Thr Pro
        610                 615                 620

Glu Leu Pro Gly Pro Asp Pro Thr Pro Ser Leu Thr Gly Ser Cys Pro
625                 630                 635                 640

Gln Gly Trp Ala Ser Asp Thr Lys Leu Arg Tyr Cys Tyr Lys Val Phe
                645                 650                 655

Ser Ser Glu Arg Leu Gln Asp Lys Lys Ser Trp Val Gln Ala Gln Gly
                660                 665                 670

Ala Cys Gln Glu Leu Gly Ala Gln Leu Leu Ser Leu Ala Ser Tyr Glu
        675                 680                 685

Glu Glu His Phe Val Ala Asn Met Leu Asn Lys Ile Phe Gly Glu Ser
        690                 695                 700

Glu Pro Glu Ile His Glu Gln His Trp Phe Trp Ile Gly Leu Asn Arg
705                 710                 715                 720

Arg Asp Pro Arg Gly Gly Gln Ser Trp Arg Trp Ser Asp Gly Val Gly
                725                 730                 735
```

Phe Ser Tyr His Asn Phe Asp Arg Ser Arg His Asp Asp Asp Ile
            740                 745                 750

Arg Gly Cys Ala Val Leu Asp Leu Ala Ser Leu Gln Trp Val Ala Met
            755                 760                 765

Gln Cys Asp Thr Gln Leu Asp Trp Ile Cys Lys Ile Pro Arg Gly Thr
            770                 775                 780

Asp Val Arg Glu Pro Asp Asp Ser Pro Gln Gly Arg Arg Glu Trp Leu
785                 790                 795                 800

Arg Phe Gln Glu Ala Glu Tyr Lys Phe Phe Glu His His Ser Thr Trp
                805                 810                 815

Ala Gln Ala Gln Arg Ile Cys Thr Trp Phe Gln Ala Glu Leu Thr Ser
            820                 825                 830

Val His Ser Gln Ala Glu Leu Asp Phe Leu Ser His Asn Leu Gln Lys
            835                 840                 845

Phe Ser Arg Ala Gln Glu Gln His Trp Trp Ile Gly Leu His Thr Ser
    850                 855                 860

Glu Ser Asp Gly Arg Phe Arg Trp Thr Asp Gly Ser Ile Ile Asn Phe
865                 870                 875                 880

Ile Ser Trp Ala Pro Gly Lys Pro Arg Pro Val Gly Lys Asp Lys Lys
                885                 890                 895

Cys Val Tyr Met Thr Ala Ser Arg Glu Asp Trp Gly Asp Gln Arg Cys
                900                 905                 910

Leu Thr Ala Leu Pro Tyr Ile Cys Lys Arg Ser Asn Val Thr Lys Glu
            915                 920                 925

Thr Gln Pro Pro Asp Leu Pro Thr Thr Ala Leu Gly Gly Cys Pro Ser
    930                 935                 940

Asp Trp Ile Gln Phe Leu Asn Lys Cys Phe Gln Val Gln Gly Gln Glu
945                 950                 955                 960

Pro Gln Ser Arg Val Lys Trp Ser Glu Ala Gln Phe Ser Cys Glu Gln
                965                 970                 975

Gln Glu Ala Gln Leu Val Thr Ile Thr Asn Pro Leu Glu Gln Ala Phe
            980                 985                 990

Ile Thr Ala Ser Leu Pro Asn Val Thr Phe Asp Leu Trp Ile Gly Leu
    995                 1000                1005

His Ala Ser Gln Arg Asp Phe Gln Trp Val Glu Gln Glu Pro Leu
    1010                1015                1020

Met Tyr Ala Asn Trp Ala Pro Gly Glu Pro Ser Gly Pro Ser Pro
    1025                1030                1035

Ala Pro Ser Gly Asn Lys Pro Thr Ser Cys Ala Val Val Leu His
    1040                1045                1050

Ser Pro Ser Ala His Phe Thr Gly Arg Trp Asp Asp Arg Ser Cys
    1055                1060                1065

Thr Glu Glu Thr His Gly Phe Ile Cys Gln Lys Gly Thr Asp Pro
    1070                1075                1080

Ser Leu Ser Pro Ser Pro Ala Ala Leu Pro Pro Ala Pro Gly Thr
    1085                1090                1095

Glu Leu Ser Tyr Leu Asn Gly Thr Phe Arg Leu Leu Gln Lys Pro
    1100                1105                1110

Leu Arg Trp His Asp Ala Leu Leu Leu Cys Glu Ser Arg Asn Ala
    1115                1120                1125

Ser Leu Ala Tyr Val Pro Asp Pro Tyr Thr Gln Ala Phe Leu Thr
    1130                1135                1140

-continued

```
Gln Ala  Ala Arg Gly Leu Arg  Thr Pro Leu Trp Ile  Gly Leu Ala
    1145             1150              1155

Gly Glu  Glu Gly Ser Arg Arg  Tyr Ser Trp Val Ser  Glu Glu Pro
    1160             1165              1170

Leu Asn  Tyr Val Gly Trp Gln  Asp Gly Glu Pro Gln  Gln Pro Gly
    1175             1180              1185

Gly Cys  Thr Tyr Val Asp Val  Asp Gly Ala Trp Arg  Thr Thr Ser
    1190             1195              1200

Cys Asp  Thr Lys Leu Gln Gly  Ala Val Cys Gly Val  Ser Ser Gly
    1205             1210              1215

Pro Pro  Pro Pro Arg Arg Ile  Ser Tyr His Gly Ser  Cys Pro Gln
    1220             1225              1230

Gly Leu  Ala Asp Ser Ala Trp  Ile Pro Phe Arg Glu  His Cys Tyr
    1235             1240              1245

Ser Phe  His Met Glu Leu Leu  Leu Gly His Lys Glu  Ala Arg Gln
    1250             1255              1260

Arg Cys  Gln Arg Ala Gly Gly  Ala Val Leu Ser Ile  Leu Asp Glu
    1265             1270              1275

Met Glu  Asn Val Phe Val Trp  Glu His Leu Gln Ser  Tyr Glu Gly
    1280             1285              1290

Gln Ser  Arg Gly Ala Trp Leu  Gly Met Asn Phe Asn  Pro Lys Gly
    1295             1300              1305

Gly Thr  Leu Val Trp Gln Asp  Asn Thr Ala Val Asn  Tyr Ser Asn
    1310             1315              1320

Trp Gly  Pro Pro Gly Leu Gly  Pro Ser Met Leu Ser  His Asn Ser
    1325             1330              1335

Cys Tyr  Trp Ile Gln Ser Asn  Ser Gly Leu Trp Arg  Pro Gly Ala
    1340             1345              1350

Cys Thr  Asn Ile Thr Met Gly  Val Val Cys Lys Gln  Ala Tyr Val
    1355             1360              1365

Arg Ser  Glu Pro Lys Ser Cys  Asp Lys Thr His Thr  Cys Pro Pro
    1370             1375              1380

Cys Pro  Ala Pro Glu Leu Leu  Gly Gly Pro Ser Val  Phe Leu Phe
    1385             1390              1395

Pro Pro  Lys Pro Lys Asp Thr  Leu Met Ile Ser Arg  Thr Pro Glu
    1400             1405              1410

Val Thr  Cys Val Val Val Asp  Val Ser His Glu Asp  Pro Glu Val
    1415             1420              1425

Lys Phe  Asn Trp Tyr Val Asp  Gly Val Glu Val His  Asn Ala Lys
    1430             1435              1440

Thr Lys  Pro Arg Glu Glu Gln  Tyr Asn Ser Thr Tyr  Arg Val Val
    1445             1450              1455

Ser Val  Leu Thr Val Leu His  Gln Asp Trp Leu Asn  Gly Lys Glu
    1460             1465              1470

Tyr Lys  Cys Lys Val Ser Asn  Lys Ala Leu Pro Ala  Pro Ile Glu
    1475             1480              1485

Lys Thr  Ile Ser Lys Ala Lys  Gly Gln Pro Arg Glu  Pro Gln Val
    1490             1495              1500

Tyr Thr  Leu Pro Pro Ser Arg  Asp Glu Leu Thr Lys  Asn Gln Val
    1505             1510              1515

Ser Leu  Thr Cys Leu Val Lys  Gly Phe Tyr Pro Ser  Asp Ile Ala
    1520             1525              1530

Val Glu  Trp Glu Ser Asn Gly  Gln Pro Glu Asn Asn  Tyr Lys Thr
```

-continued
_____

```
        1535                1540                1545

Thr Pro  Pro Val Leu Asp Ser  Asp Gly Ser Phe Phe  Leu Tyr Ser
    1550                1555                1560

Lys Leu  Thr Val Asp Lys Ser  Arg Trp Gln Gln Gly  Asn Val Phe
    1565                1570                1575

Ser Cys  Ser Val Met His Glu  Ala Leu His Asn His  Tyr Thr Gln
    1580                1585                1590

Lys Ser  Leu Ser Leu Ser Pro  Gly Lys
    1595                1600

<210> SEQ ID NO 3
<211> LENGTH: 427
<212> TYPE: PRT
<213> ORGANISM: Artificial Sequence
<220> FEATURE:
<223> OTHER INFORMATION: Full Length D6-Fc

<400> SEQUENCE: 3

Met Gly Pro Gly Arg Pro Ala Pro Ala Pro Trp Pro Arg His Leu Leu
1               5                   10                  15

Arg Cys Val Leu Leu Leu Gly Cys Leu His Leu Gly Arg Pro Arg Ser
            20                  25                  30

Pro Val Thr Pro Glu Leu Pro Gly Pro Asp Pro Thr Pro Ser Leu Thr
        35                  40                  45

Gly Ser Cys Pro Gln Gly Trp Ala Ser Asp Thr Lys Leu Arg Tyr Cys
    50                  55                  60

Tyr Lys Val Phe Ser Ser Glu Arg Leu Gln Asp Lys Lys Ser Trp Val
65                  70                  75                  80

Gln Ala Gln Gly Ala Cys Gln Glu Leu Gly Ala Gln Leu Leu Ser Leu
                85                  90                  95

Ala Ser Tyr Glu Glu Glu His Phe Val Ala Asn Met Leu Asn Lys Ile
            100                 105                 110

Phe Gly Glu Ser Glu Pro Glu Ile His Glu Gln His Trp Phe Trp Ile
            115                 120                 125

Gly Leu Asn Arg Arg Asp Pro Arg Gly Gly Gln Ser Trp Arg Trp Ser
    130                 135                 140

Asp Gly Val Gly Phe Ser Tyr His Asn Phe Asp Arg Ser Arg His Asp
145                 150                 155                 160

Asp Asp Asp Ile Arg Gly Cys Ala Val Leu Asp Leu Ala Ser Leu Gln
                165                 170                 175

Trp Val Ala Met Gln Cys Asp Thr Gln Leu Asp Trp Ile Cys Lys Ile
            180                 185                 190

Pro Arg Ser Glu Pro Lys Ser Cys Asp Lys Thr His Thr Cys Pro Pro
            195                 200                 205

Cys Pro Ala Pro Glu Leu Leu Gly Gly Pro Ser Val Phe Leu Phe Pro
    210                 215                 220

Pro Lys Pro Lys Asp Thr Leu Met Ile Ser Arg Thr Pro Glu Val Thr
225                 230                 235                 240

Cys Val Val Val Asp Val Ser His Glu Asp Pro Glu Val Lys Phe Asn
            245                 250                 255

Trp Tyr Val Asp Gly Val Glu Val His Asn Ala Lys Thr Lys Pro Arg
            260                 265                 270

Glu Glu Gln Tyr Asn Ser Thr Tyr Arg Val Val Ser Val Leu Thr Val
            275                 280                 285

Leu His Gln Asp Trp Leu Asn Gly Lys Glu Tyr Lys Cys Lys Val Ser
```

-continued

```
              290                 295                 300

Asn Lys Ala Leu Pro Ala Pro Ile Glu Lys Thr Ile Ser Lys Ala Lys
305                 310                 315                 320

Gly Gln Pro Arg Glu Pro Gln Val Tyr Thr Leu Pro Pro Ser Arg Asp
                    325                 330                 335

Glu Leu Thr Lys Asn Gln Val Ser Leu Thr Cys Leu Val Lys Gly Phe
                    340                 345                 350

Tyr Pro Ser Asp Ile Ala Val Glu Trp Glu Ser Asn Gly Gln Pro Glu
                    355                 360                 365

Asn Asn Tyr Lys Thr Thr Pro Pro Val Leu Asp Ser Asp Gly Ser Phe
            370                 375                 380

Phe Leu Tyr Ser Lys Leu Thr Val Asp Lys Ser Arg Trp Gln Gln Gly
385                 390                 395                 400

Asn Val Phe Ser Cys Ser Val Met His Glu Ala Leu His Asn His Tyr
                    405                 410                 415

Thr Gln Lys Ser Leu Ser Leu Ser Pro Gly Lys
                420                 425

<210> SEQ ID NO 4
<211> LENGTH: 397
<212> TYPE: PRT
<213> ORGANISM: Artificial Sequence
<220> FEATURE:
<223> OTHER INFORMATION: Mature D6-Fc

<400> SEQUENCE: 4

Arg Ser Pro Val Thr Pro Glu Leu Pro Gly Pro Asp Pro Thr Pro Ser
1                   5                   10                  15

Leu Thr Gly Ser Cys Pro Gln Gly Trp Ala Ser Asp Thr Lys Leu Arg
                20                  25                  30

Tyr Cys Tyr Lys Val Phe Ser Ser Glu Arg Leu Gln Asp Lys Lys Ser
                35                  40                  45

Trp Val Gln Ala Gln Gly Ala Cys Gln Glu Leu Gly Ala Gln Leu Leu
            50                  55                  60

Ser Leu Ala Ser Tyr Glu Glu Glu His Phe Val Ala Asn Met Leu Asn
65                  70                  75                  80

Lys Ile Phe Gly Glu Ser Glu Pro Glu Ile His Glu Gln His Trp Phe
                    85                  90                  95

Trp Ile Gly Leu Asn Arg Arg Asp Pro Arg Gly Gly Gln Ser Trp Arg
                    100                 105                 110

Trp Ser Asp Gly Val Gly Phe Ser Tyr His Asn Phe Asp Arg Ser Arg
            115                 120                 125

His Asp Asp Asp Asp Ile Arg Gly Cys Ala Val Leu Asp Leu Ala Ser
            130                 135                 140

Leu Gln Trp Val Ala Met Gln Cys Asp Thr Gln Leu Asp Trp Ile Cys
145                 150                 155                 160

Lys Ile Pro Arg Ser Glu Pro Lys Ser Cys Asp Lys Thr His Thr Cys
                    165                 170                 175

Pro Pro Cys Pro Ala Pro Glu Leu Leu Gly Gly Pro Ser Val Phe Leu
                180                 185                 190

Phe Pro Pro Lys Pro Lys Asp Thr Leu Met Ile Ser Arg Thr Pro Glu
                195                 200                 205

Val Thr Cys Val Val Val Asp Val Ser His Glu Asp Pro Glu Val Lys
            210                 215                 220

Phe Asn Trp Tyr Val Asp Gly Val Glu Val His Asn Ala Lys Thr Lys
```

-continued

```
225             230             235             240

Pro Arg Glu Glu Gln Tyr Asn Ser Thr Tyr Arg Val Val Ser Val Leu
            245             250             255

Thr Val Leu His Gln Asp Trp Leu Asn Gly Lys Glu Tyr Lys Cys Lys
            260             265             270

Val Ser Asn Lys Ala Leu Pro Ala Pro Ile Glu Lys Thr Ile Ser Lys
            275             280             285

Ala Lys Gly Gln Pro Arg Glu Pro Gln Val Tyr Thr Leu Pro Pro Ser
    290             295             300

Arg Asp Glu Leu Thr Lys Asn Gln Val Ser Leu Thr Cys Leu Val Lys
305             310             315             320

Gly Phe Tyr Pro Ser Asp Ile Ala Val Glu Trp Glu Ser Asn Gly Gln
            325             330             335

Pro Glu Asn Asn Tyr Lys Thr Thr Pro Pro Val Leu Asp Ser Asp Gly
            340             345             350

Ser Phe Phe Leu Tyr Ser Lys Leu Thr Val Asp Lys Ser Arg Trp Gln
            355             360             365

Gln Gly Asn Val Phe Ser Cys Ser Val Met His Glu Ala Leu His Asn
    370             375             380

His Tyr Thr Gln Lys Ser Leu Ser Leu Ser Pro Gly Lys
385             390             395
```

```
<210> SEQ ID NO 5
<211> LENGTH: 30
<212> TYPE: PRT
<213> ORGANISM: Artificial Sequence
<220> FEATURE:
<223> OTHER INFORMATION: Signal Peptide

<400> SEQUENCE: 5

Met Gly Pro Gly Arg Pro Ala Pro Ala Pro Trp Pro Arg His Leu Leu
1               5               10              15

Arg Cys Val Leu Leu Leu Gly Cys Leu His Leu Gly Arg Pro
            20              25              30
```

```
<210> SEQ ID NO 6
<211> LENGTH: 232
<212> TYPE: PRT
<213> ORGANISM: Artificial Sequence
<220> FEATURE:
<223> OTHER INFORMATION: Fc

<400> SEQUENCE: 6

Glu Pro Lys Ser Cys Asp Lys Thr His Thr Cys Pro Pro Cys Pro Ala
1               5               10              15

Pro Glu Leu Leu Gly Gly Pro Ser Val Phe Leu Phe Pro Pro Lys Pro
            20              25              30

Lys Asp Thr Leu Met Ile Ser Arg Thr Pro Glu Val Thr Cys Val Val
            35              40              45

Val Asp Val Ser His Glu Asp Pro Glu Val Lys Phe Asn Trp Tyr Val
    50              55              60

Asp Gly Val Glu Val His Asn Ala Lys Thr Lys Pro Arg Glu Glu Gln
65              70              75              80

Tyr Asn Ser Thr Tyr Arg Val Val Ser Val Leu Thr Val Leu His Gln
            85              90              95

Asp Trp Leu Asn Gly Lys Glu Tyr Lys Cys Lys Val Ser Asn Lys Ala
            100             105             110
```

```
Leu Pro Ala Pro Ile Glu Lys Thr Ile Ser Lys Ala Lys Gly Gln Pro
        115             120             125

Arg Glu Pro Gln Val Tyr Thr Leu Pro Pro Ser Arg Asp Glu Leu Thr
    130             135             140

Lys Asn Gln Val Ser Leu Thr Cys Leu Val Lys Gly Phe Tyr Pro Ser
145             150             155             160

Asp Ile Ala Val Glu Trp Glu Ser Asn Gly Gln Pro Glu Asn Asn Tyr
            165             170             175

Lys Thr Thr Pro Pro Val Leu Asp Ser Asp Gly Ser Phe Phe Leu Tyr
            180             185             190

Ser Lys Leu Thr Val Asp Lys Ser Arg Trp Gln Gln Gly Asn Val Phe
        195             200             205

Ser Cys Ser Val Met His Glu Ala Leu His Asn His Tyr Thr Gln Lys
    210             215             220

Ser Leu Ser Leu Ser Pro Gly Lys
225             230

<210> SEQ ID NO 7
<211> LENGTH: 1384
<212> TYPE: PRT
<213> ORGANISM: Artificial Sequence
<220> FEATURE:
<223> OTHER INFORMATION: Mature Endo180 Ecto-domain (Uniprot Q9UBG0)

<400> SEQUENCE: 7

Gly Ala Pro Gly Asp Ala Ala Leu Pro Glu Pro Asn Val Phe Leu Ile
1               5               10              15

Phe Ser His Gly Leu Gln Gly Cys Leu Glu Ala Gln Gly Gly Gln Val
            20              25              30

Arg Val Thr Pro Ala Cys Asn Thr Ser Leu Pro Ala Gln Arg Trp Lys
        35              40              45

Trp Val Ser Arg Asn Arg Leu Phe Asn Leu Gly Thr Met Gln Cys Leu
    50              55              60

Gly Thr Gly Trp Pro Gly Thr Asn Thr Thr Ala Ser Leu Gly Met Tyr
65              70              75              80

Glu Cys Asp Arg Glu Ala Leu Asn Leu Arg Trp His Cys Arg Thr Leu
            85              90              95

Gly Asp Gln Leu Ser Leu Leu Leu Gly Ala Arg Thr Ser Asn Ile Ser
            100             105             110

Lys Pro Gly Thr Leu Glu Arg Gly Asp Gln Thr Arg Ser Gly Gln Trp
        115             120             125

Arg Ile Tyr Gly Ser Glu Glu Asp Leu Cys Ala Leu Pro Tyr His Glu
    130             135             140

Val Tyr Thr Ile Gln Gly Asn Ser His Gly Lys Pro Cys Thr Ile Pro
145             150             155             160

Phe Lys Tyr Asp Asn Gln Trp Phe His Gly Cys Thr Ser Thr Gly Arg
            165             170             175

Glu Asp Gly His Leu Trp Cys Ala Thr Thr Gln Asp Tyr Gly Lys Asp
            180             185             190

Glu Arg Trp Gly Phe Cys Pro Ile Lys Ser Asn Asp Cys Glu Thr Phe
        195             200             205

Trp Asp Lys Asp Gln Leu Thr Asp Ser Cys Tyr Gln Phe Asn Phe Gln
        210             215             220

Ser Thr Leu Ser Trp Arg Glu Ala Trp Ala Ser Cys Glu Gln Gln Gly
225             230             235             240
```

-continued

```
Ala Asp Leu Leu Ser Ile Thr Glu Ile His Glu Gln Thr Tyr Ile Asn
                245                 250                 255

Gly Leu Leu Thr Gly Tyr Ser Ser Thr Leu Trp Ile Gly Leu Asn Asp
            260                 265                 270

Leu Asp Thr Ser Gly Gly Trp Gln Trp Ser Asp Asn Ser Pro Leu Lys
        275                 280                 285

Tyr Leu Asn Trp Glu Ser Asp Gln Pro Asp Asn Pro Ser Glu Glu Asn
    290                 295                 300

Cys Gly Val Ile Arg Thr Glu Ser Ser Gly Gly Trp Gln Asn Arg Asp
305                 310                 315                 320

Cys Ser Ile Ala Leu Pro Tyr Val Cys Lys Lys Lys Pro Asn Ala Thr
                325                 330                 335

Ala Glu Pro Thr Pro Pro Asp Arg Trp Ala Asn Val Lys Val Glu Cys
            340                 345                 350

Glu Pro Ser Trp Gln Pro Phe Gln Gly His Cys Tyr Arg Leu Gln Ala
            355                 360                 365

Glu Lys Arg Ser Trp Gln Glu Ser Lys Lys Ala Cys Leu Arg Gly Gly
    370                 375                 380

Gly Asp Leu Val Ser Ile His Ser Met Ala Glu Leu Glu Phe Ile Thr
385                 390                 395                 400

Lys Gln Ile Lys Gln Glu Val Glu Glu Leu Trp Ile Gly Leu Asn Asp
            405                 410                 415

Leu Lys Leu Gln Met Asn Phe Glu Trp Ser Asp Gly Ser Leu Val Ser
            420                 425                 430

Phe Thr His Trp His Pro Phe Glu Pro Asn Asn Phe Arg Asp Ser Leu
        435                 440                 445

Glu Asp Cys Val Thr Ile Trp Gly Pro Glu Gly Arg Trp Asn Asp Ser
    450                 455                 460

Pro Cys Asn Gln Ser Leu Pro Ser Ile Cys Lys Lys Ala Gly Gln Leu
465                 470                 475                 480

Ser Gln Gly Ala Ala Glu Glu Asp His Gly Cys Arg Lys Gly Trp Thr
                485                 490                 495

Trp His Ser Pro Ser Cys Tyr Trp Leu Gly Glu Asp Gln Val Thr Tyr
            500                 505                 510

Ser Glu Ala Arg Arg Leu Cys Thr Asp His Gly Ser Gln Leu Val Thr
            515                 520                 525

Ile Thr Asn Arg Phe Glu Gln Ala Phe Val Ser Ser Leu Ile Tyr Asn
    530                 535                 540

Trp Glu Gly Glu Tyr Phe Trp Thr Ala Leu Gln Asp Leu Asn Ser Thr
545                 550                 555                 560

Gly Ser Phe Phe Trp Leu Ser Gly Asp Glu Val Met Tyr Thr His Trp
            565                 570                 575

Asn Arg Asp Gln Pro Gly Tyr Ser Arg Gly Gly Cys Val Ala Leu Ala
            580                 585                 590

Thr Gly Ser Ala Met Gly Leu Trp Glu Val Lys Asn Cys Thr Ser Phe
            595                 600                 605

Arg Ala Arg Tyr Ile Cys Arg Gln Ser Leu Gly Thr Pro Val Thr Pro
    610                 615                 620

Glu Leu Pro Gly Pro Asp Pro Thr Pro Ser Leu Thr Gly Ser Cys Pro
625                 630                 635                 640

Gln Gly Trp Ala Ser Asp Thr Lys Leu Arg Tyr Cys Tyr Lys Val Phe
            645                 650                 655

Ser Ser Glu Arg Leu Gln Asp Lys Lys Ser Trp Val Gln Ala Gln Gly
```

-continued

```
              660              665              670

Ala Cys Gln Glu Leu Gly Ala Gln Leu Leu Ser Leu Ala Ser Tyr Glu
         675              680              685

Glu Glu His Phe Val Ala Asn Met Leu Asn Lys Ile Phe Gly Glu Ser
    690              695              700

Glu Pro Glu Ile His Glu Gln His Trp Phe Trp Ile Gly Leu Asn Arg
705              710              715              720

Arg Asp Pro Arg Gly Gly Gln Ser Trp Arg Trp Ser Asp Gly Val Gly
              725              730              735

Phe Ser Tyr His Asn Phe Asp Arg Ser Arg His Asp Asp Asp Ile
              740              745              750

Arg Gly Cys Ala Val Leu Asp Leu Ala Ser Leu Gln Trp Val Ala Met
              755              760              765

Gln Cys Asp Thr Gln Leu Asp Trp Ile Cys Lys Ile Pro Arg Gly Thr
    770              775              780

Asp Val Arg Glu Pro Asp Asp Ser Pro Gln Gly Arg Arg Glu Trp Leu
785              790              795              800

Arg Phe Gln Glu Ala Glu Tyr Lys Phe Phe Glu His His Ser Thr Trp
              805              810              815

Ala Gln Ala Gln Arg Ile Cys Thr Trp Phe Gln Ala Glu Leu Thr Ser
              820              825              830

Val His Ser Gln Ala Glu Leu Asp Phe Leu Ser His Asn Leu Gln Lys
              835              840              845

Phe Ser Arg Ala Gln Glu Gln His Trp Trp Ile Gly Leu His Thr Ser
    850              855              860

Glu Ser Asp Gly Arg Phe Arg Trp Thr Asp Gly Ser Ile Ile Asn Phe
865              870              875              880

Ile Ser Trp Ala Pro Gly Lys Pro Arg Pro Val Gly Lys Asp Lys Lys
              885              890              895

Cys Val Tyr Met Thr Ala Ser Arg Glu Asp Trp Gly Asp Gln Arg Cys
              900              905              910

Leu Thr Ala Leu Pro Tyr Ile Cys Lys Arg Ser Asn Val Thr Lys Glu
              915              920              925

Thr Gln Pro Pro Asp Leu Pro Thr Thr Ala Leu Gly Gly Cys Pro Ser
    930              935              940

Asp Trp Ile Gln Phe Leu Asn Lys Cys Phe Gln Val Gln Gly Gln Glu
945              950              955              960

Pro Gln Ser Arg Val Lys Trp Ser Glu Ala Gln Phe Ser Cys Glu Gln
              965              970              975

Gln Glu Ala Gln Leu Val Thr Ile Thr Asn Pro Leu Glu Gln Ala Phe
              980              985              990

Ile Thr Ala Ser Leu Pro Asn Val Thr Phe Asp Leu Trp Ile Gly Leu
         995              1000             1005

His Ala Ser Gln Arg Asp Phe Gln Trp Val Glu Gln Glu Pro Leu
    1010             1015             1020

Met Tyr Ala Asn Trp Ala Pro Gly Glu Pro Ser Gly Pro Ser Pro
    1025             1030             1035

Ala Pro Ser Gly Asn Lys Pro Thr Ser Cys Ala Val Val Leu His
    1040             1045             1050

Ser Pro Ser Ala His Phe Thr Gly Arg Trp Asp Asp Arg Ser Cys
    1055             1060             1065

Thr Glu Glu Thr His Gly Phe Ile Cys Gln Lys Gly Thr Asp Pro
    1070             1075             1080
```

-continued

```
Ser Leu Ser Pro Ser Pro Ala  Ala Leu Pro Pro Ala  Pro Gly Thr
    1085              1090              1095

Glu Leu Ser Tyr Leu Asn Gly  Thr Phe Arg Leu Leu  Gln Lys Pro
    1100              1105              1110

Leu Arg Trp His Asp Ala Leu  Leu Leu Cys Glu Ser  Arg Asn Ala
    1115              1120              1125

Ser Leu Ala Tyr Val Pro Asp  Pro Tyr Thr Gln Ala  Phe Leu Thr
    1130              1135              1140

Gln Ala Ala Arg Gly Leu Arg  Thr Pro Leu Trp Ile  Gly Leu Ala
    1145              1150              1155

Gly Glu Glu Gly Ser Arg Arg  Tyr Ser Trp Val Ser  Glu Glu Pro
    1160              1165              1170

Leu Asn Tyr Val Gly Trp Gln  Asp Gly Glu Pro Gln  Gln Pro Gly
    1175              1180              1185

Gly Cys Thr Tyr Val Asp Val  Asp Gly Ala Trp Arg  Thr Thr Ser
    1190              1195              1200

Cys Asp Thr Lys Leu Gln Gly  Ala Val Cys Gly Val  Ser Ser Gly
    1205              1210              1215

Pro Pro Pro Pro Arg Arg Ile  Ser Tyr His Gly Ser  Cys Pro Gln
    1220              1225              1230

Gly Leu Ala Asp Ser Ala Trp  Ile Pro Phe Arg Glu  His Cys Tyr
    1235              1240              1245

Ser Phe His Met Glu Leu Leu  Leu Gly His Lys Glu  Ala Arg Gln
    1250              1255              1260

Arg Cys Gln Arg Ala Gly Gly  Ala Val Leu Ser Ile  Leu Asp Glu
    1265              1270              1275

Met Glu Asn Val Phe Val Trp  Glu His Leu Gln Ser  Tyr Glu Gly
    1280              1285              1290

Gln Ser Arg Gly Ala Trp Leu  Gly Met Asn Phe Asn  Pro Lys Gly
    1295              1300              1305

Gly Thr Leu Val Trp Gln Asp  Asn Thr Ala Val Asn  Tyr Ser Asn
    1310              1315              1320

Trp Gly Pro Pro Gly Leu Gly  Pro Ser Met Leu Ser  His Asn Ser
    1325              1330              1335

Cys Tyr Trp Ile Gln Ser Asn  Ser Gly Leu Trp Arg  Pro Gly Ala
    1340              1345              1350

Cys Thr Asn Ile Thr Met Gly  Val Val Cys Lys Leu  Pro Arg Ala
    1355              1360              1365

Glu Gln Ser Ser Phe Ser Pro  Ser Ala Leu Pro Glu  Asn Pro Ala
    1370              1375              1380

Ala
```

<210> SEQ ID NO 8
<211> LENGTH: 127
<212> TYPE: PRT
<213> ORGANISM: Artificial Sequence
<220> FEATURE:
<223> OTHER INFORMATION: D1 (Ricin B-type lectin domain)

<400> SEQUENCE: 8

```
Pro Asn Val Phe Leu Ile Phe Ser His Gly Leu Gln Gly Cys Leu Glu
1               5                   10                  15

Ala Gln Gly Gly Gln Val Arg Val Thr Pro Ala Cys Asn Thr Ser Leu
            20                  25                  30
```

```
Pro Ala Gln Arg Trp Lys Trp Val Ser Arg Asn Arg Leu Phe Asn Leu
        35              40              45

Gly Thr Met Gln Cys Leu Gly Thr Gly Trp Pro Gly Thr Asn Thr Thr
        50              55              60

Ala Ser Leu Gly Met Tyr Glu Cys Asp Arg Glu Ala Leu Asn Leu Arg
65                  70              75                  80

Trp His Cys Arg Thr Leu Gly Asp Gln Leu Ser Leu Leu Leu Gly Ala
                85              90                  95

Arg Thr Ser Asn Ile Ser Lys Pro Gly Thr Leu Glu Arg Gly Asp Gln
                100             105             110

Thr Arg Ser Gly Gln Trp Arg Ile Tyr Gly Ser Glu Glu Asp Leu
        115             120             125
```

```
<210> SEQ ID NO 9
<211> LENGTH: 49
<212> TYPE: PRT
<213> ORGANISM: Artificial Sequence
<220> FEATURE:
<223> OTHER INFORMATION: D2 (Fibronectin type-II domain)

<400> SEQUENCE: 9

Ser His Gly Lys Pro Cys Thr Ile Pro Phe Lys Tyr Asp Asn Gln Trp
1               5               10              15

Phe His Gly Cys Thr Ser Thr Gly Arg Glu Asp Gly His Leu Trp Cys
                20              25              30

Ala Thr Thr Gln Asp Tyr Gly Lys Asp Glu Arg Trp Gly Phe Cys Pro
        35              40              45

Ile
```

```
<210> SEQ ID NO 10
<211> LENGTH: 117
<212> TYPE: PRT
<213> ORGANISM: Artificial Sequence
<220> FEATURE:
<223> OTHER INFORMATION: D3 (C-type lectin 1)

<400> SEQUENCE: 10

Leu Thr Asp Ser Cys Tyr Gln Phe Asn Phe Gln Ser Thr Leu Ser Trp
1               5               10              15

Arg Glu Ala Trp Ala Ser Cys Glu Gln Gln Gly Ala Asp Leu Leu Ser
                20              25              30

Ile Thr Glu Ile His Glu Gln Thr Tyr Ile Asn Gly Leu Leu Thr Gly
        35              40              45

Tyr Ser Ser Thr Leu Trp Ile Gly Leu Asn Asp Leu Asp Thr Ser Gly
        50              55              60

Gly Trp Gln Trp Ser Asp Asn Ser Pro Leu Lys Tyr Leu Asn Trp Glu
65              70              75                  80

Ser Asp Gln Pro Asp Asn Pro Ser Glu Glu Asn Cys Gly Val Ile Arg
                85              90              95

Thr Glu Ser Ser Gly Gly Trp Gln Asn Arg Asp Cys Ser Ile Ala Leu
                100             105             110

Pro Tyr Val Cys Lys
        115
```

```
<210> SEQ ID NO 11
<211> LENGTH: 117
<212> TYPE: PRT
<213> ORGANISM: Artificial Sequence
<220> FEATURE:
```

<223> OTHER INFORMATION: D4 (C-type lectin 2)

<400> SEQUENCE: 11

```
Phe Gln Gly His Cys Tyr Arg Leu Gln Ala Glu Lys Arg Ser Trp Gln
1               5                   10                  15

Glu Ser Lys Lys Ala Cys Leu Arg Gly Gly Asp Leu Val Ser Ile
            20                  25                  30

His Ser Met Ala Glu Leu Glu Phe Ile Thr Lys Gln Ile Lys Gln Glu
        35                  40                  45

Val Glu Glu Leu Trp Ile Gly Leu Asn Asp Leu Lys Leu Gln Met Asn
    50                  55                  60

Phe Glu Trp Ser Asp Gly Ser Leu Val Ser Phe Thr His Trp His Pro
65                  70                  75                  80

Phe Glu Pro Asn Asn Phe Arg Asp Ser Leu Glu Asp Cys Val Thr Ile
                85                  90                  95

Trp Gly Pro Glu Gly Arg Trp Asn Asp Ser Pro Cys Asn Gln Ser Leu
            100                 105                 110

Pro Ser Ile Cys Lys
        115
```

<210> SEQ ID NO 12
<211> LENGTH: 117
<212> TYPE: PRT
<213> ORGANISM: Artificial Sequence
<220> FEATURE:
<223> OTHER INFORMATION: D5 (C-type lectin 3)

<400> SEQUENCE: 12

```
His Ser Pro Ser Cys Tyr Trp Leu Gly Glu Asp Gln Val Thr Tyr Ser
1               5                   10                  15

Glu Ala Arg Arg Leu Cys Thr Asp His Gly Ser Gln Leu Val Thr Ile
            20                  25                  30

Thr Asn Arg Phe Glu Gln Ala Phe Val Ser Ser Leu Ile Tyr Asn Trp
        35                  40                  45

Glu Gly Glu Tyr Phe Trp Thr Ala Leu Gln Asp Leu Asn Ser Thr Gly
    50                  55                  60

Ser Phe Phe Trp Leu Ser Gly Asp Glu Val Met Tyr Thr His Trp Asn
65                  70                  75                  80

Arg Asp Gln Pro Gly Tyr Ser Arg Gly Gly Cys Val Ala Leu Ala Thr
                85                  90                  95

Gly Ser Ala Met Gly Leu Trp Glu Val Lys Asn Cys Thr Ser Phe Arg
            100                 105                 110

Ala Arg Tyr Ile Cys
        115
```

<210> SEQ ID NO 13
<211> LENGTH: 132
<212> TYPE: PRT
<213> ORGANISM: Artificial Sequence
<220> FEATURE:
<223> OTHER INFORMATION: D6 (C-type lectin 4)

<400> SEQUENCE: 13

```
Lys Leu Arg Tyr Cys Tyr Lys Val Phe Ser Ser Glu Arg Leu Gln Asp
1               5                   10                  15

Lys Lys Ser Trp Val Gln Ala Gln Gly Ala Cys Gln Glu Leu Gly Ala
            20                  25                  30

Gln Leu Leu Ser Leu Ala Ser Tyr Glu Glu Glu His Phe Val Ala Asn
```

-continued

```
             35                  40                  45
Met Leu Asn Lys Ile Phe Gly Glu Ser Glu Pro Glu Ile His Glu Gln
    50                  55                  60
His Trp Phe Trp Ile Gly Leu Asn Arg Arg Asp Pro Arg Gly Gly Gln
65                  70                  75                  80
Ser Trp Arg Trp Ser Asp Gly Val Gly Phe Ser Tyr His Asn Phe Asp
                85                  90                  95
Arg Ser Arg His Asp Asp Asp Asp Ile Arg Gly Cys Ala Val Leu Asp
                100                 105                 110
Leu Ala Ser Leu Gln Trp Val Ala Met Gln Cys Asp Thr Gln Leu Asp
        115                 120                 125
Trp Ile Cys Lys
    130

<210> SEQ ID NO 14
<211> LENGTH: 120
<212> TYPE: PRT
<213> ORGANISM: Artificial Sequence
<220> FEATURE:
<223> OTHER INFORMATION: D7 (C-type lectin 5)

<400> SEQUENCE: 14

Phe Gln Glu Ala Glu Tyr Lys Phe Phe Glu His His Ser Thr Trp Ala
1               5                   10                  15
Gln Ala Gln Arg Ile Cys Thr Trp Phe Gln Ala Glu Leu Thr Ser Val
                20                  25                  30
His Ser Gln Ala Glu Leu Asp Phe Leu Ser His Asn Leu Gln Lys Phe
        35                  40                  45
Ser Arg Ala Gln Glu Gln His Trp Trp Ile Gly Leu His Thr Ser Glu
    50                  55                  60
Ser Asp Gly Arg Phe Arg Trp Thr Asp Gly Ser Ile Ile Asn Phe Ile
65                  70                  75                  80
Ser Trp Ala Pro Gly Lys Pro Arg Pro Val Gly Lys Asp Lys Lys Cys
                85                  90                  95
Val Tyr Met Thr Ala Ser Arg Glu Asp Trp Gly Asp Gln Arg Cys Leu
                100                 105                 110
Thr Ala Leu Pro Tyr Ile Cys Lys
        115                 120

<210> SEQ ID NO 15
<211> LENGTH: 129
<212> TYPE: PRT
<213> ORGANISM: Artificial Sequence
<220> FEATURE:
<223> OTHER INFORMATION: D8 (C-type lectin 6)

<400> SEQUENCE: 15

Phe Leu Asn Lys Cys Phe Gln Val Gln Gly Gln Glu Pro Gln Ser Arg
1               5                   10                  15
Val Lys Trp Ser Glu Ala Gln Phe Ser Cys Glu Gln Gln Glu Ala Gln
                20                  25                  30
Leu Val Thr Ile Thr Asn Pro Leu Glu Gln Ala Phe Ile Thr Ala Ser
        35                  40                  45
Leu Pro Asn Val Thr Phe Asp Leu Trp Ile Gly Leu His Ala Ser Gln
    50                  55                  60
Arg Asp Phe Gln Trp Val Glu Gln Glu Pro Leu Met Tyr Ala Asn Trp
65                  70                  75                  80
```

```
Ala Pro Gly Glu Pro Ser Gly Pro Ser Pro Ala Pro Ser Gly Asn Lys
                85              90              95

Pro Thr Ser Cys Ala Val Val Leu His Ser Pro Ser Ala His Phe Thr
            100             105             110

Gly Arg Trp Asp Asp Arg Ser Cys Thr Glu Glu Thr His Gly Phe Ile
        115             120             125

Cys

<210> SEQ ID NO 16
<211> LENGTH: 112
<212> TYPE: PRT
<213> ORGANISM: Artificial Sequence
<220> FEATURE:
<223> OTHER INFORMATION: D9 (C-type lectin 7)

<400> SEQUENCE: 16

Tyr Leu Asn Gly Thr Phe Arg Leu Leu Gln Lys Pro Leu Arg Trp His
1               5               10              15

Asp Ala Leu Leu Leu Cys Glu Ser Arg Asn Ala Ser Leu Ala Tyr Val
            20              25              30

Pro Asp Pro Tyr Thr Gln Ala Phe Leu Thr Gln Ala Ala Arg Gly Leu
        35              40              45

Arg Thr Pro Leu Trp Ile Gly Leu Ala Gly Glu Glu Gly Ser Arg Arg
    50              55              60

Tyr Ser Trp Val Ser Glu Glu Pro Leu Asn Tyr Val Gly Trp Gln Asp
65              70              75              80

Gly Glu Pro Gln Gln Pro Gly Gly Cys Thr Tyr Val Asp Val Asp Gly
            85              90              95

Ala Trp Arg Thr Thr Ser Cys Asp Thr Lys Leu Gln Gly Ala Val Cys
            100             105             110

<210> SEQ ID NO 17
<211> LENGTH: 121
<212> TYPE: PRT
<213> ORGANISM: Artificial Sequence
<220> FEATURE:
<223> OTHER INFORMATION: D10 (C-type lectin 8)

<400> SEQUENCE: 17

Phe Arg Glu His Cys Tyr Ser Phe His Met Glu Leu Leu Leu Gly His
1               5               10              15

Lys Glu Ala Arg Gln Arg Cys Gln Arg Ala Gly Gly Ala Val Leu Ser
            20              25              30

Ile Leu Asp Glu Met Glu Asn Val Phe Val Trp Glu His Leu Gln Ser
        35              40              45

Tyr Glu Gly Gln Ser Arg Gly Ala Trp Leu Gly Met Asn Phe Asn Pro
    50              55              60

Lys Gly Gly Thr Leu Val Trp Gln Asp Asn Thr Ala Val Asn Tyr Ser
65              70              75              80

Asn Trp Gly Pro Pro Gly Leu Gly Pro Ser Met Leu Ser His Asn Ser
            85              90              95

Cys Tyr Trp Ile Gln Ser Asn Ser Gly Leu Trp Arg Pro Gly Ala Cys
            100             105             110

Thr Asn Ile Thr Met Gly Val Val Cys
        115             120

<210> SEQ ID NO 18
<211> LENGTH: 309
```

<212> TYPE: PRT
<213> ORGANISM: Artificial Sequence
<220> FEATURE:
<223> OTHER INFORMATION: Trimerization peptide (Type I) with glycine-X-Y
      repeats and D-N mutation at BMP-1 site, KS version

<400> SEQUENCE: 18

```
Asn Gly Leu Pro Gly Pro Ile Gly Pro Pro Gly Pro Arg Gly Arg Thr
1               5                   10                  15

Gly Asp Ala Gly Pro Val Gly Pro Pro Gly Pro Pro Gly Pro Pro Gly
            20                  25                  30

Pro Pro Gly Pro Pro Ser Ala Gly Phe Asp Phe Ser Phe Leu Pro Gln
        35                  40                  45

Pro Pro Gln Glu Lys Ala His Asp Gly Gly Arg Tyr Tyr Arg Ala Asn
    50                  55                  60

Asp Ala Asn Val Val Arg Asp Arg Asp Leu Glu Val Asp Thr Thr Leu
65                  70                  75                  80

Lys Ser Leu Ser Gln Gln Ile Glu Asn Ile Arg Ser Pro Glu Gly Ser
                85                  90                  95

Arg Lys Asn Pro Ala Arg Thr Cys Arg Asp Leu Lys Met Cys His Ser
            100                 105                 110

Asp Trp Lys Ser Gly Glu Tyr Trp Ile Asp Pro Asn Gln Gly Cys Asn
        115                 120                 125

Leu Asp Ala Ile Lys Val Phe Cys Asn Met Glu Thr Gly Glu Thr Cys
    130                 135                 140

Val Tyr Pro Thr Gln Pro Ser Val Ala Gln Lys Asn Trp Tyr Ile Ser
145                 150                 155                 160

Lys Asn Pro Lys Asp Lys Arg His Val Trp Phe Gly Glu Ser Met Thr
            165                 170                 175

Asp Gly Phe Gln Phe Glu Tyr Gly Gly Gln Gly Ser Asp Pro Ala Asp
        180                 185                 190

Val Ala Ile Gln Leu Thr Phe Leu Arg Leu Met Ser Thr Glu Ala Ser
        195                 200                 205

Gln Asn Ile Thr Tyr His Cys Lys Asn Ser Val Ala Tyr Met Asp Gln
    210                 215                 220

Gln Thr Gly Asn Leu Lys Lys Ala Leu Leu Leu Lys Gly Ser Asn Glu
225                 230                 235                 240

Ile Glu Ile Arg Ala Glu Gly Asn Ser Arg Phe Thr Tyr Ser Val Thr
            245                 250                 255

Val Asp Gly Cys Thr Ser His Thr Gly Ala Trp Gly Lys Thr Val Ile
            260                 265                 270

Glu Tyr Lys Thr Thr Lys Ser Ser Arg Leu Pro Ile Ile Asp Val Ala
        275                 280                 285

Pro Leu Asp Val Gly Ala Pro Asp Gln Glu Phe Gly Phe Asp Val Gly
    290                 295                 300

Pro Val Cys Phe Leu
305
```

<210> SEQ ID NO 19
<211> LENGTH: 309
<212> TYPE: PRT
<213> ORGANISM: Artificial Sequence
<220> FEATURE:
<223> OTHER INFORMATION: Trimerization peptide (Type I) with glycine-X-Y
      repeats and A-N mutation at BMP-1 site, KS version

<400> SEQUENCE: 19

```
Asn Gly Leu Pro Gly Pro Ile Gly Pro Pro Gly Pro Arg Gly Arg Thr
1               5                   10                  15

Gly Asp Ala Gly Pro Val Gly Pro Pro Gly Pro Gly Pro Pro Gly
            20                  25                  30

Pro Pro Gly Pro Pro Ser Ala Gly Phe Asp Phe Ser Phe Leu Pro Gln
            35                  40                  45

Pro Pro Gln Glu Lys Ala His Asp Gly Gly Arg Tyr Tyr Arg Asn Asp
    50                  55                  60

Asp Ala Asn Val Val Arg Asp Arg Asp Leu Glu Val Asp Thr Thr Leu
65                  70                  75                  80

Lys Ser Leu Ser Gln Gln Ile Glu Asn Ile Arg Ser Pro Glu Gly Ser
                85                  90                  95

Arg Lys Asn Pro Ala Arg Thr Cys Arg Asp Leu Lys Met Cys His Ser
            100                 105                 110

Asp Trp Lys Ser Gly Glu Tyr Trp Ile Asp Pro Asn Gln Gly Cys Asn
            115                 120                 125

Leu Asp Ala Ile Lys Val Phe Cys Asn Met Glu Thr Gly Glu Thr Cys
    130                 135                 140

Val Tyr Pro Thr Gln Pro Ser Val Ala Gln Lys Asn Trp Tyr Ile Ser
145                 150                 155                 160

Lys Asn Pro Lys Asp Lys Arg His Val Trp Phe Gly Glu Ser Met Thr
            165                 170                 175

Asp Gly Phe Gln Phe Glu Tyr Gly Gly Gln Gly Ser Asp Pro Ala Asp
            180                 185                 190

Val Ala Ile Gln Leu Thr Phe Leu Arg Leu Met Ser Thr Glu Ala Ser
            195                 200                 205

Gln Asn Ile Thr Tyr His Cys Lys Asn Ser Val Ala Tyr Met Asp Gln
    210                 215                 220

Gln Thr Gly Asn Leu Lys Lys Ala Leu Leu Leu Lys Gly Ser Asn Glu
225                 230                 235                 240

Ile Glu Ile Arg Ala Glu Gly Asn Ser Arg Phe Thr Tyr Ser Val Thr
            245                 250                 255

Val Asp Gly Cys Thr Ser His Thr Gly Ala Trp Gly Lys Thr Val Ile
            260                 265                 270

Glu Tyr Lys Thr Thr Lys Ser Ser Arg Leu Pro Ile Ile Asp Val Ala
            275                 280                 285

Pro Leu Asp Val Gly Ala Pro Asp Gln Glu Phe Gly Phe Asp Val Gly
    290                 295                 300

Pro Val Cys Phe Leu
305
```

```
<210> SEQ ID NO 20
<211> LENGTH: 311
<212> TYPE: PRT
<213> ORGANISM: Artificial Sequence
<220> FEATURE:
<223> OTHER INFORMATION: Trimerization peptide (Type I) with glycine-X-Y
      repeats and D-N mutation at BMP-1 site, KS version

<400> SEQUENCE: 20
```

```
Arg Ser Asn Gly Leu Pro Gly Pro Ile Gly Pro Pro Gly Pro Arg Gly
1               5                   10                  15

Arg Thr Gly Asp Ala Gly Pro Val Gly Pro Pro Gly Pro Pro Gly Pro
            20                  25                  30

Pro Gly Pro Pro Gly Pro Pro Ser Ala Gly Phe Asp Phe Ser Phe Leu
            35                  40                  45
```

-continued

```
Pro Gln Pro Pro Gln Glu Lys Ala His Asp Gly Gly Arg Tyr Tyr Arg
    50              55              60

Ala Asn Asp Ala Asn Val Val Arg Asp Arg Asp Leu Glu Val Asp Thr
65              70              75              80

Thr Leu Lys Ser Leu Ser Gln Gln Ile Glu Asn Ile Arg Ser Pro Glu
            85              90              95

Gly Ser Arg Lys Asn Pro Ala Arg Thr Cys Arg Asp Leu Lys Met Cys
            100             105             110

His Ser Asp Trp Lys Ser Gly Glu Tyr Trp Ile Asp Pro Asn Gln Gly
        115             120             125

Cys Asn Leu Asp Ala Ile Lys Val Phe Cys Asn Met Glu Thr Gly Glu
    130             135             140

Thr Cys Val Tyr Pro Thr Gln Pro Ser Val Ala Gln Lys Asn Trp Tyr
145             150             155             160

Ile Ser Lys Asn Pro Lys Asp Lys Arg His Val Trp Phe Gly Glu Ser
            165             170             175

Met Thr Asp Gly Phe Gln Phe Glu Tyr Gly Gly Gln Gly Ser Asp Pro
            180             185             190

Ala Asp Val Ala Ile Gln Leu Thr Phe Leu Arg Leu Met Ser Thr Glu
            195             200             205

Ala Ser Gln Asn Ile Thr Tyr His Cys Lys Asn Ser Val Ala Tyr Met
    210             215             220

Asp Gln Gln Thr Gly Asn Leu Lys Lys Ala Leu Leu Leu Lys Gly Ser
225             230             235             240

Asn Glu Ile Glu Ile Arg Ala Glu Gly Asn Ser Arg Phe Thr Tyr Ser
            245             250             255

Val Thr Val Asp Gly Cys Thr Ser His Thr Gly Ala Trp Gly Lys Thr
            260             265             270

Val Ile Glu Tyr Lys Thr Thr Lys Ser Ser Arg Leu Pro Ile Ile Asp
            275             280             285

Val Ala Pro Leu Asp Val Gly Ala Pro Asp Gln Glu Phe Gly Phe Asp
    290             295             300

Val Gly Pro Val Cys Phe Leu
305             310
```

```
<210> SEQ ID NO 21
<211> LENGTH: 311
<212> TYPE: PRT
<213> ORGANISM: Artificial Sequence
<220> FEATURE:
<223> OTHER INFORMATION: Trimerization peptide (Type I) with glycine-X-Y
      repeats and D-N mutation at BMP-1 site, KS version

<400> SEQUENCE: 21

Gly Ser Asn Gly Leu Pro Gly Pro Ile Gly Pro Pro Gly Pro Arg Gly
1               5               10              15

Arg Thr Gly Asp Ala Gly Pro Val Gly Pro Pro Gly Pro Pro Gly Pro
            20              25              30

Pro Gly Pro Pro Gly Pro Pro Ser Ala Gly Phe Asp Phe Ser Phe Leu
        35              40              45

Pro Gln Pro Pro Gln Glu Lys Ala His Asp Gly Gly Arg Tyr Tyr Arg
    50              55              60

Ala Asn Asp Ala Asn Val Val Arg Asp Arg Asp Leu Glu Val Asp Thr
65              70              75              80

Thr Leu Lys Ser Leu Ser Gln Gln Ile Glu Asn Ile Arg Ser Pro Glu
```

```
                85                    90                    95

Gly Ser Arg Lys Asn Pro Ala Arg Thr Cys Arg Asp Leu Lys Met Cys
            100                   105                   110

His Ser Asp Trp Lys Ser Gly Glu Tyr Trp Ile Asp Pro Asn Gln Gly
            115                   120                   125

Cys Asn Leu Asp Ala Ile Lys Val Phe Cys Asn Met Glu Thr Gly Glu
        130                   135                   140

Thr Cys Val Tyr Pro Thr Gln Pro Ser Val Ala Gln Lys Asn Trp Tyr
145                   150                   155                   160

Ile Ser Lys Asn Pro Lys Asp Lys Arg His Val Trp Phe Gly Glu Ser
                165                   170                   175

Met Thr Asp Gly Phe Gln Phe Glu Tyr Gly Gly Gln Gly Ser Asp Pro
                180                   185                   190

Ala Asp Val Ala Ile Gln Leu Thr Phe Leu Arg Leu Met Ser Thr Glu
                195                   200                   205

Ala Ser Gln Asn Ile Thr Tyr His Cys Lys Asn Ser Val Ala Tyr Met
        210                   215                   220

Asp Gln Gln Thr Gly Asn Leu Lys Lys Ala Leu Leu Leu Lys Gly Ser
225                   230                   235                   240

Asn Glu Ile Glu Ile Arg Ala Glu Gly Asn Ser Arg Phe Thr Tyr Ser
                245                   250                   255

Val Thr Val Asp Gly Cys Thr Ser His Thr Gly Ala Trp Gly Lys Thr
                260                   265                   270

Val Ile Glu Tyr Lys Thr Thr Lys Ser Ser Arg Leu Pro Ile Ile Asp
                275                   280                   285

Val Ala Pro Leu Asp Val Gly Ala Pro Asp Gln Glu Phe Gly Phe Asp
            290                   295                   300

Val Gly Pro Val Cys Phe Leu
305                   310
```

<210> SEQ ID NO 22
<211> LENGTH: 309
<212> TYPE: PRT
<213> ORGANISM: Artificial Sequence
<220> FEATURE:
<223> OTHER INFORMATION: Trimerization peptide (Type I) with glycine-X-Y
      repeats, no BMP-1 site mutation, KS version

<400> SEQUENCE: 22

```
Asn Gly Leu Pro Gly Pro Ile Gly Pro Pro Gly Pro Arg Gly Arg Thr
1               5                   10                  15

Gly Asp Ala Gly Pro Val Gly Pro Pro Gly Pro Pro Gly Pro Pro Gly
            20                  25                  30

Pro Pro Gly Pro Pro Ser Ala Gly Phe Asp Phe Ser Phe Leu Pro Gln
        35                  40                  45

Pro Pro Gln Glu Lys Ala His Asp Gly Gly Arg Tyr Tyr Arg Ala Asp
    50                  55                  60

Asp Ala Asn Val Val Arg Asp Arg Asp Leu Glu Val Asp Thr Thr Leu
65                  70                  75                  80

Lys Ser Leu Ser Gln Gln Ile Glu Asn Ile Arg Ser Pro Glu Gly Ser
                85                  90                  95

Arg Lys Asn Pro Ala Arg Thr Cys Arg Asp Leu Lys Met Cys His Ser
            100                 105                 110

Asp Trp Lys Ser Gly Glu Tyr Trp Ile Asp Pro Asn Gln Gly Cys Asn
            115                 120                 125
```

-continued

```
Leu Asp Ala Ile Lys Val Phe Cys Asn Met Glu Thr Gly Glu Thr Cys
    130             135             140

Val Tyr Pro Thr Gln Pro Ser Val Ala Gln Lys Asn Trp Tyr Ile Ser
145             150             155             160

Lys Asn Pro Lys Asp Lys Arg His Val Trp Phe Gly Glu Ser Met Thr
            165             170             175

Asp Gly Phe Gln Phe Glu Tyr Gly Gly Gln Gly Ser Asp Pro Ala Asp
            180             185             190

Val Ala Ile Gln Leu Thr Phe Leu Arg Leu Met Ser Thr Glu Ala Ser
            195             200             205

Gln Asn Ile Thr Tyr His Cys Lys Asn Ser Val Ala Tyr Met Asp Gln
    210             215             220

Gln Thr Gly Asn Leu Lys Lys Ala Leu Leu Leu Lys Gly Ser Asn Glu
225             230             235             240

Ile Glu Ile Arg Ala Glu Gly Asn Ser Arg Phe Thr Tyr Ser Val Thr
            245             250             255

Val Asp Gly Cys Thr Ser His Thr Gly Ala Trp Gly Lys Thr Val Ile
            260             265             270

Glu Tyr Lys Thr Thr Lys Ser Ser Arg Leu Pro Ile Ile Asp Val Ala
    275             280             285

Pro Leu Asp Val Gly Ala Pro Asp Gln Glu Phe Gly Phe Asp Val Gly
    290             295             300

Pro Val Cys Phe Leu
305
```

```
<210> SEQ ID NO 23
<211> LENGTH: 310
<212> TYPE: PRT
<213> ORGANISM: Artificial Sequence
<220> FEATURE:
<223> OTHER INFORMATION: Trimerization peptide (Type I) with glycine-X-Y
      repeats, no BMP-1 site mutation, KS version

<400> SEQUENCE: 23

Ser Asn Gly Leu Pro Gly Pro Ile Gly Pro Pro Gly Pro Arg Gly Arg
1               5               10              15

Thr Gly Asp Ala Gly Pro Val Gly Pro Pro Gly Pro Pro Gly Pro Pro
            20              25              30

Gly Pro Pro Gly Pro Pro Ser Ala Gly Phe Asp Phe Ser Phe Leu Pro
            35              40              45

Gln Pro Pro Gln Glu Lys Ala His Asp Gly Gly Arg Tyr Tyr Arg Ala
    50              55              60

Asp Asp Ala Asn Val Val Arg Asp Arg Asp Leu Glu Val Asp Thr Thr
65              70              75              80

Leu Lys Ser Leu Ser Gln Gln Ile Glu Asn Ile Arg Ser Pro Glu Gly
            85              90              95

Ser Arg Lys Asn Pro Ala Arg Thr Cys Arg Asp Leu Lys Met Cys His
            100             105             110

Ser Asp Trp Lys Ser Gly Glu Tyr Trp Ile Asp Pro Asn Gln Gly Cys
            115             120             125

Asn Leu Asp Ala Ile Lys Val Phe Cys Asn Met Glu Thr Gly Glu Thr
    130             135             140

Cys Val Tyr Pro Thr Gln Pro Ser Val Ala Gln Lys Asn Trp Tyr Ile
145             150             155             160

Ser Lys Asn Pro Lys Asp Lys Arg His Val Trp Phe Gly Glu Ser Met
            165             170             175
```

-continued

```
Thr Asp Gly Phe Gln Phe Glu Tyr Gly Gly Gln Gly Ser Asp Pro Ala
            180                 185                 190

Asp Val Ala Ile Gln Leu Thr Phe Leu Arg Leu Met Ser Thr Glu Ala
            195                 200                 205

Ser Gln Asn Ile Thr Tyr His Cys Lys Asn Ser Val Ala Tyr Met Asp
            210                 215                 220

Gln Gln Thr Gly Asn Leu Lys Lys Ala Leu Leu Leu Lys Gly Ser Asn
225                 230                 235                 240

Glu Ile Glu Ile Arg Ala Glu Gly Asn Ser Arg Phe Thr Tyr Ser Val
                245                 250                 255

Thr Val Asp Gly Cys Thr Ser His Thr Gly Ala Trp Gly Lys Thr Val
            260                 265                 270

Ile Glu Tyr Lys Thr Thr Lys Ser Ser Arg Leu Pro Ile Ile Asp Val
            275                 280                 285

Ala Pro Leu Asp Val Gly Ala Pro Asp Gln Glu Phe Gly Phe Asp Val
            290                 295                 300

Gly Pro Val Cys Phe Leu
305                 310

<210> SEQ ID NO 24
<211> LENGTH: 309
<212> TYPE: PRT
<213> ORGANISM: Artificial Sequence
<220> FEATURE:
<223> OTHER INFORMATION: Trimerization peptide (Type I) with glycine-X-Y
      repeats, no BMP-1 site mutation, QT version

<400> SEQUENCE: 24

Asn Gly Leu Pro Gly Pro Ile Gly Pro Pro Gly Pro Arg Gly Arg Thr
1               5                   10                  15

Gly Asp Ala Gly Pro Val Gly Pro Pro Gly Pro Pro Gly Pro Pro Gly
            20                  25                  30

Pro Pro Gly Pro Pro Ser Ala Gly Phe Asp Phe Ser Phe Leu Pro Gln
            35                  40                  45

Pro Pro Gln Glu Lys Ala His Asp Gly Gly Arg Tyr Tyr Arg Ala Asp
            50                  55                  60

Asp Ala Asn Val Val Arg Asp Arg Asp Leu Glu Val Asp Thr Thr Leu
65                  70                  75                  80

Lys Ser Leu Ser Gln Gln Ile Glu Asn Ile Arg Ser Pro Glu Gly Ser
                85                  90                  95

Arg Lys Asn Pro Ala Arg Thr Cys Arg Asp Leu Lys Met Cys His Ser
            100                 105                 110

Asp Trp Lys Ser Gly Glu Tyr Trp Ile Asp Pro Asn Gln Gly Cys Asn
            115                 120                 125

Leu Asp Ala Ile Lys Val Phe Cys Asn Met Glu Thr Gly Glu Thr Cys
            130                 135                 140

Val Tyr Pro Thr Gln Pro Ser Val Ala Gln Lys Asn Trp Tyr Ile Ser
145                 150                 155                 160

Lys Asn Pro Lys Asp Lys Arg His Val Trp Phe Gly Glu Ser Met Thr
            165                 170                 175

Asp Gly Phe Gln Phe Glu Tyr Gly Gly Gln Gly Ser Asp Pro Ala Asp
            180                 185                 190

Val Ala Ile Gln Leu Thr Phe Leu Arg Leu Met Ser Thr Glu Ala Ser
            195                 200                 205

Gln Asn Ile Thr Tyr His Cys Lys Asn Ser Val Ala Tyr Met Asp Gln
```

-continued

```
        210              215              220
Gln Thr Gly Asn Leu Lys Lys Ala Leu Leu Leu Gln Gly Ser Asn Glu
225                 230                 235                 240

Ile Glu Ile Arg Ala Glu Gly Asn Ser Arg Phe Thr Tyr Ser Val Thr
                245                 250                 255

Val Asp Gly Cys Thr Ser His Thr Gly Ala Trp Gly Lys Thr Val Ile
                260                 265                 270

Glu Tyr Lys Thr Thr Lys Thr Ser Arg Leu Pro Ile Ile Asp Val Ala
            275                 280                 285

Pro Leu Asp Val Gly Ala Pro Asp Gln Glu Phe Gly Phe Asp Val Gly
        290                 295                 300

Pro Val Cys Phe Leu
305
```

<210> SEQ ID NO 25
<211> LENGTH: 310
<212> TYPE: PRT
<213> ORGANISM: Artificial Sequence
<220> FEATURE:
<223> OTHER INFORMATION: Trimerization peptide (Type I) with glycine-X-Y
      repeats, no BMP-1 site mutation, QT version

<400> SEQUENCE: 25

```
Ser Asn Gly Leu Pro Gly Pro Ile Gly Pro Pro Gly Pro Arg Gly Arg
1               5                   10                  15

Thr Gly Asp Ala Gly Pro Val Gly Pro Pro Gly Pro Pro Gly Pro Pro
                20                  25                  30

Gly Pro Pro Gly Pro Pro Ser Ala Gly Phe Asp Phe Ser Phe Leu Pro
            35                  40                  45

Gln Pro Pro Gln Glu Lys Ala His Asp Gly Gly Arg Tyr Tyr Arg Ala
        50                  55                  60

Asp Asp Ala Asn Val Val Arg Asp Arg Asp Leu Glu Val Asp Thr Thr
65                  70                  75                  80

Leu Lys Ser Leu Ser Gln Gln Ile Glu Asn Ile Arg Ser Pro Glu Gly
                85                  90                  95

Ser Arg Lys Asn Pro Ala Arg Thr Cys Arg Asp Leu Lys Met Cys His
            100                 105                 110

Ser Asp Trp Lys Ser Gly Glu Tyr Trp Ile Asp Pro Asn Gln Gly Cys
            115                 120                 125

Asn Leu Asp Ala Ile Lys Val Phe Cys Asn Met Glu Thr Gly Glu Thr
        130                 135                 140

Cys Val Tyr Pro Thr Gln Pro Ser Val Ala Gln Lys Asn Trp Tyr Ile
145                 150                 155                 160

Ser Lys Asn Pro Lys Asp Lys Arg His Val Trp Phe Gly Glu Ser Met
            165                 170                 175

Thr Asp Gly Phe Gln Phe Glu Tyr Gly Gly Gln Gly Ser Asp Pro Ala
            180                 185                 190

Asp Val Ala Ile Gln Leu Thr Phe Leu Arg Leu Met Ser Thr Glu Ala
            195                 200                 205

Ser Gln Asn Ile Thr Tyr His Cys Lys Asn Ser Val Ala Tyr Met Asp
        210                 215                 220

Gln Gln Thr Gly Asn Leu Lys Lys Ala Leu Leu Leu Gln Gly Ser Asn
225                 230                 235                 240

Glu Ile Glu Ile Arg Ala Glu Gly Asn Ser Arg Phe Thr Tyr Ser Val
                245                 250                 255
```

```
Thr Val Asp Gly Cys Thr Ser His Thr Gly Ala Trp Gly Lys Thr Val
            260                 265                 270

Ile Glu Tyr Lys Thr Thr Lys Thr Ser Arg Leu Pro Ile Ile Asp Val
            275                 280                 285

Ala Pro Leu Asp Val Gly Ala Pro Asp Gln Glu Phe Gly Phe Asp Val
    290                 295                 300

Gly Pro Val Cys Phe Leu
305                 310

<210> SEQ ID NO 26
<211> LENGTH: 244
<212> TYPE: PRT
<213> ORGANISM: Artificial Sequence
<220> FEATURE:
<223> OTHER INFORMATION: Trimerization peptide (Type I), KS version

<400> SEQUENCE: 26

Ala Asn Val Val Arg Asp Arg Asp Leu Glu Val Asp Thr Thr Leu Lys
1               5                   10                  15

Ser Leu Ser Gln Gln Ile Glu Asn Ile Arg Ser Pro Glu Gly Ser Arg
            20                  25                  30

Lys Asn Pro Ala Arg Thr Cys Arg Asp Leu Lys Met Cys His Ser Asp
        35                  40                  45

Trp Lys Ser Gly Glu Tyr Trp Ile Asp Pro Asn Gln Gly Cys Asn Leu
    50                  55                  60

Asp Ala Ile Lys Val Phe Cys Asn Met Glu Thr Gly Glu Thr Cys Val
65                  70                  75                  80

Tyr Pro Thr Gln Pro Ser Val Ala Gln Lys Asn Trp Tyr Ile Ser Lys
                85                  90                  95

Asn Pro Lys Asp Lys Arg His Val Trp Phe Gly Glu Ser Met Thr Asp
            100                 105                 110

Gly Phe Gln Phe Glu Tyr Gly Gly Gln Gly Ser Asp Pro Ala Asp Val
            115                 120                 125

Ala Ile Gln Leu Thr Phe Leu Arg Leu Met Ser Thr Glu Ala Ser Gln
    130                 135                 140

Asn Ile Thr Tyr His Cys Lys Asn Ser Val Ala Tyr Met Asp Gln Gln
145                 150                 155                 160

Thr Gly Asn Leu Lys Lys Ala Leu Leu Leu Lys Gly Ser Asn Glu Ile
                165                 170                 175

Glu Ile Arg Ala Glu Gly Asn Ser Arg Phe Thr Tyr Ser Val Thr Val
            180                 185                 190

Asp Gly Cys Thr Ser His Thr Gly Ala Trp Gly Lys Thr Val Ile Glu
            195                 200                 205

Tyr Lys Thr Thr Lys Ser Ser Arg Leu Pro Ile Ile Asp Val Ala Pro
    210                 215                 220

Leu Asp Val Gly Ala Pro Asp Gln Glu Phe Gly Phe Asp Val Gly Pro
225                 230                 235                 240

Val Cys Phe Leu

<210> SEQ ID NO 27
<211> LENGTH: 244
<212> TYPE: PRT
<213> ORGANISM: Artificial Sequence
<220> FEATURE:
<223> OTHER INFORMATION: Trimerization peptide (Type I), KS version

<400> SEQUENCE: 27
```

```
Asp Ala Asn Val Val Arg Asp Arg Asp Leu Glu Val Asp Thr Thr Leu
1               5                   10                  15

Lys Ser Leu Ser Gln Gln Ile Glu Asn Ile Arg Ser Pro Glu Gly Ser
            20                  25                  30

Arg Lys Asn Pro Ala Arg Thr Cys Arg Asp Leu Lys Met Cys His Ser
            35                  40                  45

Asp Trp Lys Ser Gly Glu Tyr Trp Ile Asp Pro Asn Gln Gly Cys Asn
        50                  55                  60

Leu Asp Ala Ile Lys Val Phe Cys Asn Met Glu Thr Gly Glu Thr Cys
65                  70                  75                  80

Val Tyr Pro Thr Gln Pro Ser Val Ala Gln Lys Asn Trp Tyr Ile Ser
                85                  90                  95

Lys Asn Pro Lys Asp Lys Arg His Val Trp Phe Gly Glu Ser Met Thr
            100                 105                 110

Asp Gly Phe Gln Phe Glu Tyr Gly Gly Gln Gly Ser Asp Pro Ala Asp
            115                 120                 125

Val Ala Ile Gln Leu Thr Phe Leu Arg Leu Met Ser Thr Glu Ala Ser
        130                 135                 140

Gln Asn Ile Thr Tyr His Cys Lys Asn Ser Val Ala Tyr Met Asp Gln
145                 150                 155                 160

Gln Thr Gly Asn Leu Lys Lys Ala Leu Leu Leu Lys Gly Ser Asn Glu
            165                 170                 175

Ile Glu Ile Arg Ala Glu Gly Asn Ser Arg Phe Thr Tyr Ser Val Thr
            180                 185                 190

Val Asp Gly Cys Thr Ser His Thr Gly Ala Trp Gly Lys Thr Val Ile
            195                 200                 205

Glu Tyr Lys Thr Thr Lys Ser Ser Arg Leu Pro Ile Ile Asp Val Ala
        210                 215                 220

Pro Leu Asp Val Gly Ala Pro Asp Gln Glu Phe Gly Phe Asp Val Gly
225                 230                 235                 240

Pro Val Cys Phe
```

```
<210> SEQ ID NO 28
<211> LENGTH: 246
<212> TYPE: PRT
<213> ORGANISM: Artificial Sequence
<220> FEATURE:
<223> OTHER INFORMATION: Trimerization peptide (Type I), KS version

<400> SEQUENCE: 28
```

```
Ser Asp Ala Asn Val Val Arg Asp Arg Asp Leu Glu Val Asp Thr Thr
1               5                   10                  15

Leu Lys Ser Leu Ser Gln Gln Ile Glu Asn Ile Arg Ser Pro Glu Gly
            20                  25                  30

Ser Arg Lys Asn Pro Ala Arg Thr Cys Arg Asp Leu Lys Met Cys His
            35                  40                  45

Ser Asp Trp Lys Ser Gly Glu Tyr Trp Ile Asp Pro Asn Gln Gly Cys
        50                  55                  60

Asn Leu Asp Ala Ile Lys Val Phe Cys Asn Met Glu Thr Gly Glu Thr
65                  70                  75                  80

Cys Val Tyr Pro Thr Gln Pro Ser Val Ala Gln Lys Asn Trp Tyr Ile
                85                  90                  95

Ser Lys Asn Pro Lys Asp Lys Arg His Val Trp Phe Gly Glu Ser Met
            100                 105                 110

Thr Asp Gly Phe Gln Phe Glu Tyr Gly Gly Gln Gly Ser Asp Pro Ala
```

```
            115                 120                 125

Asp Val Ala Ile Gln Leu Thr Phe Leu Arg Leu Met Ser Thr Glu Ala
    130                 135                 140

Ser Gln Asn Ile Thr Tyr His Cys Lys Asn Ser Val Ala Tyr Met Asp
145                 150                 155                 160

Gln Gln Thr Gly Asn Leu Lys Lys Ala Leu Leu Leu Lys Gly Ser Asn
                165                 170                 175

Glu Ile Glu Ile Arg Ala Glu Gly Asn Ser Arg Phe Thr Tyr Ser Val
                180                 185                 190

Thr Val Asp Gly Cys Thr Ser His Thr Gly Ala Trp Gly Lys Thr Val
            195                 200                 205

Ile Glu Tyr Lys Thr Thr Lys Ser Ser Arg Leu Pro Ile Ile Asp Val
    210                 215                 220

Ala Pro Leu Asp Val Gly Ala Pro Asp Gln Glu Phe Gly Phe Asp Val
225                 230                 235                 240

Gly Pro Val Cys Phe Leu
                245

<210> SEQ ID NO 29
<211> LENGTH: 247
<212> TYPE: PRT
<213> ORGANISM: Artificial Sequence
<220> FEATURE:
<223> OTHER INFORMATION: Trimerization peptide (Type I), KS version

<400> SEQUENCE: 29

Arg Ser Asp Ala Asn Val Val Arg Asp Arg Asp Leu Glu Val Asp Thr
1               5                   10                  15

Thr Leu Lys Ser Leu Ser Gln Gln Ile Glu Asn Ile Arg Ser Pro Glu
                20                  25                  30

Gly Ser Arg Lys Asn Pro Ala Arg Thr Cys Arg Asp Leu Lys Met Cys
            35                  40                  45

His Ser Asp Trp Lys Ser Gly Glu Tyr Trp Ile Asp Pro Asn Gln Gly
    50                  55                  60

Cys Asn Leu Asp Ala Ile Lys Val Phe Cys Asn Met Glu Thr Gly Glu
65                  70                  75                  80

Thr Cys Val Tyr Pro Thr Gln Pro Ser Val Ala Gln Lys Asn Trp Tyr
                85                  90                  95

Ile Ser Lys Asn Pro Lys Asp Lys Arg His Val Trp Phe Gly Glu Ser
                100                 105                 110

Met Thr Asp Gly Phe Gln Phe Glu Tyr Gly Gly Gln Gly Ser Asp Pro
            115                 120                 125

Ala Asp Val Ala Ile Gln Leu Thr Phe Leu Arg Leu Met Ser Thr Glu
    130                 135                 140

Ala Ser Gln Asn Ile Thr Tyr His Cys Lys Asn Ser Val Ala Tyr Met
145                 150                 155                 160

Asp Gln Gln Thr Gly Asn Leu Lys Lys Ala Leu Leu Leu Lys Gly Ser
                165                 170                 175

Asn Glu Ile Glu Ile Arg Ala Glu Gly Asn Ser Arg Phe Thr Tyr Ser
                180                 185                 190

Val Thr Val Asp Gly Cys Thr Ser His Thr Gly Ala Trp Gly Lys Thr
            195                 200                 205

Val Ile Glu Tyr Lys Thr Thr Lys Ser Ser Arg Leu Pro Ile Ile Asp
    210                 215                 220

Val Ala Pro Leu Asp Val Gly Ala Pro Asp Gln Glu Phe Gly Phe Asp
```

-continued

```
225             230             235             240

Val Gly Pro Val Cys Phe Leu
                245

<210> SEQ ID NO 30
<211> LENGTH: 309
<212> TYPE: PRT
<213> ORGANISM: Artificial Sequence
<220> FEATURE:
<223> OTHER INFORMATION: Trimerization peptide (Type I), with
      glycine-X-Y repeats and D-N mutation at BMP-1 site, QT version

<400> SEQUENCE: 30

Asn Gly Leu Pro Gly Pro Ile Gly Pro Pro Gly Pro Arg Gly Arg Thr
1               5                   10                  15

Gly Asp Ala Gly Pro Val Gly Pro Pro Gly Pro Pro Gly Pro Pro Gly
                20                  25                  30

Pro Pro Gly Pro Pro Ser Ala Gly Phe Asp Phe Ser Phe Leu Pro Gln
            35                  40                  45

Pro Pro Gln Glu Lys Ala His Asp Gly Gly Arg Tyr Tyr Arg Ala Asn
        50                  55                  60

Asp Ala Asn Val Val Arg Asp Arg Asp Leu Glu Val Asp Thr Thr Leu
65                  70                  75                  80

Lys Ser Leu Ser Gln Gln Ile Glu Asn Ile Arg Ser Pro Glu Gly Ser
                85                  90                  95

Arg Lys Asn Pro Ala Arg Thr Cys Arg Asp Leu Lys Met Cys His Ser
                100                 105                 110

Asp Trp Lys Ser Gly Glu Tyr Trp Ile Asp Pro Asn Gln Gly Cys Asn
                115                 120                 125

Leu Asp Ala Ile Lys Val Phe Cys Asn Met Glu Thr Gly Glu Thr Cys
        130                 135                 140

Val Tyr Pro Thr Gln Pro Ser Val Ala Gln Lys Asn Trp Tyr Ile Ser
145                 150                 155                 160

Lys Asn Pro Lys Asp Lys Arg His Val Trp Phe Gly Glu Ser Met Thr
                165                 170                 175

Asp Gly Phe Gln Phe Glu Tyr Gly Gly Gln Gly Ser Asp Pro Ala Asp
                180                 185                 190

Val Ala Ile Gln Leu Thr Phe Leu Arg Leu Met Ser Thr Glu Ala Ser
                195                 200                 205

Gln Asn Ile Thr Tyr His Cys Lys Asn Ser Val Ala Tyr Met Asp Gln
        210                 215                 220

Gln Thr Gly Asn Leu Lys Lys Ala Leu Leu Leu Gln Gly Ser Asn Glu
225                 230                 235                 240

Ile Glu Ile Arg Ala Glu Gly Asn Ser Arg Phe Thr Tyr Ser Val Thr
                245                 250                 255

Val Asp Gly Cys Thr Ser His Thr Gly Ala Trp Gly Lys Thr Val Ile
                260                 265                 270

Glu Tyr Lys Thr Thr Lys Thr Ser Arg Leu Pro Ile Ile Asp Val Ala
                275                 280                 285

Pro Leu Asp Val Gly Ala Pro Asp Gln Glu Phe Gly Phe Asp Val Gly
        290                 295                 300

Pro Val Cys Phe Leu
305

<210> SEQ ID NO 31
<211> LENGTH: 309
```

-continued

<212> TYPE: PRT
<213> ORGANISM: Artificial Sequence
<220> FEATURE:
<223> OTHER INFORMATION: Trimerization peptide (Type I), with
      glycine-X-Y repeats and A-N mutation at BMP-1 site, QT version

<400> SEQUENCE: 31

Asn Gly Leu Pro Gly Pro Ile Gly Pro Pro Gly Pro Arg Gly Arg Thr
1               5                   10                  15

Gly Asp Ala Gly Pro Val Gly Pro Pro Gly Pro Pro Gly Pro Pro Gly
            20                  25                  30

Pro Pro Gly Pro Pro Ser Ala Gly Phe Asp Phe Ser Phe Leu Pro Gln
        35                  40                  45

Pro Pro Gln Glu Lys Ala His Asp Gly Gly Arg Tyr Tyr Arg Asn Asp
    50                  55                  60

Asp Ala Asn Val Val Arg Asp Arg Asp Leu Glu Val Asp Thr Thr Leu
65                  70                  75                  80

Lys Ser Leu Ser Gln Gln Ile Glu Asn Ile Arg Ser Pro Glu Gly Ser
            85                  90                  95

Arg Lys Asn Pro Ala Arg Thr Cys Arg Asp Leu Lys Met Cys His Ser
            100                 105                 110

Asp Trp Lys Ser Gly Glu Tyr Trp Ile Asp Pro Asn Gln Gly Cys Asn
            115                 120                 125

Leu Asp Ala Ile Lys Val Phe Cys Asn Met Glu Thr Gly Glu Thr Cys
        130                 135                 140

Val Tyr Pro Thr Gln Pro Ser Val Ala Gln Lys Asn Trp Tyr Ile Ser
145                 150                 155                 160

Lys Asn Pro Lys Asp Lys Arg His Val Trp Phe Gly Glu Ser Met Thr
                165                 170                 175

Asp Gly Phe Gln Phe Glu Tyr Gly Gly Gln Gly Ser Asp Pro Ala Asp
            180                 185                 190

Val Ala Ile Gln Leu Thr Phe Leu Arg Leu Met Ser Thr Glu Ala Ser
            195                 200                 205

Gln Asn Ile Thr Tyr His Cys Lys Asn Ser Val Ala Tyr Met Asp Gln
    210                 215                 220

Gln Thr Gly Asn Leu Lys Lys Ala Leu Leu Leu Gln Gly Ser Asn Glu
225                 230                 235                 240

Ile Glu Ile Arg Ala Glu Gly Asn Ser Arg Phe Thr Tyr Ser Val Thr
                245                 250                 255

Val Asp Gly Cys Thr Ser His Thr Gly Ala Trp Gly Lys Thr Val Ile
            260                 265                 270

Glu Tyr Lys Thr Thr Lys Thr Ser Arg Leu Pro Ile Ile Asp Val Ala
        275                 280                 285

Pro Leu Asp Val Gly Ala Pro Asp Gln Glu Phe Gly Phe Asp Val Gly
    290                 295                 300

Pro Val Cys Phe Leu
305

<210> SEQ ID NO 32
<211> LENGTH: 311
<212> TYPE: PRT
<213> ORGANISM: Artificial Sequence
<220> FEATURE:
<223> OTHER INFORMATION: Trimerization peptide (Type I), with
      glycine-X-Y repeats and D-N mutation at BMP-1 site, QT version

<400> SEQUENCE: 32

```
Arg Ser Asn Gly Leu Pro Gly Pro Ile Gly Pro Pro Gly Pro Arg Gly
1               5                   10                  15

Arg Thr Gly Asp Ala Gly Pro Val Gly Pro Pro Gly Pro Pro Gly Pro
            20                  25                  30

Pro Gly Pro Pro Gly Pro Pro Ser Ala Gly Phe Asp Phe Ser Phe Leu
            35                  40                  45

Pro Gln Pro Pro Gln Glu Lys Ala His Asp Gly Gly Arg Tyr Tyr Arg
    50                  55                  60

Ala Asn Asp Ala Asn Val Val Arg Asp Arg Asp Leu Glu Val Asp Thr
65                  70                  75                  80

Thr Leu Lys Ser Leu Ser Gln Gln Ile Glu Asn Ile Arg Ser Pro Glu
                85                  90                  95

Gly Ser Arg Lys Asn Pro Ala Arg Thr Cys Arg Asp Leu Lys Met Cys
            100                 105                 110

His Ser Asp Trp Lys Ser Gly Glu Tyr Trp Ile Asp Pro Asn Gln Gly
            115                 120                 125

Cys Asn Leu Asp Ala Ile Lys Val Phe Cys Asn Met Glu Thr Gly Glu
    130                 135                 140

Thr Cys Val Tyr Pro Thr Gln Pro Ser Val Ala Gln Lys Asn Trp Tyr
145                 150                 155                 160

Ile Ser Lys Asn Pro Lys Asp Lys Arg His Val Trp Phe Gly Glu Ser
                165                 170                 175

Met Thr Asp Gly Phe Gln Phe Glu Tyr Gly Gly Gln Gly Ser Asp Pro
            180                 185                 190

Ala Asp Val Ala Ile Gln Leu Thr Phe Leu Arg Leu Met Ser Thr Glu
            195                 200                 205

Ala Ser Gln Asn Ile Thr Tyr His Cys Lys Asn Ser Val Ala Tyr Met
    210                 215                 220

Asp Gln Gln Thr Gly Asn Leu Lys Lys Ala Leu Leu Leu Gln Gly Ser
225                 230                 235                 240

Asn Glu Ile Glu Ile Arg Ala Glu Gly Asn Ser Arg Phe Thr Tyr Ser
                245                 250                 255

Val Thr Val Asp Gly Cys Thr Ser His Thr Gly Ala Trp Gly Lys Thr
            260                 265                 270

Val Ile Glu Tyr Lys Thr Thr Lys Thr Ser Arg Leu Pro Ile Ile Asp
            275                 280                 285

Val Ala Pro Leu Asp Val Gly Ala Pro Asp Gln Glu Phe Gly Phe Asp
    290                 295                 300

Val Gly Pro Val Cys Phe Leu
305                 310
```

<210> SEQ ID NO 33
<211> LENGTH: 311
<212> TYPE: PRT
<213> ORGANISM: Artificial Sequence
<220> FEATURE:
<223> OTHER INFORMATION: Trimerization peptide (Type I), with
      glycine-X-Y repeats and D-N mutation at BMP-1 site, QT version

<400> SEQUENCE: 33

```
Gly Ser Asn Gly Leu Pro Gly Pro Ile Gly Pro Pro Gly Pro Arg Gly
1               5                   10                  15

Arg Thr Gly Asp Ala Gly Pro Val Gly Pro Pro Gly Pro Pro Gly Pro
            20                  25                  30

Pro Gly Pro Pro Gly Pro Pro Ser Ala Gly Phe Asp Phe Ser Phe Leu
            35                  40                  45
```

-continued

```
Pro Gln Pro Pro Gln Glu Lys Ala His Asp Gly Gly Arg Tyr Tyr Arg
    50              55              60

Ala Asn Asp Ala Asn Val Val Arg Asp Arg Asp Leu Glu Val Asp Thr
65              70              75              80

Thr Leu Lys Ser Leu Ser Gln Gln Ile Glu Asn Ile Arg Ser Pro Glu
            85              90              95

Gly Ser Arg Lys Asn Pro Ala Arg Thr Cys Arg Asp Leu Lys Met Cys
            100             105             110

His Ser Asp Trp Lys Ser Gly Glu Tyr Trp Ile Asp Pro Asn Gln Gly
            115             120             125

Cys Asn Leu Asp Ala Ile Lys Val Phe Cys Asn Met Glu Thr Gly Glu
    130             135             140

Thr Cys Val Tyr Pro Thr Gln Pro Ser Val Ala Gln Lys Asn Trp Tyr
145             150             155             160

Ile Ser Lys Asn Pro Lys Asp Lys Arg His Val Trp Phe Gly Glu Ser
            165             170             175

Met Thr Asp Gly Phe Gln Phe Glu Tyr Gly Gly Gln Gly Ser Asp Pro
            180             185             190

Ala Asp Val Ala Ile Gln Leu Thr Phe Leu Arg Leu Met Ser Thr Glu
            195             200             205

Ala Ser Gln Asn Ile Thr Tyr His Cys Lys Asn Ser Val Ala Tyr Met
    210             215             220

Asp Gln Gln Thr Gly Asn Leu Lys Lys Ala Leu Leu Leu Gln Gly Ser
225             230             235             240

Asn Glu Ile Glu Ile Arg Ala Glu Gly Asn Ser Arg Phe Thr Tyr Ser
            245             250             255

Val Thr Val Asp Gly Cys Thr Ser His Thr Gly Ala Trp Gly Lys Thr
            260             265             270

Val Ile Glu Tyr Lys Thr Thr Lys Thr Ser Arg Leu Pro Ile Ile Asp
            275             280             285

Val Ala Pro Leu Asp Val Gly Ala Pro Asp Gln Glu Phe Gly Phe Asp
    290             295             300

Val Gly Pro Val Cys Phe Leu
305             310

<210> SEQ ID NO 34
<211> LENGTH: 234
<212> TYPE: PRT
<213> ORGANISM: Artificial Sequence
<220> FEATURE:
<223> OTHER INFORMATION: Trimerization peptide (Type III)

<400> SEQUENCE: 34

Asp Glu Ile Met Thr Ser Leu Lys Ser Val Asn Gly Gln Ile Glu Ser
1               5               10              15

Leu Ile Ser Pro Asp Gly Ser Arg Lys Asn Pro Ala Arg Asn Cys Arg
            20              25              30

Asp Leu Lys Phe Cys His Pro Glu Leu Lys Ser Gly Glu Tyr Trp Val
            35              40              45

Asp Pro Asn Gln Gly Cys Lys Leu Asp Ala Ile Lys Val Phe Cys Asn
    50              55              60

Met Glu Thr Gly Glu Thr Cys Ile Ser Ala Asn Pro Leu Asn Val Pro
65              70              75              80

Arg Lys His Trp Trp Thr Asp Ser Ser Ala Glu Lys Lys His Val Trp
            85              90              95
```

```
Phe Gly Glu Ser Met Asp Gly Gly Phe Gln Phe Ser Tyr Gly Asn Pro
            100                 105                 110

Glu Leu Pro Glu Asp Val Leu Asp Val Gln Leu Ala Phe Leu Arg Leu
            115                 120                 125

Leu Ser Ser Arg Ala Ser Gln Asn Ile Thr Tyr His Cys Lys Asn Ser
        130                 135                 140

Ile Ala Tyr Met Asp Gln Ala Ser Gly Asn Val Lys Lys Ala Leu Lys
145                 150                 155                 160

Leu Met Gly Ser Asn Glu Gly Glu Phe Lys Ala Glu Gly Asn Ser Lys
                165                 170                 175

Phe Thr Tyr Thr Val Leu Glu Asp Gly Cys Thr Lys His Thr Gly Glu
            180                 185                 190

Trp Ser Lys Thr Val Phe Glu Tyr Arg Thr Arg Lys Ala Val Arg Leu
            195                 200                 205

Pro Ile Val Asp Ile Ala Pro Tyr Asp Ile Gly Gly Pro Asp Gln Glu
        210                 215                 220

Phe Gly Val Asp Val Gly Pro Val Cys Phe
225                 230
```

```
<210> SEQ ID NO 35
<211> LENGTH: 244
<212> TYPE: PRT
<213> ORGANISM: Artificial Sequence
<220> FEATURE:
<223> OTHER INFORMATION: Trimerization peptide (Type III)

<400> SEQUENCE: 35
```

```
Glu Pro Met Asp Phe Lys Ile Asn Thr Asp Glu Ile Met Thr Ser Leu
1               5                   10                  15

Lys Ser Val Asn Gly Gln Ile Glu Ser Leu Ile Ser Pro Asp Gly Ser
            20                  25                  30

Arg Lys Asn Pro Ala Arg Asn Cys Arg Asp Leu Lys Phe Cys His Pro
        35                  40                  45

Glu Leu Lys Ser Gly Glu Tyr Trp Val Asp Pro Asn Gln Gly Cys Lys
        50                  55                  60

Leu Asp Ala Ile Lys Val Phe Cys Asn Met Glu Thr Gly Glu Thr Cys
65                  70                  75                  80

Ile Ser Ala Asn Pro Leu Asn Val Pro Arg Lys His Trp Trp Thr Asp
                85                  90                  95

Ser Ser Ala Glu Lys Lys His Val Trp Phe Gly Glu Ser Met Asp Gly
            100                 105                 110

Gly Phe Gln Phe Ser Tyr Gly Asn Pro Glu Leu Pro Glu Asp Val Leu
        115                 120                 125

Asp Val Gln Leu Ala Phe Leu Arg Leu Leu Ser Ser Arg Ala Ser Gln
        130                 135                 140

Asn Ile Thr Tyr His Cys Lys Asn Ser Ile Ala Tyr Met Asp Gln Ala
145                 150                 155                 160

Ser Gly Asn Val Lys Lys Ala Leu Lys Leu Met Gly Ser Asn Glu Gly
                165                 170                 175

Glu Phe Lys Ala Glu Gly Asn Ser Lys Phe Thr Tyr Thr Val Leu Glu
            180                 185                 190

Asp Gly Cys Thr Lys His Thr Gly Glu Trp Ser Lys Thr Val Phe Glu
            195                 200                 205

Tyr Arg Thr Arg Lys Ala Val Arg Leu Pro Ile Val Asp Ile Ala Pro
        210                 215                 220
```

```
Tyr Asp Ile Gly Gly Pro Asp Gln Glu Phe Gly Val Asp Val Gly Pro
225                 230                 235                 240

Val Cys Phe Leu

<210> SEQ ID NO 36
<211> LENGTH: 245
<212> TYPE: PRT
<213> ORGANISM: Artificial Sequence
<220> FEATURE:
<223> OTHER INFORMATION: Trimerization peptide (Type III)

<400> SEQUENCE: 36

Ser Glu Pro Met Asp Phe Lys Ile Asn Thr Asp Glu Ile Met Thr Ser
1               5                   10                  15

Leu Lys Ser Val Asn Gly Gln Ile Glu Ser Leu Ile Ser Pro Asp Gly
            20                  25                  30

Ser Arg Lys Asn Pro Ala Arg Asn Cys Arg Asp Leu Lys Phe Cys His
        35                  40                  45

Pro Glu Leu Lys Ser Gly Glu Tyr Trp Val Asp Pro Asn Gln Gly Cys
    50                  55                  60

Lys Leu Asp Ala Ile Lys Val Phe Cys Asn Met Glu Thr Gly Glu Thr
65                  70                  75                  80

Cys Ile Ser Ala Asn Pro Leu Asn Val Pro Arg Lys His Trp Trp Thr
                85                  90                  95

Asp Ser Ser Ala Glu Lys Lys His Val Trp Phe Gly Glu Ser Met Asp
            100                 105                 110

Gly Gly Phe Gln Phe Ser Tyr Gly Asn Pro Glu Leu Pro Glu Asp Val
            115                 120                 125

Leu Asp Val Gln Leu Ala Phe Leu Arg Leu Leu Ser Ser Arg Ala Ser
    130                 135                 140

Gln Asn Ile Thr Tyr His Cys Lys Asn Ser Ile Ala Tyr Met Asp Gln
145                 150                 155                 160

Ala Ser Gly Asn Val Lys Lys Ala Leu Lys Leu Met Gly Ser Asn Glu
                165                 170                 175

Gly Glu Phe Lys Ala Glu Gly Asn Ser Lys Phe Thr Tyr Thr Val Leu
            180                 185                 190

Glu Asp Gly Cys Thr Lys His Thr Gly Glu Trp Ser Lys Thr Val Phe
            195                 200                 205

Glu Tyr Arg Thr Arg Lys Ala Val Arg Leu Pro Ile Val Asp Ile Ala
    210                 215                 220

Pro Tyr Asp Ile Gly Gly Pro Asp Gln Glu Phe Gly Val Asp Val Gly
225                 230                 235                 240

Pro Val Cys Phe Leu
                245

<210> SEQ ID NO 37
<211> LENGTH: 246
<212> TYPE: PRT
<213> ORGANISM: Artificial Sequence
<220> FEATURE:
<223> OTHER INFORMATION: Trimerization peptide (Type III)

<400> SEQUENCE: 37

Arg Ser Glu Pro Met Asp Phe Lys Ile Asn Thr Asp Glu Ile Met Thr
1               5                   10                  15

Ser Leu Lys Ser Val Asn Gly Gln Ile Glu Ser Leu Ile Ser Pro Asp
            20                  25                  30
```

-continued

```
Gly Ser Arg Lys Asn Pro Ala Arg Asn Cys Arg Asp Leu Lys Phe Cys
        35              40                  45

His Pro Glu Leu Lys Ser Gly Glu Tyr Trp Val Asp Pro Asn Gln Gly
    50              55                  60

Cys Lys Leu Asp Ala Ile Lys Val Phe Cys Asn Met Glu Thr Gly Glu
65              70                  75                  80

Thr Cys Ile Ser Ala Asn Pro Leu Asn Val Pro Arg Lys His Trp Trp
                85                  90                  95

Thr Asp Ser Ser Ala Glu Lys Lys His Val Trp Phe Gly Glu Ser Met
            100             105                 110

Asp Gly Gly Phe Gln Phe Ser Tyr Gly Asn Pro Glu Leu Pro Glu Asp
            115                 120                 125

Val Leu Asp Val Gln Leu Ala Phe Leu Arg Leu Leu Ser Ser Arg Ala
    130                 135                 140

Ser Gln Asn Ile Thr Tyr His Cys Lys Asn Ser Ile Ala Tyr Met Asp
145                 150                 155                 160

Gln Ala Ser Gly Asn Val Lys Lys Ala Leu Lys Leu Met Gly Ser Asn
                165                 170                 175

Glu Gly Glu Phe Lys Ala Glu Gly Asn Ser Lys Phe Thr Tyr Thr Val
            180                 185                 190

Leu Glu Asp Gly Cys Thr Lys His Thr Gly Glu Trp Ser Lys Thr Val
            195                 200                 205

Phe Glu Tyr Arg Thr Arg Lys Ala Val Arg Leu Pro Ile Val Asp Ile
    210                 215                 220

Ala Pro Tyr Asp Ile Gly Gly Pro Asp Gln Glu Phe Gly Val Asp Val
225                 230                 235                 240

Gly Pro Val Cys Phe Leu
                245

<210> SEQ ID NO 38
<211> LENGTH: 244
<212> TYPE: PRT
<213> ORGANISM: Artificial Sequence
<220> FEATURE:
<223> OTHER INFORMATION: Trimerization peptide (Type I), QT version

<400> SEQUENCE: 38

Ala Asn Val Val Arg Asp Arg Asp Leu Glu Val Asp Thr Thr Leu Lys
1               5                   10                  15

Ser Leu Ser Gln Gln Ile Glu Asn Ile Arg Ser Pro Glu Gly Ser Arg
                20                  25                  30

Lys Asn Pro Ala Arg Thr Cys Arg Asp Leu Lys Met Cys His Ser Asp
        35              40                  45

Trp Lys Ser Gly Glu Tyr Trp Ile Asp Pro Asn Gln Gly Cys Asn Leu
    50              55                  60

Asp Ala Ile Lys Val Phe Cys Asn Met Glu Thr Gly Glu Thr Cys Val
65              70                  75                  80

Tyr Pro Thr Gln Pro Ser Val Ala Gln Lys Asn Trp Tyr Ile Ser Lys
                85                  90                  95

Asn Pro Lys Asp Lys Arg His Val Trp Phe Gly Glu Ser Met Thr Asp
            100             105                 110

Gly Phe Gln Phe Glu Tyr Gly Gly Gln Gly Ser Asp Pro Ala Asp Val
            115                 120                 125

Ala Ile Gln Leu Thr Phe Leu Arg Leu Met Ser Thr Glu Ala Ser Gln
    130                 135                 140
```

```
Asn Ile Thr Tyr His Cys Lys Asn Ser Val Ala Tyr Met Asp Gln Gln
145                 150                 155                 160

Thr Gly Asn Leu Lys Lys Ala Leu Leu Leu Gln Gly Ser Asn Glu Ile
                165                 170                 175

Glu Ile Arg Ala Glu Gly Asn Ser Arg Phe Thr Tyr Ser Val Thr Val
            180                 185                 190

Asp Gly Cys Thr Ser His Thr Gly Ala Trp Gly Lys Thr Val Ile Glu
            195                 200                 205

Tyr Lys Thr Thr Lys Thr Ser Arg Leu Pro Ile Ile Asp Val Ala Pro
    210                 215                 220

Leu Asp Val Gly Ala Pro Asp Gln Glu Phe Gly Phe Asp Val Gly Pro
225                 230                 235                 240

Val Cys Phe Leu
```

```
<210> SEQ ID NO 39
<211> LENGTH: 246
<212> TYPE: PRT
<213> ORGANISM: Artificial Sequence
<220> FEATURE:
<223> OTHER INFORMATION: Trimerization peptide (Type I), QT version

<400> SEQUENCE: 39
```

```
Ser Asp Ala Asn Val Val Arg Asp Arg Asp Leu Glu Val Asp Thr Thr
1               5                   10                  15

Leu Lys Ser Leu Ser Gln Gln Ile Glu Asn Ile Arg Ser Pro Glu Gly
            20                  25                  30

Ser Arg Lys Asn Pro Ala Arg Thr Cys Arg Asp Leu Lys Met Cys His
        35                  40                  45

Ser Asp Trp Lys Ser Gly Glu Tyr Trp Ile Asp Pro Asn Gln Gly Cys
    50                  55                  60

Asn Leu Asp Ala Ile Lys Val Phe Cys Asn Met Glu Thr Gly Glu Thr
65                  70                  75                  80

Cys Val Tyr Pro Thr Gln Pro Ser Val Ala Gln Lys Asn Trp Tyr Ile
                85                  90                  95

Ser Lys Asn Pro Lys Asp Lys Arg His Val Trp Phe Gly Glu Ser Met
            100                 105                 110

Thr Asp Gly Phe Gln Phe Glu Tyr Gly Gly Gln Gly Ser Asp Pro Ala
            115                 120                 125

Asp Val Ala Ile Gln Leu Thr Phe Leu Arg Leu Met Ser Thr Glu Ala
        130                 135                 140

Ser Gln Asn Ile Thr Tyr His Cys Lys Asn Ser Val Ala Tyr Met Asp
145                 150                 155                 160

Gln Gln Thr Gly Asn Leu Lys Lys Ala Leu Leu Leu Gln Gly Ser Asn
                165                 170                 175

Glu Ile Glu Ile Arg Ala Glu Gly Asn Ser Arg Phe Thr Tyr Ser Val
            180                 185                 190

Thr Val Asp Gly Cys Thr Ser His Thr Gly Ala Trp Gly Lys Thr Val
            195                 200                 205

Ile Glu Tyr Lys Thr Thr Lys Thr Ser Arg Leu Pro Ile Ile Asp Val
    210                 215                 220

Ala Pro Leu Asp Val Gly Ala Pro Asp Gln Glu Phe Gly Phe Asp Val
225                 230                 235                 240

Gly Pro Val Cys Phe Leu
                245
```

-continued

<210> SEQ ID NO 40
<211> LENGTH: 247
<212> TYPE: PRT
<213> ORGANISM: Artificial Sequence
<220> FEATURE:
<223> OTHER INFORMATION: Trimerization peptide (Type I), QT version

<400> SEQUENCE: 40

```
Arg Ser Asp Ala Asn Val Val Arg Asp Arg Asp Leu Glu Val Asp Thr
1               5                   10                  15

Thr Leu Lys Ser Leu Ser Gln Gln Ile Glu Asn Ile Arg Ser Pro Glu
            20                  25                  30

Gly Ser Arg Lys Asn Pro Ala Arg Thr Cys Arg Asp Leu Lys Met Cys
        35                  40                  45

His Ser Asp Trp Lys Ser Gly Glu Tyr Trp Ile Asp Pro Asn Gln Gly
        50                  55                  60

Cys Asn Leu Asp Ala Ile Lys Val Phe Cys Asn Met Glu Thr Gly Glu
65                  70                  75                  80

Thr Cys Val Tyr Pro Thr Gln Pro Ser Val Ala Gln Lys Asn Trp Tyr
                85                  90                  95

Ile Ser Lys Asn Pro Lys Asp Lys Arg His Val Trp Phe Gly Glu Ser
            100                 105                 110

Met Thr Asp Gly Phe Gln Phe Glu Tyr Gly Gly Gln Gly Ser Asp Pro
            115                 120                 125

Ala Asp Val Ala Ile Gln Leu Thr Phe Leu Arg Leu Met Ser Thr Glu
        130                 135                 140

Ala Ser Gln Asn Ile Thr Tyr His Cys Lys Asn Ser Val Ala Tyr Met
145                 150                 155                 160

Asp Gln Gln Thr Gly Asn Leu Lys Lys Ala Leu Leu Leu Gln Gly Ser
                165                 170                 175

Asn Glu Ile Glu Ile Arg Ala Glu Gly Asn Ser Arg Phe Thr Tyr Ser
            180                 185                 190

Val Thr Val Asp Gly Cys Thr Ser His Thr Gly Ala Trp Gly Lys Thr
            195                 200                 205

Val Ile Glu Tyr Lys Thr Thr Lys Thr Ser Arg Leu Pro Ile Ile Asp
        210                 215                 220

Val Ala Pro Leu Asp Val Gly Ala Pro Asp Gln Glu Phe Gly Phe Asp
225                 230                 235                 240

Val Gly Pro Val Cys Phe Leu
                245
```

<210> SEQ ID NO 41
<211> LENGTH: 247
<212> TYPE: PRT
<213> ORGANISM: Artificial Sequence
<220> FEATURE:
<223> OTHER INFORMATION: Trimerization peptide (Type I), QT version

<400> SEQUENCE: 41

```
Gly Ser Asp Ala Asn Val Val Arg Asp Arg Asp Leu Glu Val Asp Thr
1               5                   10                  15

Thr Leu Lys Ser Leu Ser Gln Gln Ile Glu Asn Ile Arg Ser Pro Glu
            20                  25                  30

Gly Ser Arg Lys Asn Pro Ala Arg Thr Cys Arg Asp Leu Lys Met Cys
        35                  40                  45

His Ser Asp Trp Lys Ser Gly Glu Tyr Trp Ile Asp Pro Asn Gln Gly
        50                  55                  60
```

```
Cys Asn Leu Asp Ala Ile Lys Val Phe Cys Asn Met Glu Thr Gly Glu
65              70                  75                  80

Thr Cys Val Tyr Pro Thr Gln Pro Ser Val Ala Gln Lys Asn Trp Tyr
                85                  90                  95

Ile Ser Lys Asn Pro Lys Asp Lys Arg His Val Trp Phe Gly Glu Ser
            100                 105                 110

Met Thr Asp Gly Phe Gln Phe Glu Tyr Gly Gly Gln Gly Ser Asp Pro
            115                 120                 125

Ala Asp Val Ala Ile Gln Leu Thr Phe Leu Arg Leu Met Ser Thr Glu
        130                 135                 140

Ala Ser Gln Asn Ile Thr Tyr His Cys Lys Asn Ser Val Ala Tyr Met
145                 150                 155                 160

Asp Gln Gln Thr Gly Asn Leu Lys Lys Ala Leu Leu Leu Gln Gly Ser
                165                 170                 175

Asn Glu Ile Glu Ile Arg Ala Glu Gly Asn Ser Arg Phe Thr Tyr Ser
            180                 185                 190

Val Thr Val Asp Gly Cys Thr Ser His Thr Gly Ala Trp Gly Lys Thr
            195                 200                 205

Val Ile Glu Tyr Lys Thr Thr Lys Thr Ser Arg Leu Pro Ile Ile Asp
        210                 215                 220

Val Ala Pro Leu Asp Val Gly Ala Pro Asp Gln Glu Phe Gly Phe Asp
225                 230                 235                 240

Val Gly Pro Val Cys Phe Leu
                245
```

```
<210> SEQ ID NO 42
<211> LENGTH: 234
<212> TYPE: PRT
<213> ORGANISM: Artificial Sequence
<220> FEATURE:
<223> OTHER INFORMATION: Fc

<400> SEQUENCE: 42

Arg Val Glu Pro Lys Ser Cys Asp Lys Thr His Thr Cys Pro Pro Cys
1               5                   10                  15

Pro Ala Pro Glu Leu Leu Gly Gly Pro Ser Val Phe Leu Phe Pro Pro
                20                  25                  30

Lys Pro Lys Asp Thr Leu Met Ile Ser Arg Thr Pro Glu Val Thr Cys
            35                  40                  45

Val Val Val Asp Val Ser His Glu Asp Pro Glu Val Lys Phe Asn Trp
        50                  55                  60

Tyr Val Asp Gly Val Glu Val His Asn Ala Lys Thr Lys Pro Arg Glu
65              70                  75                  80

Glu Gln Tyr Asn Ser Thr Tyr Arg Val Val Ser Val Leu Thr Val Leu
                85                  90                  95

His Gln Asp Trp Leu Asn Gly Lys Glu Tyr Lys Cys Lys Val Ser Asn
            100                 105                 110

Lys Ala Leu Pro Ala Pro Ile Glu Lys Thr Ile Ser Lys Ala Lys Gly
            115                 120                 125

Gln Pro Arg Glu Pro Gln Val Tyr Thr Leu Pro Pro Ser Arg Asp Glu
        130                 135                 140

Leu Thr Lys Asn Gln Val Ser Leu Thr Cys Leu Val Lys Gly Phe Tyr
145                 150                 155                 160

Pro Ser Asp Ile Ala Val Glu Trp Glu Ser Asn Gly Gln Pro Glu Asn
                165                 170                 175
```

-continued

```
Asn Tyr Lys Thr Thr Pro Pro Val Leu Asp Ser Asp Gly Ser Phe Phe
            180             185             190

Leu Tyr Ser Lys Leu Thr Val Asp Lys Ser Arg Trp Gln Gln Gly Asn
            195             200             205

Val Phe Ser Cys Ser Val Met His Glu Ala Leu His Asn His Tyr Thr
            210             215             220

Gln Lys Ser Leu Ser Leu Ser Pro Gly Lys
225                 230

<210> SEQ ID NO 43
<211> LENGTH: 1628
<212> TYPE: PRT
<213> ORGANISM: Artificial Sequence
<220> FEATURE:
<223> OTHER INFORMATION: Full length Endo180-Fc (D1-10-Fc)

<400> SEQUENCE: 43

Met Gly Pro Gly Arg Pro Ala Pro Ala Pro Trp Pro Arg His Leu Leu
1               5               10              15

Arg Cys Val Leu Leu Leu Gly Cys Leu His Leu Gly Arg Pro Gly Ala
            20              25              30

Pro Gly Asp Ala Ala Leu Pro Glu Pro Asn Val Phe Leu Ile Phe Ser
            35              40              45

His Gly Leu Gln Gly Cys Leu Glu Ala Gln Gly Gly Gln Val Arg Val
            50              55              60

Thr Pro Ala Cys Asn Thr Ser Leu Pro Ala Gln Arg Trp Lys Trp Val
65                  70              75                  80

Ser Arg Asn Arg Leu Phe Asn Leu Gly Thr Met Gln Cys Leu Gly Thr
                85              90              95

Gly Trp Pro Gly Thr Asn Thr Thr Ala Ser Leu Gly Met Tyr Glu Cys
            100             105             110

Asp Arg Glu Ala Leu Asn Leu Arg Trp His Cys Arg Thr Leu Gly Asp
            115             120             125

Gln Leu Ser Leu Leu Leu Gly Ala Arg Thr Ser Asn Ile Ser Lys Pro
            130             135             140

Gly Thr Leu Glu Arg Gly Asp Gln Thr Arg Ser Gly Gln Trp Arg Ile
145             150             155             160

Tyr Gly Ser Glu Glu Asp Leu Cys Ala Leu Pro Tyr His Glu Val Tyr
                165             170             175

Thr Ile Gln Gly Asn Ser His Gly Lys Pro Cys Thr Ile Pro Phe Lys
            180             185             190

Tyr Asp Asn Gln Trp Phe His Gly Cys Thr Ser Thr Gly Arg Glu Asp
            195             200             205

Gly His Leu Trp Cys Ala Thr Thr Gln Asp Tyr Gly Lys Asp Glu Arg
            210             215             220

Trp Gly Phe Cys Pro Ile Lys Ser Asn Asp Cys Glu Thr Phe Trp Asp
225                 230             235                 240

Lys Asp Gln Leu Thr Asp Ser Cys Tyr Gln Phe Asn Phe Gln Ser Thr
            245             250             255

Leu Ser Trp Arg Glu Ala Trp Ala Ser Cys Glu Gln Gln Gly Ala Asp
            260             265             270

Leu Leu Ser Ile Thr Glu Ile His Glu Gln Thr Tyr Ile Asn Gly Leu
            275             280             285

Leu Thr Gly Tyr Ser Ser Thr Leu Trp Ile Gly Leu Asn Asp Leu Asp
            290             295             300
```

-continued

```
Thr Ser Gly Gly Trp Gln Trp Ser Asp Asn Ser Pro Leu Lys Tyr Leu
305             310             315             320

Asn Trp Glu Ser Asp Gln Pro Asp Asn Pro Ser Glu Glu Asn Cys Gly
            325             330             335

Val Ile Arg Thr Glu Ser Ser Gly Gly Trp Gln Asn Arg Asp Cys Ser
            340             345             350

Ile Ala Leu Pro Tyr Val Cys Lys Lys Lys Pro Asn Ala Thr Ala Glu
            355             360             365

Pro Thr Pro Pro Asp Arg Trp Ala Asn Val Lys Val Glu Cys Glu Pro
            370             375             380

Ser Trp Gln Pro Phe Gln Gly His Cys Tyr Arg Leu Gln Ala Glu Lys
385             390             395             400

Arg Ser Trp Gln Glu Ser Lys Lys Ala Cys Leu Arg Gly Gly Gly Asp
            405             410             415

Leu Val Ser Ile His Ser Met Ala Glu Leu Glu Phe Ile Thr Lys Gln
            420             425             430

Ile Lys Gln Glu Val Glu Glu Leu Trp Ile Gly Leu Asn Asp Leu Lys
            435             440             445

Leu Gln Met Asn Phe Glu Trp Ser Asp Gly Ser Leu Val Ser Phe Thr
            450             455             460

His Trp His Pro Phe Glu Pro Asn Asn Phe Arg Asp Ser Leu Glu Asp
465             470             475             480

Cys Val Thr Ile Trp Gly Pro Glu Gly Arg Trp Asn Asp Ser Pro Cys
            485             490             495

Asn Gln Ser Leu Pro Ser Ile Cys Lys Lys Ala Gly Gln Leu Ser Gln
            500             505             510

Gly Ala Ala Glu Glu Asp His Gly Cys Arg Lys Gly Trp Thr Trp His
            515             520             525

Ser Pro Ser Cys Tyr Trp Leu Gly Glu Asp Gln Val Thr Tyr Ser Glu
            530             535             540

Ala Arg Arg Leu Cys Thr Asp His Gly Ser Gln Leu Val Thr Ile Thr
545             550             555             560

Asn Arg Phe Glu Gln Ala Phe Val Ser Ser Leu Ile Tyr Asn Trp Glu
            565             570             575

Gly Glu Tyr Phe Trp Thr Ala Leu Gln Asp Leu Asn Ser Thr Gly Ser
            580             585             590

Phe Phe Trp Leu Ser Gly Asp Glu Val Met Tyr Thr His Trp Asn Arg
            595             600             605

Asp Gln Pro Gly Tyr Ser Arg Gly Gly Cys Val Ala Leu Ala Thr Gly
            610             615             620

Ser Ala Met Gly Leu Trp Glu Val Lys Asn Cys Thr Ser Phe Arg Ala
625             630             635             640

Arg Tyr Ile Cys Arg Gln Ser Leu Gly Thr Pro Val Thr Pro Glu Leu
            645             650             655

Pro Gly Pro Asp Pro Thr Pro Ser Leu Thr Gly Ser Cys Pro Gln Gly
            660             665             670

Trp Ala Ser Asp Thr Lys Leu Arg Tyr Cys Tyr Lys Val Phe Ser Ser
            675             680             685

Glu Arg Leu Gln Asp Lys Lys Ser Trp Val Gln Ala Gln Gly Ala Cys
            690             695             700

Gln Glu Leu Gly Ala Gln Leu Leu Ser Leu Ala Ser Tyr Glu Glu Glu
705             710             715             720
```

-continued

```
His Phe Val Ala Asn Met Leu Asn Lys Ile Phe Gly Glu Ser Glu Pro
                725                 730                 735

Glu Ile His Glu Gln His Trp Phe Trp Ile Gly Leu Asn Arg Arg Asp
            740                 745                 750

Pro Arg Gly Gly Gln Ser Trp Arg Trp Ser Asp Gly Val Gly Phe Ser
            755                 760                 765

Tyr His Asn Phe Asp Arg Ser Arg His Asp Asp Asp Ile Arg Gly
    770                 775                 780

Cys Ala Val Leu Asp Leu Ala Ser Leu Gln Trp Val Ala Met Gln Cys
785                 790                 795                 800

Asp Thr Gln Leu Asp Trp Ile Cys Lys Ile Pro Arg Gly Thr Asp Val
                805                 810                 815

Arg Glu Pro Asp Asp Ser Pro Gln Gly Arg Arg Glu Trp Leu Arg Phe
            820                 825                 830

Gln Glu Ala Glu Tyr Lys Phe Phe Glu His His Ser Thr Trp Ala Gln
            835                 840                 845

Ala Gln Arg Ile Cys Thr Trp Phe Gln Ala Glu Leu Thr Ser Val His
    850                 855                 860

Ser Gln Ala Glu Leu Asp Phe Leu Ser His Asn Leu Gln Lys Phe Ser
865                 870                 875                 880

Arg Ala Gln Glu Gln His Trp Trp Ile Gly Leu His Thr Ser Glu Ser
            885                 890                 895

Asp Gly Arg Phe Arg Trp Thr Asp Gly Ser Ile Ile Asn Phe Ile Ser
            900                 905                 910

Trp Ala Pro Gly Lys Pro Arg Pro Val Gly Lys Asp Lys Lys Cys Val
            915                 920                 925

Tyr Met Thr Ala Ser Arg Glu Asp Trp Gly Asp Gln Arg Cys Leu Thr
    930                 935                 940

Ala Leu Pro Tyr Ile Cys Lys Arg Ser Asn Val Thr Lys Glu Thr Gln
945                 950                 955                 960

Pro Pro Asp Leu Pro Thr Thr Ala Leu Gly Gly Cys Pro Ser Asp Trp
                965                 970                 975

Ile Gln Phe Leu Asn Lys Cys Phe Gln Val Gln Gly Gln Glu Pro Gln
            980                 985                 990

Ser Arg Val Lys Trp Ser Glu Ala  Gln Phe Ser Cys Glu  Gln Gln Glu
        995                 1000                1005

Ala Gln  Leu Val Thr Ile Thr  Asn Pro Leu Glu Gln  Ala Phe Ile
    1010                1015                1020

Thr Ala  Ser Leu Pro Asn Val  Thr Phe Asp Leu Trp  Ile Gly Leu
    1025                1030                1035

His Ala  Ser Gln Arg Asp Phe  Gln Trp Val Glu Gln  Glu Pro Leu
    1040                1045                1050

Met Tyr  Ala Asn Trp Ala Pro  Gly Glu Pro Ser Gly  Pro Ser Pro
    1055                1060                1065

Ala Pro  Ser Gly Asn Lys Pro  Thr Ser Cys Ala Val  Val Leu His
    1070                1075                1080

Ser Pro  Ser Ala His Phe Thr  Gly Arg Trp Asp Asp  Arg Ser Cys
    1085                1090                1095

Thr Glu  Glu Thr His Gly Phe  Ile Cys Gln Lys Gly  Thr Asp Pro
    1100                1105                1110

Ser Leu  Ser Pro Ser Pro Ala  Ala Leu Pro Pro Ala  Pro Gly Thr
    1115                1120                1125

Glu Leu  Ser Tyr Leu Asn Gly  Thr Phe Arg Leu Leu  Gln Lys Pro
```

```
            1130              1135              1140

Leu Arg Trp His Asp Ala Leu  Leu Leu Cys Glu Ser  Arg Asn Ala
    1145              1150              1155

Ser Leu Ala Tyr Val Pro Asp  Pro Tyr Thr Gln Ala  Phe Leu Thr
    1160              1165              1170

Gln Ala Ala Arg Gly Leu Arg  Thr Pro Leu Trp Ile  Gly Leu Ala
    1175              1180              1185

Gly Glu Glu Gly Ser Arg Arg  Tyr Ser Trp Val Ser  Glu Glu Pro
    1190              1195              1200

Leu Asn Tyr Val Gly Trp Gln  Asp Gly Glu Pro Gln  Gln Pro Gly
    1205              1210              1215

Gly Cys Thr Tyr Val Asp Val  Asp Gly Ala Trp Arg  Thr Thr Ser
    1220              1225              1230

Cys Asp Thr Lys Leu Gln Gly  Ala Val Cys Gly Val  Ser Ser Gly
    1235              1240              1245

Pro Pro Pro Pro Arg Arg Ile  Ser Tyr His Gly Ser  Cys Pro Gln
    1250              1255              1260

Gly Leu Ala Asp Ser Ala Trp  Ile Pro Phe Arg Glu  His Cys Tyr
    1265              1270              1275

Ser Phe His Met Glu Leu Leu  Leu Gly His Lys Glu  Ala Arg Gln
    1280              1285              1290

Arg Cys Gln Arg Ala Gly Gly  Ala Val Leu Ser Ile  Leu Asp Glu
    1295              1300              1305

Met Glu Asn Val Phe Val Trp  Glu His Leu Gln Ser  Tyr Glu Gly
    1310              1315              1320

Gln Ser Arg Gly Ala Trp Leu  Gly Met Asn Phe Asn  Pro Lys Gly
    1325              1330              1335

Gly Thr Leu Val Trp Gln Asp  Asn Thr Ala Val Asn  Tyr Ser Asn
    1340              1345              1350

Trp Gly Pro Pro Gly Leu Gly  Pro Ser Met Leu Ser  His Asn Ser
    1355              1360              1365

Cys Tyr Trp Ile Gln Ser Asn  Ser Gly Leu Trp Arg  Pro Gly Ala
    1370              1375              1380

Cys Thr Asn Ile Thr Met Gly  Val Val Cys Lys Arg  Val Glu Pro
    1385              1390              1395

Lys Ser Cys Asp Lys Thr His  Thr Cys Pro Pro Cys  Pro Ala Pro
    1400              1405              1410

Glu Leu Leu Gly Gly Pro Ser  Val Phe Leu Phe Pro  Pro Lys Pro
    1415              1420              1425

Lys Asp Thr Leu Met Ile Ser  Arg Thr Pro Glu Val  Thr Cys Val
    1430              1435              1440

Val Val Asp Val Ser His Glu  Asp Pro Glu Val Lys  Phe Asn Trp
    1445              1450              1455

Tyr Val Asp Gly Val Glu Val  His Asn Ala Lys Thr  Lys Pro Arg
    1460              1465              1470

Glu Glu Gln Tyr Asn Ser Thr  Tyr Arg Val Val Ser  Val Leu Thr
    1475              1480              1485

Val Leu His Gln Asp Trp Leu  Asn Gly Lys Glu Tyr  Lys Cys Lys
    1490              1495              1500

Val Ser Asn Lys Ala Leu Pro  Ala Pro Ile Glu Lys  Thr Ile Ser
    1505              1510              1515

Lys Ala Lys Gly Gln Pro Arg  Glu Pro Gln Val Tyr  Thr Leu Pro
    1520              1525              1530
```

-continued

```
Pro Ser  Arg Asp Glu Leu Thr  Lys Asn Gln Val Ser  Leu Thr Cys
    1535                1540                1545

Leu Val  Lys Gly Phe Tyr Pro  Ser Asp Ile Ala Val  Glu Trp Glu
    1550                1555                1560

Ser Asn  Gly Gln Pro Glu Asn  Asn Tyr Lys Thr Thr  Pro Pro Val
    1565                1570                1575

Leu Asp  Ser Asp Gly Ser Phe  Phe Leu Tyr Ser Lys  Leu Thr Val
    1580                1585                1590

Asp Lys  Ser Arg Trp Gln Gln  Gly Asn Val Phe Ser  Cys Ser Val
    1595                1600                1605

Met His  Glu Ala Leu His Asn  His Tyr Thr Gln Lys  Ser Leu Ser
    1610                1615                1620

Leu Ser  Pro Gly Lys
    1625

<210> SEQ ID NO 44
<211> LENGTH: 1598
<212> TYPE: PRT
<213> ORGANISM: Artificial Sequence
<220> FEATURE:
<223> OTHER INFORMATION: Mature Endo-180-Fc(D1-10-Fc)

<400> SEQUENCE: 44

Gly Ala Pro Gly Asp Ala Ala Leu Pro Glu Pro Asn Val Phe Leu Ile
1               5                   10                  15

Phe Ser His Gly Leu Gln Gly Cys Leu Glu Ala Gln Gly Gly Gln Val
            20                  25                  30

Arg Val Thr Pro Ala Cys Asn Thr Ser Leu Pro Ala Gln Arg Trp Lys
        35                  40                  45

Trp Val Ser Arg Asn Arg Leu Phe Asn Leu Gly Thr Met Gln Cys Leu
    50                  55                  60

Gly Thr Gly Trp Pro Gly Thr Asn Thr Thr Ala Ser Leu Gly Met Tyr
65                  70                  75                  80

Glu Cys Asp Arg Glu Ala Leu Asn Leu Arg Trp His Cys Arg Thr Leu
            85                  90                  95

Gly Asp Gln Leu Ser Leu Leu Leu Gly Ala Arg Thr Ser Asn Ile Ser
            100                 105                 110

Lys Pro Gly Thr Leu Glu Arg Gly Asp Gln Thr Arg Ser Gly Gln Trp
        115                 120                 125

Arg Ile Tyr Gly Ser Glu Glu Asp Leu Cys Ala Leu Pro Tyr His Glu
    130                 135                 140

Val Tyr Thr Ile Gln Gly Asn Ser His Gly Lys Pro Cys Thr Ile Pro
145                 150                 155                 160

Phe Lys Tyr Asp Asn Gln Trp Phe His Gly Cys Thr Ser Thr Gly Arg
            165                 170                 175

Glu Asp Gly His Leu Trp Cys Ala Thr Thr Gln Asp Tyr Gly Lys Asp
            180                 185                 190

Glu Arg Trp Gly Phe Cys Pro Ile Lys Ser Asn Asp Cys Glu Thr Phe
        195                 200                 205

Trp Asp Lys Asp Gln Leu Thr Asp Ser Cys Tyr Gln Phe Asn Phe Gln
    210                 215                 220

Ser Thr Leu Ser Trp Arg Glu Ala Trp Ala Ser Cys Glu Gln Gln Gly
225                 230                 235                 240

Ala Asp Leu Leu Ser Ile Thr Glu Ile His Glu Gln Thr Tyr Ile Asn
            245                 250                 255
```

```
Gly Leu Leu Thr Gly Tyr Ser Ser Thr Leu Trp Ile Gly Leu Asn Asp
            260                 265                 270

Leu Asp Thr Ser Gly Gly Trp Gln Trp Ser Asp Asn Ser Pro Leu Lys
            275                 280                 285

Tyr Leu Asn Trp Glu Ser Asp Gln Pro Asp Asn Pro Ser Glu Glu Asn
    290                 295                 300

Cys Gly Val Ile Arg Thr Glu Ser Ser Gly Gly Trp Gln Asn Arg Asp
305                 310                 315                 320

Cys Ser Ile Ala Leu Pro Tyr Val Cys Lys Lys Pro Asn Ala Thr
            325                 330                 335

Ala Glu Pro Thr Pro Pro Asp Arg Trp Ala Asn Val Lys Val Glu Cys
            340                 345                 350

Glu Pro Ser Trp Gln Pro Phe Gln Gly His Cys Tyr Arg Leu Gln Ala
            355                 360                 365

Glu Lys Arg Ser Trp Gln Glu Ser Lys Lys Ala Cys Leu Arg Gly Gly
    370                 375                 380

Gly Asp Leu Val Ser Ile His Ser Met Ala Glu Leu Glu Phe Ile Thr
385                 390                 395                 400

Lys Gln Ile Lys Gln Glu Val Glu Glu Leu Trp Ile Gly Leu Asn Asp
            405                 410                 415

Leu Lys Leu Gln Met Asn Phe Glu Trp Ser Asp Gly Ser Leu Val Ser
            420                 425                 430

Phe Thr His Trp His Pro Phe Glu Pro Asn Asn Phe Arg Asp Ser Leu
            435                 440                 445

Glu Asp Cys Val Thr Ile Trp Gly Pro Glu Gly Arg Trp Asn Asp Ser
    450                 455                 460

Pro Cys Asn Gln Ser Leu Pro Ser Ile Cys Lys Lys Ala Gly Gln Leu
465                 470                 475                 480

Ser Gln Gly Ala Ala Glu Glu Asp His Gly Cys Arg Lys Gly Trp Thr
            485                 490                 495

Trp His Ser Pro Ser Cys Tyr Trp Leu Gly Glu Asp Gln Val Thr Tyr
            500                 505                 510

Ser Glu Ala Arg Arg Leu Cys Thr Asp His Gly Ser Gln Leu Val Thr
            515                 520                 525

Ile Thr Asn Arg Phe Glu Gln Ala Phe Val Ser Ser Leu Ile Tyr Asn
    530                 535                 540

Trp Glu Gly Glu Tyr Phe Trp Thr Ala Leu Gln Asp Leu Asn Ser Thr
545                 550                 555                 560

Gly Ser Phe Phe Trp Leu Ser Gly Asp Glu Val Met Tyr Thr His Trp
            565                 570                 575

Asn Arg Asp Gln Pro Gly Tyr Ser Arg Gly Gly Cys Val Ala Leu Ala
            580                 585                 590

Thr Gly Ser Ala Met Gly Leu Trp Glu Val Lys Asn Cys Thr Ser Phe
            595                 600                 605

Arg Ala Arg Tyr Ile Cys Arg Gln Ser Leu Gly Thr Pro Val Thr Pro
    610                 615                 620

Glu Leu Pro Gly Pro Asp Pro Thr Pro Ser Leu Thr Gly Ser Cys Pro
625                 630                 635                 640

Gln Gly Trp Ala Ser Asp Thr Lys Leu Arg Tyr Cys Tyr Lys Val Phe
            645                 650                 655

Ser Ser Glu Arg Leu Gln Asp Lys Lys Ser Trp Val Gln Ala Gln Gly
            660                 665                 670
```

Ala Cys Gln Glu Leu Gly Ala Gln Leu Leu Ser Leu Ala Ser Tyr Glu
        675                 680                 685

Glu Glu His Phe Val Ala Asn Met Leu Asn Lys Ile Phe Gly Glu Ser
    690                 695                 700

Glu Pro Glu Ile His Glu Gln His Trp Phe Trp Ile Gly Leu Asn Arg
705                 710                 715                 720

Arg Asp Pro Arg Gly Gly Gln Ser Trp Arg Trp Ser Asp Gly Val Gly
                725                 730                 735

Phe Ser Tyr His Asn Phe Asp Arg Ser Arg His Asp Asp Asp Ile
            740                 745                 750

Arg Gly Cys Ala Val Leu Asp Leu Ala Ser Leu Gln Trp Val Ala Met
        755                 760                 765

Gln Cys Asp Thr Gln Leu Asp Trp Ile Cys Lys Ile Pro Arg Gly Thr
    770                 775                 780

Asp Val Arg Glu Pro Asp Asp Ser Pro Gln Gly Arg Arg Glu Trp Leu
785                 790                 795                 800

Arg Phe Gln Glu Ala Glu Tyr Lys Phe Phe Glu His His Ser Thr Trp
                805                 810                 815

Ala Gln Ala Gln Arg Ile Cys Thr Trp Phe Gln Ala Glu Leu Thr Ser
            820                 825                 830

Val His Ser Gln Ala Glu Leu Asp Phe Leu Ser His Asn Leu Gln Lys
        835                 840                 845

Phe Ser Arg Ala Gln Glu Gln His Trp Trp Ile Gly Leu His Thr Ser
    850                 855                 860

Glu Ser Asp Gly Arg Phe Arg Trp Thr Asp Gly Ser Ile Ile Asn Phe
865                 870                 875                 880

Ile Ser Trp Ala Pro Gly Lys Pro Arg Pro Val Gly Lys Asp Lys Lys
                885                 890                 895

Cys Val Tyr Met Thr Ala Ser Arg Glu Asp Trp Gly Asp Gln Arg Cys
            900                 905                 910

Leu Thr Ala Leu Pro Tyr Ile Cys Lys Arg Ser Asn Val Thr Lys Glu
        915                 920                 925

Thr Gln Pro Pro Asp Leu Pro Thr Thr Ala Leu Gly Gly Cys Pro Ser
    930                 935                 940

Asp Trp Ile Gln Phe Leu Asn Lys Cys Phe Gln Val Gln Gly Gln Glu
945                 950                 955                 960

Pro Gln Ser Arg Val Lys Trp Ser Glu Ala Gln Phe Ser Cys Glu Gln
                965                 970                 975

Gln Glu Ala Gln Leu Val Thr Ile Thr Asn Pro Leu Glu Gln Ala Phe
            980                 985                 990

Ile Thr Ala Ser Leu Pro Asn Val  Thr Phe Asp Leu Trp  Ile Gly Leu
        995                 1000                 1005

His Ala  Ser Gln Arg Asp Phe  Gln Trp Val Glu Gln  Glu Pro Leu
    1010                 1015                 1020

Met Tyr  Ala Asn Trp Ala Pro  Gly Glu Pro Ser Gly  Pro Ser Pro
    1025                 1030                 1035

Ala Pro  Ser Gly Asn Lys Pro  Thr Ser Cys Ala Val  Val Leu His
    1040                 1045                 1050

Ser Pro  Ser Ala His Phe Thr  Gly Arg Trp Asp Asp  Arg Ser Cys
    1055                 1060                 1065

Thr Glu  Glu Thr His Gly Phe  Ile Cys Gln Lys Gly  Thr Asp Pro
    1070                 1075                 1080

Ser Leu  Ser Pro Ser Pro Ala  Ala Leu Pro Pro Ala  Pro Gly Thr

-continued

```
        1085                1090                1095

Glu Leu Ser Tyr Leu Asn Gly Thr Phe Arg Leu Leu Gln Lys Pro
    1100                1105                1110

Leu Arg Trp His Asp Ala Leu Leu Leu Cys Glu Ser Arg Asn Ala
    1115                1120                1125

Ser Leu Ala Tyr Val Pro Asp Pro Tyr Thr Gln Ala Phe Leu Thr
    1130                1135                1140

Gln Ala Ala Arg Gly Leu Arg Thr Pro Leu Trp Ile Gly Leu Ala
    1145                1150                1155

Gly Glu Glu Gly Ser Arg Arg Tyr Ser Trp Val Ser Glu Glu Pro
    1160                1165                1170

Leu Asn Tyr Val Gly Trp Gln Asp Gly Glu Pro Gln Gln Pro Gly
    1175                1180                1185

Gly Cys Thr Tyr Val Asp Val Asp Gly Ala Trp Arg Thr Thr Ser
    1190                1195                1200

Cys Asp Thr Lys Leu Gln Gly Ala Val Cys Gly Val Ser Ser Gly
    1205                1210                1215

Pro Pro Pro Pro Arg Arg Ile Ser Tyr His Gly Ser Cys Pro Gln
    1220                1225                1230

Gly Leu Ala Asp Ser Ala Trp Ile Pro Phe Arg Glu His Cys Tyr
    1235                1240                1245

Ser Phe His Met Glu Leu Leu Leu Gly His Lys Glu Ala Arg Gln
    1250                1255                1260

Arg Cys Gln Arg Ala Gly Gly Ala Val Leu Ser Ile Leu Asp Glu
    1265                1270                1275

Met Glu Asn Val Phe Val Trp Glu His Leu Gln Ser Tyr Glu Gly
    1280                1285                1290

Gln Ser Arg Gly Ala Trp Leu Gly Met Asn Phe Asn Pro Lys Gly
    1295                1300                1305

Gly Thr Leu Val Trp Gln Asp Asn Thr Ala Val Asn Tyr Ser Asn
    1310                1315                1320

Trp Gly Pro Pro Gly Leu Gly Pro Ser Met Leu Ser His Asn Ser
    1325                1330                1335

Cys Tyr Trp Ile Gln Ser Asn Ser Gly Leu Trp Arg Pro Gly Ala
    1340                1345                1350

Cys Thr Asn Ile Thr Met Gly Val Val Cys Lys Arg Val Glu Pro
    1355                1360                1365

Lys Ser Cys Asp Lys Thr His Thr Cys Pro Pro Cys Pro Ala Pro
    1370                1375                1380

Glu Leu Leu Gly Gly Pro Ser Val Phe Leu Phe Pro Pro Lys Pro
    1385                1390                1395

Lys Asp Thr Leu Met Ile Ser Arg Thr Pro Glu Val Thr Cys Val
    1400                1405                1410

Val Val Asp Val Ser His Glu Asp Pro Glu Val Lys Phe Asn Trp
    1415                1420                1425

Tyr Val Asp Gly Val Glu Val His Asn Ala Lys Thr Lys Pro Arg
    1430                1435                1440

Glu Glu Gln Tyr Asn Ser Thr Tyr Arg Val Val Ser Val Leu Thr
    1445                1450                1455

Val Leu His Gln Asp Trp Leu Asn Gly Lys Glu Tyr Lys Cys Lys
    1460                1465                1470

Val Ser Asn Lys Ala Leu Pro Ala Pro Ile Glu Lys Thr Ile Ser
    1475                1480                1485
```

```
Lys Ala  Lys Gly Gln Pro Arg  Glu Pro Gln Val Tyr  Thr Leu Pro
    1490              1495              1500

Pro Ser  Arg Asp Glu Leu Thr  Lys Asn Gln Val Ser  Leu Thr Cys
    1505              1510              1515

Leu Val  Lys Gly Phe Tyr Pro  Ser Asp Ile Ala Val  Glu Trp Glu
    1520              1525              1530

Ser Asn  Gly Gln Pro Glu Asn  Asn Tyr Lys Thr Thr  Pro Pro Val
    1535              1540              1545

Leu Asp  Ser Asp Gly Ser Phe  Phe Leu Tyr Ser Lys  Leu Thr Val
    1550              1555              1560

Asp Lys  Ser Arg Trp Gln Gln  Gly Asn Val Phe Ser  Cys Ser Val
    1565              1570              1575

Met His  Glu Ala Leu His Asn  His Tyr Thr Gln Lys  Ser Leu Ser
    1580              1585              1590

Leu Ser  Pro Gly Lys
    1595
```

```
<210> SEQ ID NO 45
<211> LENGTH: 427
<212> TYPE: PRT
<213> ORGANISM: Artificial Sequence
<220> FEATURE:
<223> OTHER INFORMATION: Full Length D6-Fc

<400> SEQUENCE: 45

Met Gly Pro Gly Arg Pro Ala Pro Ala Pro Trp Pro Arg His Leu Leu
1               5                   10                  15

Arg Cys Val Leu Leu Leu Gly Cys Leu His Leu Gly Arg Pro Arg Ser
            20                  25                  30

Pro Val Thr Pro Glu Leu Pro Gly Pro Asp Pro Thr Pro Ser Leu Thr
            35                  40                  45

Gly Ser Cys Pro Gln Gly Trp Ala Ser Asp Thr Lys Leu Arg Tyr Cys
    50                  55                  60

Tyr Lys Val Phe Ser Ser Glu Arg Leu Gln Asp Lys Lys Ser Trp Val
65                  70                  75                  80

Gln Ala Gln Gly Ala Cys Gln Glu Leu Gly Ala Gln Leu Leu Ser Leu
                85                  90                  95

Ala Ser Tyr Glu Glu Glu His Phe Val Ala Asn Met Leu Asn Lys Ile
            100                 105                 110

Phe Gly Glu Ser Glu Pro Glu Ile His Glu Gln His Trp Phe Trp Ile
            115                 120                 125

Gly Leu Asn Arg Arg Asp Pro Arg Gly Gly Gln Ser Trp Arg Trp Ser
    130                 135                 140

Asp Gly Val Gly Phe Ser Tyr His Asn Phe Asp Arg Ser Arg His Asp
145                 150                 155                 160

Asp Asp Asp Ile Arg Gly Cys Ala Val Leu Asp Leu Ala Ser Leu Gln
                165                 170                 175

Trp Val Ala Met Gln Cys Asp Thr Gln Leu Asp Trp Ile Cys Lys Ile
            180                 185                 190

Pro Arg Val Glu Pro Lys Ser Cys Asp Lys Thr His Thr Cys Pro Pro
            195                 200                 205

Cys Pro Ala Pro Glu Leu Leu Gly Gly Pro Ser Val Phe Leu Phe Pro
    210                 215                 220

Pro Lys Pro Lys Asp Thr Leu Met Ile Ser Arg Thr Pro Glu Val Thr
225                 230                 235                 240
```

-continued

```
Cys Val Val Val Asp Val Ser His Glu Asp Pro Glu Val Lys Phe Asn
            245                 250                 255

Trp Tyr Val Asp Gly Val Glu Val His Asn Ala Lys Thr Lys Pro Arg
            260                 265                 270

Glu Glu Gln Tyr Asn Ser Thr Tyr Arg Val Val Ser Val Leu Thr Val
            275                 280                 285

Leu His Gln Asp Trp Leu Asn Gly Lys Glu Tyr Lys Cys Lys Val Ser
    290                 295                 300

Asn Lys Ala Leu Pro Ala Pro Ile Glu Lys Thr Ile Ser Lys Ala Lys
305                 310                 315                 320

Gly Gln Pro Arg Glu Pro Gln Val Tyr Thr Leu Pro Pro Ser Arg Asp
                325                 330                 335

Glu Leu Thr Lys Asn Gln Val Ser Leu Thr Cys Leu Val Lys Gly Phe
            340                 345                 350

Tyr Pro Ser Asp Ile Ala Val Glu Trp Glu Ser Asn Gly Gln Pro Glu
            355                 360                 365

Asn Asn Tyr Lys Thr Thr Pro Pro Val Leu Asp Ser Asp Gly Ser Phe
    370                 375                 380

Phe Leu Tyr Ser Lys Leu Thr Val Asp Lys Ser Arg Trp Gln Gln Gly
385                 390                 395                 400

Asn Val Phe Ser Cys Ser Val Met His Glu Ala Leu His Asn His Tyr
                405                 410                 415

Thr Gln Lys Ser Leu Ser Leu Ser Pro Gly Lys
            420                 425
```

```
<210> SEQ ID NO 46
<211> LENGTH: 397
<212> TYPE: PRT
<213> ORGANISM: Artificial Sequence
<220> FEATURE:
<223> OTHER INFORMATION: Mature D6-Fc

<400> SEQUENCE: 46
```

```
Arg Ser Pro Val Thr Pro Glu Leu Pro Gly Pro Asp Pro Thr Pro Ser
1               5                   10                  15

Leu Thr Gly Ser Cys Pro Gln Gly Trp Ala Ser Asp Thr Lys Leu Arg
            20                  25                  30

Tyr Cys Tyr Lys Val Phe Ser Ser Glu Arg Leu Gln Asp Lys Lys Ser
        35                  40                  45

Trp Val Gln Ala Gln Gly Ala Cys Gln Glu Leu Gly Ala Gln Leu Leu
    50                  55                  60

Ser Leu Ala Ser Tyr Glu Glu Glu His Phe Val Ala Asn Met Leu Asn
65                  70                  75                  80

Lys Ile Phe Gly Glu Ser Glu Pro Glu Ile His Glu Gln His Trp Phe
                85                  90                  95

Trp Ile Gly Leu Asn Arg Arg Asp Pro Arg Gly Gly Gln Ser Trp Arg
            100                 105                 110

Trp Ser Asp Gly Val Gly Phe Ser Tyr His Asn Phe Asp Arg Ser Arg
        115                 120                 125

His Asp Asp Asp Asp Ile Arg Gly Cys Ala Val Leu Asp Leu Ala Ser
    130                 135                 140

Leu Gln Trp Val Ala Met Gln Cys Asp Thr Gln Leu Asp Trp Ile Cys
145                 150                 155                 160

Lys Ile Pro Arg Val Glu Pro Lys Ser Cys Asp Lys Thr His Thr Cys
                165                 170                 175
```

-continued

```
Pro Pro Cys Pro Ala Pro Glu Leu Leu Gly Gly Pro Ser Val Phe Leu
            180             185             190

Phe Pro Pro Lys Pro Lys Asp Thr Leu Met Ile Ser Arg Thr Pro Glu
            195             200             205

Val Thr Cys Val Val Val Asp Val Ser His Glu Asp Pro Glu Val Lys
    210             215             220

Phe Asn Trp Tyr Val Asp Gly Val Glu Val His Asn Ala Lys Thr Lys
225             230             235             240

Pro Arg Glu Glu Gln Tyr Asn Ser Thr Tyr Arg Val Val Ser Val Leu
            245             250             255

Thr Val Leu His Gln Asp Trp Leu Asn Gly Lys Glu Tyr Lys Cys Lys
            260             265             270

Val Ser Asn Lys Ala Leu Pro Ala Pro Ile Glu Lys Thr Ile Ser Lys
            275             280             285

Ala Lys Gly Gln Pro Arg Glu Pro Gln Val Tyr Thr Leu Pro Pro Ser
    290             295             300

Arg Asp Glu Leu Thr Lys Asn Gln Val Ser Leu Thr Cys Leu Val Lys
305             310             315             320

Gly Phe Tyr Pro Ser Asp Ile Ala Val Glu Trp Glu Ser Asn Gly Gln
            325             330             335

Pro Glu Asn Asn Tyr Lys Thr Thr Pro Pro Val Leu Asp Ser Asp Gly
            340             345             350

Ser Phe Phe Leu Tyr Ser Lys Leu Thr Val Asp Lys Ser Arg Trp Gln
            355             360             365

Gln Gly Asn Val Phe Ser Cys Ser Val Met His Glu Ala Leu His Asn
    370             375             380

His Tyr Thr Gln Lys Ser Leu Ser Leu Ser Pro Gly Lys
385             390             395
```